(12) United States Patent
Mollenhauer et al.

(10) Patent No.: US 6,346,606 B1
(45) Date of Patent: Feb. 12, 2002

(54) PROTEIN CONTAINING A SCAVENGER RECEPTOR CYSTEINE RICH DOMAIN

(75) Inventors: Jan Mollenhauer, Schönau; Annemarie Poustka, Heidelberg, both of (DE)

(73) Assignee: Deutsches Krebsforschungszentrum Stiftung des offentlichen Rechts, Heidelberg (DE)

( * ) Notice: Subject to any disclaimer, the term of this patent is extended or adjusted under 35 U.S.C. 154(b) by 0 days.

(21) Appl. No.: 09/341,587

(22) PCT Filed: Jan. 9, 1998

(86) PCT No.: PCT/DE98/00096

§ 371 Date: Aug. 31, 1999

§ 102(e) Date: Aug. 31, 1999

(87) PCT Pub. No.: WO98/30687

PCT Pub. Date: Jul. 16, 1998

(30) Foreign Application Priority Data

Jan. 9, 1997 (DE) .......................... 197 00 519
Jul. 18, 1997 (DE) .......................... 197 30 997

(51) Int. Cl.[7] .......................... C07K 1/00; C07K 14/00; C07K 17/00; C12P 21/02; C12P 21/04
(52) U.S. Cl. ..................... 530/350; 435/69.1; 435/70.3; 514/1; 514/2; 514/12
(58) Field of Search .............................. 530/350; 514/1, 514/2, 12; 435/69.1, 70.3

(56) References Cited

PUBLICATIONS

Hillier L. et al. "The Wash.U–Merk EST Project, AC T89953" EMBL Database, Apr. 7, 1995, Heidelberg.
Resnick D. et al. "The SRCR Superfamily: a family reminiscent of the Ig superfamily." Trends in Biochemical Sciences: 19 (1) Jan. 1994. pp. 5–8.

Rasheed B. et al. "Chromosome 10 deletion mapping in human gliomas: a common deletion region in 10q25." Oncogene: 10 (11) Jun. 1, 1995 pp. 2243–2246.

Albarosa, R. et al. "Deletion mapping of gliomas suggests the presence of two small regions for candidate tumor–suppressor genes in a 17–cm interval on chromosome 10q." Amer. Journal of Human Genetics: 58 (6) Jun. 1996 pp. 1260–1267.

Mollenhauer, J. et al. "DMB1, a new member f the SRCR superfamily, on chromosome 10q25.3–26.1 is deleted in malignant brain tumors." Nature Genetics: 17 (1) Sep. 1997 pp. 32–39.

Amino acid database, Accession #Q9Y4V9, 1999.*

Amino acid database, Accession #Q95218, 1997.*

Takito et al. Hensin, a New Collecting Duct Protein Involved in the In Vitro Plasticity of Intercalated Cell Polarity. J. Clin. Invest. 98(10):2324–2331, 1996.*

Nucleic acid database, Accession #AJ000342, 1999.*

Nucleic acid database, Accession #AF043112, 1999.*

* cited by examiner

*Primary Examiner*—Sheela Huff
*Assistant Examiner*—Alana M. Harris
(74) *Attorney, Agent, or Firm*—Steven J. Hultquist; Marianne Fuierer

(57) ABSTRACT

The present invention relates to a protein containing an SRCR domain, a nucleic acid encoding such a protein and a method to produce same. The invention further relates to the use of the nucleic acid and the protein and antibodies directed against the protein.

19 Claims, 39 Drawing Sheets

FIG. 1A

| FIG. 1A | FIG. 1B | FIG. 1C |

FIG. 1

```
1    caggacacnagtcttacctgtggagctgcccccacaatggctggctctcccacaactgtg
     ------------------------------------------------------------
     gtcctgtgntcagaatggacacctcgacggggtgttaccgaccgagagggtgttgacac

G  H  ?  S  Y  L  W  S  C  P  H  N  G  W  L  S  H  N  C  G 61   gccatcatgaagatgctggtgtcatctgctcagctgctcagtcccagtcaacgcccaggc
     ------------------------------------------------------------
     cggtagtacttctacgaccacagtagacgagtcgacgagtcagggtcagttgcgggtccg

H  H  E  D  A  G  V  I  C  S  A  A  Q  S  Q  S  T  P  R  P 121  cagatacttggctgaccaccaacttaccggcattgacagtaggatctgaatccagtttgg
     ------------------------------------------------------------
     gtctatgaaccgactggtggttgaatggccgtaactgtcatcctagacttaggtcaaacc

D  T  W  L  T  T  N  L  P  A  L  T  V  G  S  E  S  S  L  A 181  ctctgaggctggtgaatggaggtgacaggtgtcgaggccgagtggaggtcctgtatcgag
     ------------------------------------------------------------
     gagactccgaccacttacctccactgtccacagctccggctcacctccaggacatagctc

L  R  L  V  N  G  D  R  C  R  G  R  V  E  V  L  Y  R  G 241  gctcctggggaaccgtgtgtgatgacagctgggacaccaatgatgccaatgtggtctgca
     ------------------------------------------------------------
     cgaggaccccttggcacacactactgtcgaccctgtggttactacggttacaccagacgt

S  W  G  T  V  C  D  D  S  W  D  T  N  D  A  N  V  V  C  R 301  ggcagctgggctgtggctgggccatgtcggccccaggaaatgcccggtttggccagggct
     ------------------------------------------------------------
     ccgtcgacccgacaccgacccggtacagccggggtccttttacgggccaaaccggtcccga

Q  L  G  C  W  A  M  S  A  P  G  N  A  R  F  G  Q  G  S 361  caggaccattgtcctggatgatgtgcgctgctcagggaatgagtcctacctgtggagct
     ------------------------------------------------------------
     gtcctgggtaacaggacctactacacgcgacgagtcccttactcaggatggacacctcga

G  P  I  V  L  D  D  V  R  C  S  G  N  E  S  Y  L  W  S  C 421  gcccccacaaaggctggctcacccacaactgtggccatcacgaagacgctggtgtcatct
     ------------------------------------------------------------
     cggggtgtttccgaccgagtgggtgttgacaccggtagtgcttctgcgaccacagtaga

P  H  K  G  W  L  T  H  N  C  G  H  H  E  D  A  G  V  I  C 481  gctcagccacccaaataaattctactacgacagattggtggcatccaacaactacaacca
     ------------------------------------------------------------
     cgagtcggtgggtttatttaagatgatgctgtctaaccaccgtaggttgttgatgttggt

S  A  T  Q  I  N  S  T  T  T  D  W  W  H  P  T  T  T  T  T 541  ctgtaggaccctcttcaaattgtggtggcttcttattctatgccagtgggacattctcca
     ------------------------------------------------------------
     gacatcctgggagaagtttaacaccaccgaagaataagatacggtcaccctgtaagaggt

V  G  P  S  S  N  C  G  G  F  L  F  Y  A  S  G  T  F  S  S 601  gcccatcctaccctgcatactaccccaacaatgctaagtgtgtttgggaaatagaagtga
     ------------------------------------------------------------
     cgggtaggatgggacgtatgatggggttgttacgattcacacaaaccctttatcttcact
```

FIG. 1B

```
        P  S  Y  P  A  Y  Y  P  N  N  A  K  C  V  W  E  I  E  V  N
       attctggttatcgcataaacctgggcttcagtaatctgaagttggaggcacaccataact
661    ------------------------------------------------------------
       taagaccaatagcgtatttggacccgaagtcattagacttcaacctccgtgtggtattga S  G  Y  R  I  N  L  G  F  S  N  L  K  L  E  A  H  H  N  C
       gcagttttgattatgttgaaatctttgatggatcattgaatagcagtctcctgctgggga
721    ------------------------------------------------------------
       cgtcaaaactaatacaactttagaaactacctagtaacttatcgtcagaggacgacccct S  F  D  Y  V  E  I  F  D  G  S  L  N  S  S  L  L  L  G  K
       aaatctgtaatgataccaggcaaatatttacatcttcttacaaccgaatgaccattcact
781    ------------------------------------------------------------
       tttagacattactatggtccgtttataaatgtagaagaatgttggcttactggtaagtga I  C  N  D  T  R  Q  I  F  T  S  S  Y  N  R  M  T  I  H  F
       ttcgaagtgacatcagtttccaaaacactggcttttttggcttggtataactccttcccaa
841    ------------------------------------------------------------
       aagcttcactgtagtcaaaggtttttgtgaccgaaaaaccgaaccatattgaggaagggtt R  S  D  I  S  F  Q  N  T  G  F  L  A  W  Y  N  S  F  P  S
       gcgatgccaccttgaggttggtcaatttaaattcatcctatggtctatgtgccgggcgtg
901    ------------------------------------------------------------
       cgctacggtggaactccaaccagttaaatttaagtaggataccagatacacggcccgcac D  A  T  L  R  L  V  N  L  N  S  S  Y  G  L  C  A  G  R  V
       tagaaatttaccatggtggcacctgggggacagtttgtgatgactcctggaccattcagg
961    ------------------------------------------------------------
       atctttaaatggtaccaccgtggacccccctgtcaaacactactgaggacctggtaagtcc E  I  Y  H  G  G  T  W  G  T  V  C  D  D  S  W  T  I  Q  E
       aagctgaggtggtctgcagacagctagggtgtggacgtgcagtttcagcccttggaaatg
1021   ------------------------------------------------------------
       ttcgactccaccagacgtctgtcgatcccacacctgcacgtcaaagtcgggaacctttac A  E  V  V  C  R  Q  L  G  C  G  R  A  V  S  A  L  G  N  A
       catatttggctctggctctggccccatcaccctggacgatgtagagtgctcagggacgg
1081   ------------------------------------------------------------
       gtataaaaccgagaccgagaccggggtagtgggacctgctacatctcacgagtccctgcc Y  F  G  S  G  S  G  P  I  T  L  D  D  V  E  C  S  G  T  E
       aatccactctctggcagtgccggaaccgaggctggttctcccacaactgtaatcatcgtg
1141   ------------------------------------------------------------
       ttaggtgagagaccgtcacggccttggctccgaccaagagggtgttgacattagtagcac S  T  L  W  Q  C  R  N  R  G  W  F  S  H  N  C  N  H  R  E
       aagatgctggtgtcatctgctcaggaaaccatctatcgacacctgctccttttctcaaca
1201   ------------------------------------------------------------
       ttctacgaccacagtagacgagtcctttggtagatagctgtggacgaggaaaagagttgt D  A  G  V  I  C  S  G  N  H  L  S  T  P  A  P  F  L  N  I
       tcacccgtccaaacacagattattcctgcggaggcttcctatcccaaccatcagggact
1261   ------------------------------------------------------------
       agtgggcaggtttgtgtctaataaggacgcctccgaaggataggggttggtagtcccctga T  R  P  N  T  D  Y  S  C  G  G  F  L  S  Q  P  S  G  D  F
       tttccagcccattctatcccgggaactatccaaacaatgccaagtgtgtgtgggacattg
1321   ------------------------------------------------------------
```

FIG. 1C

```
        aaaggtcgggtaagatagggcccttgataggtttgttacggttcacacacaccctgtaac
         S   S   P   F   Y   P   G   N   Y   P   N   N   A   K   C   V   W   D   I   E
1381    aggtgcaaaacaactaccgtgtgactgtgatcttcagagatgtccagcttgaaggtggct
        ------------------------------------------------------------
        tccacgttttgttgatggcacactgacactagaagtctctacaggtcgaacttccacga
         V   Q   N   N   Y   R   V   T   V   I   F   R   D   V   Q   L   E   G   G   C
1441    gcaactatgattatattgaagttttcgatggcccctaccgcagttcccctctcattgctc
        ------------------------------------------------------------
        cgttgatactaatataacttcaaaagctaccggggatggcgtcaaggggagagtaacgag
         N   Y   D   Y   I   E   V   F   D   G   P   Y   R   S   S   P   L   I   A   R
1501    gagtttgtgatggggccagaggctccttcacttcttcctccaacttcatgtccattcgct
        ------------------------------------------------------------
        ctcaaacactaccccggtctccgaggaagtgaagaaggaggttgaagtacaggtaagcga
         V   C   D   G   A   R   G   S   F   T   S   S   N   F   M   S   I   R   F
1561    tcatcagtgaccacagcatcacaaggagagggttccgggctgagtactactccagtccct
        ------------------------------------------------------------
        agtagtcactggtgtcgtagtgttcctctcccaaggcccgactcatgatgaggtcaggga
         I   S   D   H   S   I   T   R   R   G   F   R   A   E   Y   Y   S   S   P   S
1621    ccaatgacagcaccaacctgctctgtctgccaaatcacatgcaagccagtgtgagcagga
        ------------------------------------------------------------
        ggttactgtcgtggttggacgagacagacggtttagtgtacgttcggtcacactcgtcct
         N   D   S   T   N   L   L   C   L   P   N   H   M   Q   A   S   V   S   R   S
1681    gctatctccaatccttgggcttttctgccagtgaccttgtcatttccacctggaatggat
        ------------------------------------------------------------
        cgatagaggttaggaacccgaaaagacggtcactggaacagtaaaggtggaccttaccta
         Y   L   Q   S   L   G   F   S   A   S   D   L   V   I   S   T   W   N   G   Y
1741    actacgagtgtcggccccagataacgccgaacctggtgatattcacaattccctactcag
        ------------------------------------------------------------
        tgatgctcacagccggggtctattgcggcttggaccactataagtgttaagggatgagtc
         Y   E   C   R   P   Q   I   T   P   N   L   V   I   F   T   I   P   Y   S   G
1801    gctgcggcaccttcaagcaggcagacaatgacaccatcgactattccaacttcctcacag
        ------------------------------------------------------------
        cgacgccgtggaagttcgtccgtctgttactgtggtagctgataaggttgaaggagtgtc
         C   G   T   F   K   Q   A   D   N   D   T   I   D   Y   S   N   F   L   T   A
1861    cagctgtctcaggtggcatcatcaagaggaggacagacctccgtattcacgtcagctgca
        ------------------------------------------------------------
        gtcgacagagtccaccgtagtagttctcctcctgtctggaggcataagtgcagtcgacgt
         A   V   S   G   G   I   I   K   R   R   T   D   L   R   I   H   V   S   C   R
1921    gaatgcttcagaacacctgggtcgacaccatgtacattgctaatgacaccatccacgttg
        ------------------------------------------------------------
        cttacgaagtcttgtggacccagctgtggtacatgtaacgattactgtggtaggtgcaac
         M   L   Q   N   T   W   V   D   T   M   Y   I   A   N   D   T   I   H   V   A
1981    ctaataacaccatccaggtc
        --------------------
        gattattgtggtaggtccag
         N   N   T   I   Q   V
```

FIG. 2A

| FIG. 2A | FIG. 2B | FIG. 2C |
|---------|---------|---------|
| FIG. 2D | FIG. 2E | FIG. 2F |
| FIG. 2G | FIG. 2H | FIG. 2I |
| FIG. 2J |         |         |

FIG. 2

```
          tttatagcagcagcagaaatataccaccctagaggacacacctccttttagctaggtacc
    1     ---------+---------+---------+---------+---------+---------+  60
          aaatatcgtcgtcgtctttatatggtgggatctcctgtgtggaggaaaatcgatccatgg tataaatgtccaggattttctattcaattgagaagaacccagcaaaatggggatctccac
   61     ---------+---------+---------+---------+---------+---------+ 120
          atatttacaggtcctaaaagataagttaactcttcttgggtcgttttaccccctagaggtg

M  G  I  S  T  - agtcatccttgaaatgtgtcttttatggggacaagttctatctacaggtgggtggatccc
  121     ---------+---------+---------+---------+---------+---------+ 180
          tcagtaggaactttacacagaaaataccccctgttcaagatagatgtccacccacctaggg

V  I  L  E  M  C  L  L  W  G  Q  V  L  S  T  G  G  W  I  P  - aaggactacagactacgcttcactgattccctcggaggtgcccttggatcaaactgtagc
  181     ---------+---------+---------+---------+---------+---------+ 240
          ttcctgatgtctgatgcgaagtgactaagggagcctccacgggaacctagtttgacatcg

R  T  T  D  Y  A  S  L  I  P  S  E  V  P  L  D  Q  T  V  A  - agaaggttctccatttcctcggagtcgaccctggagtcaactgcagcagaaggttctcc
  241     ---------+---------+---------+---------+---------+---------+ 300
          tcttccaagaggtaaagggagcctcagctgggacctcagttgacgtcgtcttccaagagg

E  G  S  P  F  P  S  E  S  T  L  E  S  T  A  A  E  G  S  P  - gatttccttggagtcaaccctggagtcaactgtagcagaaggttctctgattccctcaga
  301     ---------+---------+---------+---------+---------+---------+ 360
          ctaaaggaacctcagttgggacctcagttgacatcgtcttccaagagactaagggagtct

I  S  L  E  S  T  L  E  S  T  V  A  E  G  S  L  I  P  S  E  - gtcaaccctggagtcaactgtagcagaaggatctgattctggtttggccctgaggctggt
  361     ---------+---------+---------+---------+---------+---------+ 420
          cagttgggacctcagttgacatcgtcttcctagactaagaccaaaccgggactccgacca

S  T  L  E  S  T  V  A  E  G  S  D  S  G  L  A  L  R  L  V  - gaatggagatggcaggtgtcagggccgagtggagatcctataccgaggctcctggggcac
  421     ---------+---------+---------+---------+---------+---------+ 480
          cttacctctaccgtccacagtcccggctcacctctaggatatggctccgaggaccccgtg

```
     cgtgtgtgatgacagctgggacaccaatgatgccaacgtggtctgtaggcagctggttg
481  ---------+---------+---------+---------+---------+---------+ 540
     gcacacactactgtcgaccctgtggttactacggttgcaccagacatccgtcgacccaac

V  C  D  D  S  W  D  T  N  D  A  N  V  V  C  R  Q  L  G  C  - tggctgggccatgtcagctccaggaaatgcctggtttggccagggctcaggacccattgc
541  ---------+---------+---------+---------+---------+---------+ 600
     accgacccggtacagtcgaggtcctttacggaccaaaccggtcccgagtcctgggtaacg

G  W  A  M  S  A  P  G  N  A  W  F  G  Q  G  S  G  P  I  A  - cctggatgatgtgcgctgctcaggacacgaatcctacctgtggagctgcccccacaatgg
601  ---------+---------+---------+---------+---------+---------+ 660
     ggacctactacacgcgacgagtcctgtgcttaggatggacacctcgacggggtgttacc

L  D  D  V  R  C  S  G  H  E  S  Y  L  W  S  C  P  H  N  G  - ctggctctcccataactgtggccatggtgaagatgctggtgttatctgctcagctgccca
661  ---------+---------+---------+---------+---------+---------+ 720
     gaccgagagggtattgacaccggtaccacttctacgaccacaatagacgagtcgacgggt

W  L  S  H  N  C  G  H  G  E  D  A  G  V  I  C  S  A  A  Q  - gcctcagtcaacactcaggccagaaagttggcctgtcaggatatcaccacctgtacccac
721  ---------+---------+---------+---------+---------+---------+ 780
     cggagtcagttgtgagtccggtctttcaaccggacagtcctatagtggtggacatgggtg

P  Q  S  T  L  R  P  E  S  W  P  V  R  I  S  P  P  V  P  T  - agaaggatctgaatccagtttggccctgaggctggtgaatggaggcgacaggtgtcgagg
781  ---------+---------+---------+---------+---------+---------+ 840
     tcttcctagacttaggtcaaaccgggactccgaccacttacctccgctgtccacagctcc

E  G  S  E  S  S  L  A  L  R  L  V  N  G  G  D  R  C  R  G  - ccgagtggaggtcctataccgaggctcctggggcaccgtgtgtgatgactactgggacac
841  ---------+---------+---------+---------+---------+---------+ 900
     ggctcacctccaggatatggctccgaggaccccgtggcacacactactgatgaccctgtg

R  V  E  V  L  Y  R  G  S  W  G  T  V  C  D  D  Y  W  D  T  - caatgatgccaatgtggtctgcaggcagctgggctgtggctgggccatgtcagccccagg
901  ---------+---------+---------+---------+---------+---------+ 960
     gttactacggttacaccagacgtccgtcgacccgacaccgacccggtacagtcggggtcc

N  D  A  N  V  V  C  R  Q  L  G  C  G  W  A  M  S  A  P  G  - aaatgcccagtttggccagggctcaggacccattgtcctggatgatgtgcgctgctcagg
961  ---------+---------+---------+---------+---------+---------+ 1020
     tttacgggtcaaaccggtcccgagtcctgggtaacaggacctactacacgcgacgagtcc

N  A  Q  F  G  Q  G  S  G  P  I  V  L  D  D  V  R  C  S  G  - acacgagtcctacctgtggagctgcccccacaatggctggctcacccacaactgtggcca
1021 ---------+---------+---------+---------+---------+---------+ 1080
     tgtgctcaggatggacacctcgacggggggtgttaccgaccgagtgggtgttgacaccggt

```
      tagtgaagacgctggtgtcatctgctcagctccccagtcccggccgacacccagcccaga
1081  ---------+---------+---------+---------+---------+---------+ 1140
      atcacttctgcgaccacagtagacgagtcgaggggtcagggccggctgtgggtcgggtct

S  E  D  A  G  V  I  C  S  A  P  Q  S  R  P  T  P  S  P  D  - tacttggccgacctcacatgcatcaacagcaggacctgaatccagtttggccctgaggct
1141  ---------+---------+---------+---------+---------+---------+ 1200
      atgaaccggctggagtgtacgtagttgtcgtcctggacttaggtcaaaccgggactccga

T  W  P  T  S  H  A  S  T  A  G  P  E  S  S  L  A  L  R  L  - ggtgaatggaggtgacaggtgtcagggccgagtggaggtcctataccgaggctcctgggg
1201  ---------+---------+---------+---------+---------+---------+ 1260
      ccacttacctccactgtccacagtcccggctcacctccaggatatggctccgaggacccc

V  N  G  G  D  R  C  Q  G  R  V  E  V  L  Y  R  G  S  W  G  - caccgtgtgtgatgatagctgggacaccagtgacgccaatgtggtctgccggcagctggg
1261  ---------+---------+---------+---------+---------+---------+ 1320
      gtggcacacactactatcgaccctgtggtcactgcggttacaccagacggccgtcgaccc

T  V  C  D  D  S  W  D  T  S  D  A  N  V  V  C  R  Q  L  G  - ctgtggctgggccacgtcagccccaggaaatgccggtttggccagggttcaggacccat
1321  ---------+---------+---------+---------+---------+---------+ 1380
      gacaccgacccggtgcagtcggggtcctttacgggccaaaccggtcccaagtcctgggta

C  G  W  A  T  S  A  P  G  N  A  R  F  G  Q  G  S  G  P  I  - tgtcctggatgacgtgcgctgctcaggctatgagtcctacctgtggagctgccccacaa
1381  ---------+---------+---------+---------+---------+---------+ 1440
      acaggacctactgcacgcgacgagtccgatactcaggatggacacctcgacggggtgtt

V  L  D  D  V  R  C  S  G  Y  E  S  Y  L  W  S  C  P  H  N  - tggctggctctcccataactgtcagcacagtgaagacgctggtgtcatctgctcagctgc
1441  ---------+---------+---------+---------+---------+---------+ 1500
      accgaccgagagggtattgacagtcgtgtcacttctgcgaccacagtagacgagtcgacg

G  W  L  S  H  N  C  Q  H  S  E  D  A  G  V  I  C  S  A  A  - ccactcctggtcgacgcccagtccagacacattgccgaccatcaccttgcctgcatcgac
1501  ---------+---------+---------+---------+---------+---------+ 1560
      ggtgaggaccagctgcgggtcaggtctgtgtaacggctggtagtggaacggacgtagctg

H  S  W  S  T  P  S  P  D  T  L  P  T  I  T  L  P  A  S  T  - agtaggatctgaatccagtttggccctgaggctggtgaatggaggtgacaggtgtcaggg
1561  ---------+---------+---------+---------+---------+---------+ 1620
      tcatcctagacttaggtcaaaccgggactccgaccacttacctccactgtccacagtccc

V  G  S  E  S  S  L  A  L  R  L  V  N  G  G  D  R  C  Q  G  - ccgagtggaggtcctataccaaggctcctggggcaccgtgtgcgatgacagctgggacac
1621  ---------+---------+---------+---------+---------+---------+ 1680
      ggctcacctccaggatatggttccgaggaccccgtggcacacgctactgtcgaccctgtg
```

FIG. 2D

```
         R  V  E  V  L  Y  Q  G  S  W  G  T  V  C  D  D  S  W  D  T  - caatgatgccaatgtcgtctgcaggcaaccgggctgtggctgggccatgtcagccccagg
1681   ---------+---------+---------+---------+---------+---------+ 1740
       gttactacggttacagcagacgtccgttggcccgacaccgacccggtacagtcggggtcc

N  D  A  N  V  V  C  R  Q  P  G  C  G  W  A  M  S  A  P  G  - aaatgcccggtttggtcagggctcaggacccattgtcctggatgatgtgcgctgctcagg
1741   ---------+---------+---------+---------+---------+---------+ 1800
       tttacgggccaaaccagtcccgagtcctgggtaacaggacctactacacgcgacgagtcc

N  A  R  F  G  Q  G  S  G  P  I  V  L  D  D  V  R  C  S  G  - acacgagtcttacccgtggagctgccccacaatggctggctctcccacaactgtggcca
1801   ---------+---------+---------+---------+---------+---------+ 1860
       tgtgctcagaatgggcacctcgacggggtgttaccgaccgagagggtgttgacaccggt

H  E  S  Y  P  W  S  C  P  H  N  G  W  L  S  H  N  C  G  H  - tagtgaagacgctggtgtcatctgctcagcttcccagtcccggccaacacctagtccaga
1861   ---------+---------+---------+---------+---------+---------+ 1920
       atcacttctgcgaccacagtagacgagtcgaagggtcagggccggttgtggatcaggtct

S  E  D  A  G  V  I  C  S  A  S  Q  S  R  P  T  P  S  P  D  - cacttggccaacctcacatgcatcaacagcaggatctgaatccagtttggccctgaggct
1921   ---------+---------+---------+---------+---------+---------+ 1980
       gtgaaccggttggagtgtacgtagttgtcgtcctagacttaggtcaaaccgggactccga

T  W  P  T  S  H  A  S  T  A  G  S  E  S  S  L  A  L  R  L  - ggtgaatggaggtgacaggtgtcagggccgagtggaggtcctataccgaggctcctgggg
1981   ---------+---------+---------+---------+---------+---------+ 2040
       ccacttacctccactgtccacagtcccggctcacctccaggatatggctccgaggacccc

V  N  G  G  D  R  C  Q  G  R  V  E  V  L  Y  R  G  S  W  G  - caccgtgtgtgatgactactgggacaccaatgatgccaatgtggtttgcaggcagctggg
2041   ---------+---------+---------+---------+---------+---------+ 2100
       gtggcacacactactgatgaccctgtggttactacggttacaccaaacgtccgtcgaccc

T  V  C  D  D  Y  W  D  T  N  D  A  N  V  V  C  R  Q  L  G  - ctgtggctgggccatgtcagccccaggaaatgcccggtttggccagggttcaggacccat
2101   ---------+---------+---------+---------+---------+---------+ 2160
       gacaccgacccggtacagtcggggtcctttacgggccaaaccggtcccaagtcctgggta

C  G  W  A  M  S  A  P  G  N  A  R  F  G  Q  G  S  G  P  I  - tgtcctggatgatgtgcgctgctcaggacatgagtcctatctgtggagctgccccacaa
2161   ---------+---------+---------+---------+---------+---------+ 2220
       acaggacctactacacgcgacgagtcctgtactcaggatagacacctcgacggggtgtt

V  L  D  D  V  R  C  S  G  H  E  S  Y  L  W  S  C  P  H  N  - tggctggctctcccacaactgtggccatcatgaagacgctggtgtcatctgctcagcttc
2221   ---------+---------+---------+---------+---------+---------+ 2280
       accgaccgagagggtgttgacaccggtagtacttctgcgaccacagtagacgagtcgaag
```

FIG. 2E

```
           G   W   L   S   H   N   C   G   H   H   E   D   A   G   V   I   C   S   A   S   -
       ccagtcccagccgacacccagcccagacacttggccaacctcacatgcatcaacagcagg
2281   ---------+---------+---------+---------+---------+---------+   2340
       ggtcagggtcggctgtgggtcgggtctgtgaaccggttggagtgtacgtagttgtcgtcc Q   S   Q   P   T   P   S   P   D   T   W   P   T   S   H   A   S   T   A   G   -
       atctgaatccagtttggccctgaggctggtgaatggaggtgacaggtgtcagggccgagt
2341   ---------+---------+---------+---------+---------+---------+   2400
       tagacttaggtcaaaccgggactccgaccacttacctccactgtccacagtcccggctca S   E   S   S   L   A   L   R   L   V   N   G   G   D   R   C   Q   G   R   V   -
       ggaggtcctataccgaggctcctggggcaccgtgtgtgatgactactgggacaccaatga
2401   ---------+---------+---------+---------+---------+---------+   2460
       cctccaggatatggctccgaggaccccgtggcacacactactgatgaccctgtggttact E   V   L   Y   R   G   S   W   G   T   V   C   D   D   Y   W   D   T   N   D   -
       tgccaatgtggtttgcaggcagctgggctgtggctgggccacgtcagcccaggaaatgc
2461   ---------+---------+---------+---------+---------+---------+   2520
       acggttacaccaaacgtccgtcgacccgacaccgacccggtgcagtcggggtcctttacg A   N   V   V   C   R   Q   L   G   C   G   W   A   T   S   A   P   G   N   A   -
       ccggtttggccagggttcaggacccattgtcctggatgatgtgcgctgctcaggacatga
2521   ---------+---------+---------+---------+---------+---------+   2580
       ggccaaaccggtcccaagtcctgggtaacaggacctactacacgcgacgagtcctgtact R   F   G   Q   G   S   G   P   I   V   L   D   D   V   R   C   S   G   H   E   -
       gtcctatctgtggagctgcccccacaatggctggctctcccacaactgtggccatcatga
2581   ---------+---------+---------+---------+---------+---------+   2640
       caggatagacacctcgacggggtgttaccgaccgagagggtgttgacaccggtagtact S   Y   L   W   S   C   P   H   N   G   W   L   S   H   N   C   G   H   H   E   -
       agacgctggtgtcatctgctcagcttcccagtcccagccgacacccagcccagacacttg
2641   ---------+---------+---------+---------+---------+---------+   2700
       tctgcgaccacagtagacgagtcgaagggtcagggtcggctgtgggtcgggtctgtgaac D   A   G   V   I   C   S   A   S   Q   S   Q   P   T   P   S   P   D   T   W   -
       gccaacctctcgtgcatcaacagcaggatctgaatccactttggccctgagactggtgaa
2701   ---------+---------+---------+---------+---------+---------+   2760
       cggttggagagcacgtagttgtcgtcctagacttaggtgaaaccgggactctgaccactt P   T   S   R   A   S   T   A   G   S   E   S   T   L   A   L   R   L   V   N   -
       tggaggtgacaggtgtcgaggccgagtggaggtcctataccaaggctcctggggcaccgt
2761   ---------+---------+---------+---------+---------+---------+   2820
       acctccactgtccacagctccggctcacctccaggatatggttccgaggacccgtggca G   G   D   R   C   R   G   R   V   E   V   L   Y   Q   G   S   W   G   T   V   -
       gtgtgatgactactgggacaccaatgatgccaacgtggtctgcaggcagctgggctgtgg
2821   ---------+---------+---------+---------+---------+---------+   2880
```

FIG. 2F

```
         cacactactgatgaccctgtggttactacggttgcaccagacgtccgtcgacccgacacc

C   D   D   Y   W   D   T   N   D   A   N   V   V   C   R   Q   L   G   C   G   - ctgggccatgtcagccccaggaaatgcccagtttggccagggctcaggacccattgtcct
2881     ---------+---------+---------+---------+---------+---------+   2940
         gacccggtacagtcggggtcctttacgggtcaaaccggtcccgagtcctgggtaacagga W   A   M   S   A   P   G   N   A   Q   F   G   Q   G   S   G   P   I   V   L   - ggatgatgtgcgctgctcaggacacgagtcttacctgtggagctgccccacaatggctg
2941     ---------+---------+---------+---------+---------+---------+   3000
         cctactacacgcgacgagtcctgtgctcagaatggacacctcgacggggtgttaccgac D   D   V   R   C   S   G   H   E   S   Y   L   W   S   C   P   H   N   G   W   - gctctcccacaactgtggccatcatgaagatgctggtgtcatctgctcagctgctcagtc
3001     ---------+---------+---------+---------+---------+---------+   3060
         cgagagggtgttgacaccggtagtacttctacgaccacagtagacgagtcgacgagtcag L   S   H   N   C   G   H   H   E   D   A   G   V   I   C   S   A   A   Q   S   - ccagtcaacgcccaggccagatacttggctgaccaccaacttaccggcattgacagtagg
3061     ---------+---------+---------+---------+---------+---------+   3120
         ggtcagttgcgggtccggtctatgaaccgactggtggttgaatggccgtaactgtcatcc Q   S   T   P   R   P   D   T   W   L   T   T   N   L   P   A   L   T   V   G   - atctgaatccagtttggctctgaggctggtgaatggaggtgacaggtgtcgaggccgagt
3121     ---------+---------+---------+---------+---------+---------+   3180
         tagacttaggtcaaaccgagactccgaccacttacctccactgtccacagctccggctca S   E   S   S   L   A   L   R   L   V   N   G   G   D   R   C   R   G   R   V   - ggaggtcctgtatcgaggctcctggggaaccgtgtgtgatgacagctgggacaccaatga
3181     ---------+---------+---------+---------+---------+---------+   3240
         cctccaggacatagctccgaggacccct tggcacacactactgtcgaccctgtggttact E   V   L   Y   R   G   S   W   G   T   V   C   D   D   S   W   D   T   N   D   - tgccaatgtggtctgcaggcagctgggctgtggctgggccatgtcggccccaggaaatgc
3241     ---------+---------+---------+---------+---------+---------+   3300
         acggttacaccagacgtccgtcgacccgacaccgacccggtacagccggggtcctttacg A   N   V   V   C   R   Q   L   G   C   G   W   A   M   S   A   P   G   N   A   - ccggtttggccagggctcaggacccattgtcctggatgatgtgcgctgctcagggaatga
3301     ---------+---------+---------+---------+---------+---------+   3360
         ggccaaaccggtcccgagtcctgggtaacaggacctactacacgcgacgagtcccttact R   F   G   Q   G   S   G   P   I   V   L   D   D   V   R   C   S   G   N   E   - gtcctacctgtggagctgccccacaaaggctggctcacccacaactgtggccatcacga
3361     ---------+---------+---------+---------+---------+---------+   3420
         caggatggacacctcgacggggtgttccgaccgagtgggtgttgacaccggtagtgct S   Y   L   W   S   C   P   H   K   G   W   L   T   H   N   C   G   H   H   E   - agacgctggtgtcatctgctcagccacccaaataaattctactacgacagattggtggca
```

FIG. 2G

```
3421 ---------+---------+---------+---------+---------+---------+ 3480
     tctgcgaccacagtagacgagtcggtgggtttatttaagatgatgctgtctaaccaccgt D   A   G   V   I   C   S   A   T   Q   I   N   S   T   T   T   D   W   W   H   - tccaacaactacaaccactgcaagaccctcttcaaattgtggtggcttcttattctatgc
3481 ---------+---------+---------+---------+---------+---------+ 3540
     aggttgttgatgttggtgacgttctgggagaagtttaacaccaccgaagaataagatacg

P   T   T   T   T   A   R   P   S   S   N   C   G   G   F   L   F   Y   A   - cagtgggacattctccagcccatcctaccctgcatactaccccaacaatgctaagtgtgt
3541 ---------+---------+---------+---------+---------+---------+ 3600
     gtcaccctgtaagaggtcgggtaggatgggacgtatgatggggttgttacgattcacaca S   G   T   F   S   S   P   S   Y   P   A   Y   Y   P   N   N   A   K   C   V   - ttgggaaatagaagtgaattctggttatcgcataaacctgggcttcagtaatctgaaatt
3601 ---------+---------+---------+---------+---------+---------+ 3660
     aacccttatcttcacttaagaccaatagcgtatttggacccgaagtcattagactttaa W   E   I   E   V   N   S   G   Y   R   I   N   L   G   F   S   N   L   K   L   - ggaggcacaccataactgcagttttgattatgttgaaatctttgatggatcattgaatag
3661 ---------+---------+---------+---------+---------+---------+ 3720
     cctccgtgtggtattgacgtcaaaactaatacaactttagaaactacctagtaacttatc E   A   H   H   N   C   S   F   D   Y   V   E   I   F   D   G   S   L   N   S   - cagtctcctgctggggaaaatctgtaatgataccaggcaaatatttacatcttcttacaa
3721 ---------+---------+---------+---------+---------+---------+ 3780
     gtcagaggacgaccccttttagacattactatggtccgtttataaatgtagaagaatgtt

S   L   L   G   K   I   C   N   D   T   R   Q   I   F   T   S   S   Y   N   - ccgaatgaccattcactttcgaagtgacatcagtttccaaaacactggcttttggcttg
3781 ---------+---------+---------+---------+---------+---------+ 3840
     ggcttactggtaagtgaaagcttcactgtagtcaaaggttttgtgaccgaaaaaccgaac R   M   T   I   H   F   R   S   D   I   S   F   Q   N   T   G   F   L   A   W   - gtataactccttcccaagcgatgccaccttgaggttggtcaatttaaattcatcctatgg
3841 ---------+---------+---------+---------+---------+---------+ 3900
     catattgaggaagggttcgctacggtggaactccaaccagttaaatttaagtaggatacc Y   N   S   F   P   S   D   A   T   L   R   L   V   N   L   N   S   S   Y   G   - tctatgtgccgggcgtgtagaaatttaccatggtggcacctggggggacagtttgtgatga
3901 ---------+---------+---------+---------+---------+---------+ 3960
     agatacacggcccgcacatctttaaatggtaccaccgtggacccctgtcaaacactact L   C   A   G   R   V   E   I   Y   H   G   G   T   W   G   T   V   C   D   D   - ctcctggaccattcaggaagctgaggtggtctgcagacagctagggtgtggacgtgcagt
3961 ---------+---------+---------+---------+---------+---------+ 4020
     gaggacctggtaagtccttcgactccaccagacgtctgtcgatcccacacctgcacgtca S   W   T   I   Q   E   A   E   V   V   C   R   Q   L   G   C   G   R   A   V   -
```

FIG. 2H

```
      ttcagcccttggaaatgcatattttggctctggctctggccccatcaccctggacgatgt
4021  ---------+---------+---------+---------+---------+---------+ 4080
      aagtcgggaacctttacgtataaaaccgagaccgagaccggggtagtgggacctgctaca S   A   L   G   N   A   Y   F   G   S   G   S   G   P   I   T   L   D   D   V   - agagtgctcagggacggaatccactctctggcagtgccggaaccgaggctggttctccca
4081  ---------+---------+---------+---------+---------+---------+ 4140
      tctcacgagtccctgccttaggtgagagaccgtcacggccttggctccgaccaagagggt E   C   S   G   T   E   S   T   L   W   Q   C   R   N   R   G   W   F   S   H   - caactgtaatcatcgtgaagatgctggtgtcatctgctcaggaaaccatctatcgacacc
4141  ---------+---------+---------+---------+---------+---------+ 4200
      gttgacattagtagcacttctacgaccacagtagacgagtcctttggtagatagctgtgg N   C   N   H   R   E   D   A   G   V   I   C   S   G   N   H   L   S   T   P   - tgctccttttctcaacatcaccgtccaaacacagattattcctgcggaggcttcctatc
4201  ---------+---------+---------+---------+---------+---------+ 4260
      acgaggaaaagagttgtagtgggcaggtttgtgtctaataaggacgcctccgaaggatag A   P   F   L   N   I   T   R   P   N   T   D   Y   S   C   G   G   F   L   S   - ccaaccatcaggggacttttccagcccattctatcccgggaactatccaaacaatgccaa
4261  ---------+---------+---------+---------+---------+---------+ 4320
      ggttggtagtcccctgaaaaggtcgggtaagatagggcccttgataggtttgttacggtt Q   P   S   G   D   F   S   S   P   F   Y   P   G   N   Y   P   N   N   A   K   - gtgtgtgtgggacattgaggtgcaaaacaactaccgtgtgactgtgatcttcagagatgt
4321  ---------+---------+---------+---------+---------+---------+ 4380
      cacacacaccctgtaactccacgttttgttgatggcacactgacactagaagtctctaca C   V   W   D   I   E   V   Q   N   N   Y   R   V   T   V   I   F   R   D   V   - ccagcttgaaggtggctgcaactatgattatattgaagttttcgatggcccctaccgcag
4381  ---------+---------+---------+---------+---------+---------+ 4440
      ggtcgaacttccaccgacgttgatactaatataacttcaaaagctaccggggatggcgtc Q   L   E   G   G   C   N   Y   D   Y   I   E   V   F   D   G   P   Y   R   S   - ttcccctctcattgctcgagtttgtgatggggccagaggctccttcacttcttcctccaa
4441  ---------+---------+---------+---------+---------+---------+ 4500
      aaggggagagtaacgagctcaaacactaccccggtctccgaggaagtgaagaaggaggtt S   P   L   I   A   R   V   C   D   G   A   R   G   S   F   T   S   S   S   N   - cttcatgtccattcgcttcatcagtgaccacagcatcacaaggagagggttccgggctga
4501  ---------+---------+---------+---------+---------+---------+ 4560
      gaagtacaggtaagcgaagtagtcactggtgtcgtagtgttcctctcccaaggcccgact F   M   S   I   R   F   I   S   D   H   S   I   T   R   R   G   F   R   A   E   - gtactactccagtccctccaatgacagcaccaacctgctctgtctgccaaatcacatgca
4561  ---------+---------+---------+---------+---------+---------+ 4620
      catgatgaggtcagggaggttactgtcgtggttggacgagacagacggtttagtgtacgt Y   Y   S   S   P   S   N   D   S   T   N   L   L   C   L   P   N   H   M   Q   -
```

FIG. 2I

```
         agccagtgtgagcaggagctatctccaatccttgggcttttctgccagtgaccttgtcat
4621     ---------+---------+---------+---------+---------+---------+  4680
         tcggtcacactcgtcctcgatagaggttaggaacccgaaaagacggtcactggaacagta

A   S   V   S   R   S   Y   L   Q   S   L   G   F   S   A   S   D   L   V   I  - ttccacctggaatggatactacgagtgtcggccccagataacgccgaacctggtgatatt
4681     ---------+---------+---------+---------+---------+---------+  4740
         aaggtggaccttacctatgatgctcacagccggggtctattgcggcttggaccactataa

S   T   W   N   G   Y   Y   E   C   R   P   Q   I   T   P   N   L   V   I   F  - cacaattccctactcaggctgcggcaccttcaagcaggcagacaatgacaccatcgacta
4741     ---------+---------+---------+---------+---------+---------+  4800
         gtgttaagggatgagtccgacgccgtggaagttcgtccgtctgttactgtggtagctgat

T   I   P   Y   S   G   C   G   T   F   K   Q   A   D   N   D   T   I   D   Y  - ttccaacttcctcacagcagctgtctcaggtggcatcatcaagaggaggacagacctccg
4801     ---------+---------+---------+---------+---------+---------+  4860
         aaggttgaaggagtgtcgtcgacagagtccaccgtagtagttctcctcctgtctggaggc

S   N   F   L   T   A   A   V   S   G   G   I   I   K   R   R   T   D   L   R  - tattcacgtcagctgcagaatgcttcagaacacctgggtcgacaccatgtacattgctaa
4861     ---------+---------+---------+---------+---------+---------+  4920
         ataagtgcagtcgacgtcttacgaagtcttgtggacccagctgtggtacatgtaacgatt

I   H   V   S   C   R   M   L   Q   N   T   W   V   D   T   M   Y   I   A   N  - tgacaccatccacgttgctaataacaccatccaggtcgaggaagtccagtatggcaattt
4921     ---------+---------+---------+---------+---------+---------+  4980
         actgtggtaggtgcaacgattattgtggtaggtccagctccttcaggtcataccgttaaa

D   T   I   H   V   A   N   N   T   I   Q   V   E   E   V   Q   Y   G   N   F  - tgacgtgaacatttccttttatacttcctcatctttcttgtatcctgtgaccagccgccc
4981     ---------+---------+---------+---------+---------+---------+  5040
         actgcacttgtaaaggaaaatatgaaggagtagaaagaacataggacactggtcggcggg

D   V   N   I   S   F   Y   T   S   S   S   F   L   Y   P   V   T   S   R   P  - ttactacgtggacctgaaccaggacttgtacgttcaggctgaaatcctccattctgatgc
5041     ---------+---------+---------+---------+---------+---------+  5100
         aatgatgcacctggacttggtcctgaacatgcaagtccgactttaggaggtaagactacg

Y   Y   V   D   L   N   Q   D   L   Y   V   Q   A   E   I   L   H   S   D   A  - tgtactgaccttgtttgtggacacctgcgtggcatcaccatactccaatgacttcacgtc
5101     ---------+---------+---------+---------+---------+---------+  5160
         acatgactggaacaaacacctgtggacgcaccgtagtggtatgaggttactgaagtgcag

V   L   T   L   F   V   D   T   C   V   A   S   P   Y   S   N   D   F   T   S  - tttgacttatgatctaatccggagtggatgcgtgagggatgacacctacggaccctactc
5161     ---------+---------+---------+---------+---------+---------+  5220
         aaactgaatactagattaggcctcacctacgcactccctactgtggatgcctgggatgag
```

FIG. 2J

```
          L   T   Y   D   L   I   R   S   G   C   V   R   D   D   T   Y   G   P   Y   S   -
     ctcgccgtctcttcgcattgcccgcttccggttcagggccttccacttcctgaaccgctt
5221 ---------+---------+---------+---------+---------+---------+ 5280
     gagcggcagagaagcgtaacgggcgaaggccaagtcccggaaggtgaaggacttggcgaa S   P   S   L   R   I   A   R   F   R   F   R   A   F   H   F   L   N   R   F   -
     cccctccgtgtacctgcgttgtaaaatggtggtgtgcagagcgtatgacccctcttcccg
5281 ---------+---------+---------+---------+---------+---------+ 5340
     ggggaggcacatggacgcaacattttaccaccacacgtctcgcatactggggagaagggc P   S   V   Y   L   R   C   K   M   V   V   C   R   A   Y   D   P   S   S   R   -
     ctgctaccgaggctgtgtgttgaggtcgaagagggatgtgggctcctaccaggaaaaggt
5341 ---------+---------+---------+---------+---------+---------+ 5400
     gacgatggctccgacacacaactccagcttctccctacacccgaggatggtccttttcca C   Y   R   G   C   V   L   R   S   K   R   D   V   G   S   Y   Q   E   K   V   -
     ggacgtcgtcctgggtcccatccagctgcagaccccccacgccgagaagaggagcctcg
5401 ---------+---------+---------+---------+---------+---------+ 5460
     cctgcagcaggacccagggtaggtcgacgtctgggggggtgcggctcttctcctcggagc D   V   V   L   G   P   I   Q   L   Q   T   P   P   R   R   E   E   E   P   R   -
     gtaggtggtcgctctcagaccccactgtccaccggggcgcagacccctgactcggggact
5461 ---------+---------+---------+---------+---------+---------+ 5520
     catccaccagcgagagtctggggtgacaggtggccccgcgtctggggactgagcccctga tgggatgttcctcttggtgtcatattccaactcagattgagccctacattgtgctgcacc
5521 ---------+---------+---------+---------+---------+---------+ 5580
     accctacaaggagaaccacagtataaggttgagtctaactcgggatgtaacacgacgtgg tggtcatacggagttgaatcagacctggttcccgcctcccccaaggctcatggtccttgg
5581 ---------+---------+---------+---------+---------+---------+ 5640
     accagtatgcctcaacttagtctggaccaagggcggagggggttccgagtaccaggaacc aggacccgttgcagggcgaggtcaagagagttctgacctggatggcccatagacctgacg
5641 ---------+---------+---------+---------+---------+---------+ 5700
     tcctgggcaacgtcccgctccagttctctcaagactggacctaccgggtatctggactgc tcccagaatccatgcttctcatctgcaaaatgaaaatgtcaatacttacttcttagcact
5701 ---------+---------+---------+---------+---------+---------+ 5760
     agggtcttaggtacgaagagtagacgttttactttttacagttatgaatgaagaatcgtga gttgagagggttacttacataaaggaatttttggtgaaactgc
5761 ---------+---------+---------+---------+--- 5802
     caactctcccaatgaatgtatttccttaaaaccactttgacg
```

FIG. 5A - 1

| FIG. 5A-1 | FIG. 5A-2 | FIG. 5A-3 |

FIG. 5A

Sequence SC1 agtattcttaccatcatctttccctgctgtgctcccggcagacaattctaatctgtcatg
acactctgatgatcccagacccagctgcattatcattctcagtccaacactccaggaacc
aagggatcacaatccccttctaagaggaatccagcatgtgcctggtcttgggcattccct
ggtaggtgagtaaccctgttctctcgtcacccagtgcttatcagttgctgatctggcagt
aggaggatgaaacacagtgagcctattctgtgttcctattctactcaaggggtgaagagg
cacctggaaacaacaggaagagttgtaggattaaaaaggacatccaagattgaatgtaac
tttcatctggatgaagccaaaggcagacttccagccctaaattctgactggtggctgaca
caggacatgggttcatggtacccttctagaatgcagcatagactactgatgaacagtgca
tggcaaagaagccaagtgtcatttcatggcctcagcctctcagctgagaagcagggcaca
gctcacccaggctaggaaaacagaggcaagtcctggaaagctgtctgcttttaaccaaga
gttactggccatcaagtgtcttggttaaaaataagtgtcaggcaaccttcttggtagat
agagtgtgttggggcgattatcagagtctggtaatgacttctgagggtcccaaagagtg
aagtgatatttacatagcaaatccaaggaggggattgtgtgcaatataggtggaggtgg
gggcaggttttgtgggtttgccaagctccaagggtcatacaatgtgcatgtcaaggacaa
gaaatcaaagccatgtgaaatggttggaggtggttcagtttgaggtcatgtgtttctcag
ctcctgttgtggaattagtgtgagacccagaagactgtggccaaagctattatggaccca
tggtctctgtggactcatccctcatgccttctgctctctgatcacatccacactcatgtc
atcctcgttcttccaaggtgaggttactagcactgcacaggggctgatgagagcatgtcc
tgccaggaaaaaccatcccaaagagatgctttcccccttggcactgtgtcctgtatttgc
tcagcagcccacatcctgttctgccccaaaccttggggcagacttcccacaggtgaattt
gaactccccaagattaaaatcaagcctgtattcaggaaacacttgggagtcctcgaggtt
caccgagagggaagttggaaattttcacttatgtcagtgcgtttgcagttgggcaacag
ccagattgttcatatggcaatcaatcaaacacacctaagttttttccacatattagccat
cgactgttagcaaaagccctcacttcctttatattgatttatagcagcagcagaaatata
ccaccctagaggacacacctccttttagctaggtacctataaatgtccaggattttctat
tcaattgagaagaacccagcaaaatggggatctccacagtcatccttgaaatgtgtcttt
tatggggacaagttctatctacaggtattacgtttaattattatattcattaatttctct
cctgcagacccaatcatggcaaattatatctactactttccattacaagggaagttttat
atcaaagagtgggtagcactttgctgataattgtaattgtttgcaggtattcaggaggaa
tggctcttttttgttttatttctggctgagaaatataaatggttgtagttagaaaaagcc
agtcattaagtcaatgttttcagtaagtcattcaactaaaggaatgattgatttgtctta
gaaaaatccctgaagtttaggaaaggtggatgtgtattattaagaggcccttaaactttg
cagcaattggttaaacacacagtttgtgtgctatgaaaacggacagaaaggattcccact
gcaaatgccctttatgtggcttctttctacaggtgtgtctggcttgatggctaatatttg
ccgagcaaaatcaggtcaagtaattgagcgcagacaagatcattaagattccaagtttgt
cttggaattccaagtttgtctgtcatgcacagctttaaacaaacacttgaagcccagtca
ctcaagcatagctgtatgttcttagagagtcagatgataaacgtgagagagccgtcggta
gcgcactctgattgctgcatctcaatggcattttgcagagatactagaggaacaagtgat
tctcagtttgcctattctgtctctctcttcctctctctctgcctctctctctctctctct
ctctctatctttctctcttatctattgtgtagttattatcatctttctctcccctctct
ctccctctgtttctgtctgtctgtgtttctctctctctgtatctttctcttttccca
tcttttgggcagatatcacctttcttcctcctcctccctctgtttctgtctctgccttt
ctctccctgccccctcactgtatcttcctgtctttctcatctatcaggcagttattacc
tttcctccctccctcctcccccttctctgtttctctctccatctctctttctctttattg
ggcagctattatcacctttctctctgtctctgtctctgtctctcttttctcttcaactatt
gggcaactattatcacctctcctctctctctatctgtttctcttcatctgtcaggcag
ctattatcaccttccctcccctctcttttctctctcactctttctcatcatctattgg

FIG. 5A - 2

```
gcagctcttatcacttttcctccctatttctctctctctctctcccttttgtttctatctt
ctttctaccttccttccatccctttttctttctctccctctctttattcatttctttctt
ccttcttctcttttatctttcctactgccttttttttcttttatgtcaccttttgctaga
tttatgaatttcaggatacagggtaaaaatcacctaattttcaggtaacttccggaactc
tcactctcccccctaggctcagtgggggaagatttgaagattaaggttcatctggttggtt
gctttcatgaaagcagcacctcccaacccagccctcacacccgggtggtagggagcaggc
ccaccccctgtgatgagcgtgtggagggcctgggggccactaggcccaggacctcagggg
agtggagactgggcatcctcatcctgcctccatcagaagcatctgaaactggggaggctgc
gtcctcagccccagctcttgtcagtaccgagttcaccctccagattgtctctgaaccatg
acatggaattcacatcagccactgtagacagggagtgaattgccttgtctttatctacaa
agaaacaacaggcagcagtgctcttggattgaggacatttgtagtttgcccatgatgttt
tgtgcatgcatatggacagacatgcacatatgtgcatgcatgcctgtgtttgccattcag
aggtgggaattcatgctctctgaagtggacccgtattctcttatttaaatcttctaacat
tcctgaagttaggaacaattatttccacatttcagatggggaaactgaggctcagaaagg
ttattggcttgtccaaagacagcactggtgagtggctgggttagggcttgaatctggatc
aaattcactagcattcagatgacagctctggcccactggcccttgctgctccttgcaggg
aactgaggtgatgaactgaactgtggcatctaactcagtgcttggagcctgaccacagag
ctttgtgctggaagtaccgaggtggcaggcacctgtcagctctggtcttcatgcaaactc
ttgagaaaaactcagtatgcccaggtttgtgctgggcaggaaaggctgtggtacccactg
ctagccccagcaatgcccctcctctgccacttgcctgctgtggatcctctgtgaccctca
gtttactcatttataaatggaggttatgttccaacccatgcaatatctggcacatagaca
gagcctcagaaccatttagtgttactactctagacattttcctcatgttttatccaaaag
cagcttcctaaaagtaatgtgagctcttggattggatcctgcaacagaaaatgaaaaact
ggtgaaatccagataaagcctggagtaaacttagtaggaaggtaccagtgtttgttagca
tgagaatcacttgaactcaggaggcagaggttgccgtgagccgagattgtgccactgcac
tccagcctgggtgacagagtgagactctgtctcaaaaaaaaaaaaaaaaattaataaatc
attttccagaagtgattcttctcccttcaggcaatttaccaccattcccacaatggcagc
tggagtaacctacagctatgtggttgattcttggaagactacagattggtctcagtatgt
gcagaagggtctattcaaaatgtgtggacacagcagaaccaggaacaacttcaatgtggt
gttccatgctgtggatgagccttgtcaaggctctggctggatgagttcgactgccatggg
attaggcaggatacctgggacctggcagtgggaattgcatggtgtcaggtagactgtgtt
taaatggccgagttttgaatggaaggctctcttaggcacatctatcagctcgttcttgag
tgtgggagcagggatggcacgtcagaaaagaggtggggatgttctggtacagagttccct
agtttgctatctctgttgaaagaatgttgtggtttctattccgagtttcttcttcatttt
aagggatgcatagccacatggtttcagtggcccccttcctaagccatcaatatgaagcag
ggcagctgggggagcccatcgtggagctcatattcaggctgttgaggcaggtgaagatgt
tctctgacatatggcaagtcctgtcactggcctgttggttccattagagaaattcaaatc
tctgaactgtgactgtcactgctctcaggacccacatttacaaagaatctgaagagccgg
gcgtggtggcacatgcctgtagttccagctactctagggctggaggcaggaggcttgctt
gaacccaggaatttgaatctagcctgggcaatagagcaagactctatctctaaaagtaaa
ataataatctgataattttgtcaaatgccttaatcctccttttaccaggaagtaaaaaga
aaaggaataatgaaagtatgctggaattgttaataagaatttaaacatagcagacctttt
tatatcacatacattttggtatataaacatcataaaagacaaaagaataccatcacaggt
attttttttttttagcaaaataagatggttgaagttcttgttgcaaaatatcatgtgat
gaaatccctatcgaagtgtgtaagagtaccgtattttattttgtccttagaattgtatc
attgaccctggattcttgaatttgagaaattcatctaggatatcaccatctgaagactca
tagtctgagatttctgttgtacaatcaattctaccattattagtatctggagtgctatat
cttgtctctatattcctcttctggttcatctaattattgcaaaacatcttctcttgtca
gttttcttctctttgccatcacaagtagaaaatgaaaaatttgaattcttaactgcatt
caatgaaagctaaaaacagactatgaagaaagtgtctccagtcttaaaaaaaatcttct
tgaaagataatacaatactttgggcatggaagaattatgacttatttcactagttcatct
tccttctaggcaacttcaccattctaccattttcttactatttaataattgatgaataat
gatgcaatactttcttggatgatgaaatagtgaaatgcttcaagacataggaaaaataaa
atcagaagccaataatgaatcttggatttataaaggatctaatggatccatatggtgat
tacaagataggatgagtttttatccttttttttttaaatgaataaatactctctctgatctttt
```

FIG. 5A - 3

```
gaaagacctctaaaatatataaaagttgtgaaatatcaacactcacgagtatagttagaa
ctgctcaaaaagaaactcaaaagctacagttgagtccgatggaccttgtctggcctcact
gaatataaagatccagggatctctagatttccatttgcttcaagatggaataaaatattt
tcaggttatgagtcagaaggaacagaatatctgacattaacatatttcttctttagggg
tcatctgagtggctgttgcagctatactcaaatttcagactggacaaccagcttaagctg
tcttctcttgtccagcccttctttccaagcatagattacatcctgtcaccataagctgta
gtgttagggcctagtaaagagacatatgcttcattacatctaaaatgattgagctcctc
atatccaatccacttgctttaatccgctattgcagaattcatttagcaagaacgtcgggg
acacacaaacccaagattgagccacagcgccctctggtgtgattgtacggtgaagcgaaa
gccaatttctgtgacttgtaggaaatcatttctaaacagtgtttctaagacgaatttgtg
ttctttccaggtgggtggatcccaaggactacagactacggtaagaccttttcttcactc
ctcttccctggtggggttggccagttctcctctgctgctgttggctagttgaggctgagc
acagctgaggtcacagagcaaacgcctgccttgtcgaacgcaggaatgccggggggacag
gagacgtgggtgccaagacctggggcatgtctcaagtgcccactcggccaatcccagctg
tcattctccttcctcttgctctctgactctcagtcatttatcagatgaggttagtttcag
tttggtgtgaggagagatagttgaaaataaaggttagtaccttttcttttttttctttt
cttttttcttttttttttgagacggagtcttgctcaccctgtcaccagactggagtgcag
tggtgcaatctcagctcactgcaacctccgcctcctgggttcaagcaattctcctgtctc
agcctccagagtagctgggactacaggtgcgcgccaccacgcccagctaattttttgtagt
tttagtagagatggggtttcaccatgttggccaggatggtcttgatctcttgacctcgtg
atccacccacctcggcctcccaaagtgctggggttacaggcatgagccactgcgcccgg
```

FIG. 5B - 1

| FIG. 5B-1 | FIG. 5B-2 | FIG. 5B-3 |
| --- | --- | --- |
| FIG. 5B-4 | FIG. 5B-5 | FIG. 5B-6 |
| FIG. 5B-7 | FIG. 5B-8 | FIG. 5B-9 |
| FIG. 5B-10 | | |

FIG. 5B

Sequence SC2

```
gtacacgtgtatgtgctctgcatttttacttgctttgctgtaagtgatggctgaatgacgt
ttggagggtaagtagtattgccccttttcatagacaatgaaggtcaagcggttatcttcc
tgtccttctgaagttggatgtggtggaggtaggcttcagtctcagcccctcagagcctgc
tgatgcaatcacttcagcagcatcacgacctggcctgggataccaaatatacatcttcct
aagtggcagtttctccctttttaaaatttgaggagggtgggagaacttcttgggacttaag
acataaatgtatatcaacatcagattgaggagggaacccaggcattctatttactggaaa
ttaagtgacaaataaaagatacttaacatgctcaatggaaaagagaacttcccctggacc
taacccagcaagtcccagtgctgatttcctttgttcacatagtgccaggatgtgtgcaga
caccaagaggttttttttaattcacaaagaaacctacaaggacactgtcccatggcgtgat
ccccaagaggagtttctggttaaactgtctacttcaagagcaactctgtcatttggagt
gtgggctggactgagcccatgccaccatgcctggggtgtgcccttggtaatccaaccacc
aagtgggactgggctccccaaggggcatcgtcctccatgcagccactttgtgagtggtt
tagttttgcattctggaaaggttggttttctttcgaaaccacctttttttctggttgaacc
accttctcaggtatatttcagtgatggtggatatttgtcatttgagggtgtgtttgagcc
atagaaaccgccagatgtcttttgacattcaatcttgtgactagcatggggttgtgaatg
gactgggtgacttttgaatagaggctgtggcagcagaggagatgggggtagggtaataa
gagtaaaggatgctcatgtggcatcctagcccagtctggggccagtacaatgacaaagcg
attggcacatggttggcttttagcaatggatggtgccgttaggacctgtgcttccagccc
ttgcttcagagctgagcaagccctggaccaacccctccccaagcgagggctacgatcaatg
agctcttcctttctccaccctgcaggttctctgattccctcagagtcaaccctggagtca
actgtagcagaaggtaacgtctactatggggatccctgtagactcattaccccctgca
cccctaggttaatctctgattcagatgaggtgcagagggcatagaaagtagggtgcttag
ctcccacgaggggcccttccacaaaaggcctcaggtctgaacaggtatatcttgcatcga
tcatgtctgagactgaggaggaatcaacttgaagacgcgtctccaaggagttctcagtgg
agccttttattctgtctctagagattctgttatctttgcttgttgctcactcctgtgttc
ctcacccagctgtgctcatcgtggccagcctagggttctggatctctggctacagggcc
ttgagggtcaggtgcctacctgctaacgtagccaaattgctaggacagcatccttgccct
tgcccttcttaagcctatattgtgccacccttgtttcttcttaacagagagaaatcac
aatccttcagctcatgggcatcagagctcatgtacttccccctggggtatctccagtgag
aaatctgggagacatagtcaatacatcctgggattctggcagcctgggctttgggaaggg
aagtcacttcccatttcccatgggaaatcttggccctaggagaagctcaaggacaacatt
ctcaccaaggcctctgcgctgcccagggttggcatgcagttgggaatgctgatggtacat
gcatcgggccctcctgttcctcaggtcgtctttcttctcccttctccctctggccca
tggggtgaggtctgacttaacctcttcctctttcctatgatgaaggacacagaagacact
tgaagtgagggtgagactggctttattctgacttagccatgtcccttcgcaagattccca
catttttcttatttgcagcagctataagaggagaatctgttccttcctcttgagtggtttc
ccctgaggtccctgttacatgttaaggaccacaccttggtgggacaagcccttttggtata
actggtccagccagggatggggagtgaggggggcagaggtatttggctgatctgcctgtcac
acaggactgcagataggacttacctggagttgctcttatcaggaactctagtgtcagctg
ggagtcacatttcttctagatctggagacctcacgtagcagcccagtggagagctcagac
agaagctgagtgctgtggctgcagtgggttaagggtaactctcagatcacttcctctcca
```

FIG. 5B - 2

```
agccccagcactcagtcagctcctgtaggtgccctggacaaattccagggctctggagca
attcaaaaacggagattccaagccagtatcttacttaaaggggaatattagaagcatttc
tgctaatgtgaaaaacaaggcaagtatgccctccatctccactgctgttcaatgttgtac
tggaggtagtagccaatgcaatgagagaagagaaatcaattagaggcctaagcatgggaa
aagttatttttgcatccctcttctggagttctgtataggttacatgtaggcacatcggaa
tcagagtgagtatgttggtacagaaatatttcctccccaagcagccctttagaatcaaag
aactcaatgctagacaggtttcttgactttcccaaatttacacagcaagacaatatccag
atcaggagtgatggctcctcagcagatccagtttactttcagcccatgagtgtcttcag
aggagacctaactttatattttctggtttttttggggggtgtggtggggtttgttttt
catcttctacaattggcaaaagcagagactaccactacaaatactgagtctactgttgtg
acaggtaatgagtaactttgaatcccttctgtaggtcatgttgccaactatatccatgg
gctttactgttactcaggaaaaattttagggaatgggatgggagggaatgttgtgagtac
acagtgaccttctggatcccagaggtcagctagagtgaagcttccttcattgcccatgtt
cctggaggtagggagaaatcagtcagaatatggtgtctccaagagcctgtgtgctttgga
agcagagaccagtgggatcagtctccagtccagagtgacagcccagctcccccatctcca
cagctctgtgctgacgcctaacaatcctggccctgaggaaggctataaggccaggaatatc
acgtgacaaatgtgctccaaaccaaccttagagctgcagatacacatcagagctcctccc
gggacatcttgatgttatcgtgctgctcttcagtgtggggtgttgtgtgtccctgtctg
agggaatcaggcagagcccatggtctgcttagagaagggtcatgtgtatctctaggtccc
ctccaggatgcagatcaggaggagccttttattctgctccagctgaagctctaaggcttg
ggtttgggccaagcagtcactgtcctcttccccatgaagaactctaaccttaaggcctgt
taaagcccagcccaattagagattctctcaaagatatctgcctatggggaagaccctgaa
tgccctgcaggccctgagaccttgtgcctcagtaggaatgtgcaagagaaattctgtgcc
ttcctctaggatctgattctggtttggccctgaggctggtgaatggagatggcaggtgtc
agggccgagtggagatcctataccgaggctcctggggcaccgtgtgtgatgacagctggg
acaccaatgatgccaacgtggtctgtaggcagctggttgtggctgggccatgtcagctc
caggaaatgcctggtttggccagggctcaggacccattgccctggatgatgtgcgctgct
caggacacgaatcctacctgtggagctgccccacaatggctggctctcccataactgtg
gccatggtgaagatgctggtgttatctgctcaggtaggcatccagatctctggagggttg
ggtgtggtggctcatgcctttaatccccacactttgggaggatgaggtaggcagattgct
tgagctcaggcgttcaagaccagctctaggcaagatggcaaaccccatctctattaaaaa
aagaaaatcacttgggcccattctggggacagactgtattcagagaatatagtaacaggt
ttctcactccagggcccccgcccaagtcttcctggttatctggtggctctggagtttag
ttggggcagttggcctgtgggtacaatgccacggtcagcacaaatccccaagctgcgagc
agtgccgcaacattggtttggaggtgactgaggcaccagtgttcagacacagggtccagc
atgctgacatcagaaatgatgagcttttattctgctccaggaacatccgcataactcat
acccccattttccccgaggctccttctcagggacagcacgttttggggatctggttggtg
aagccttccctccccttgaacactgtattaccttgagtgttgtcagccgctgacccagag
ggaaggatgcaattgtaaatagttcacttatgattgctgtgaagagaggcagggaagtgg
ggtaagggtgggaggatggcagtgagtcgcaaatggtgggctcacgagtgagctcagcat
agggagcaggggacctcctagagtatcaccaggaatccacgtcaaacctcagactcatc
gcagctcaagcgtggagagttagggtcttcatctactcattgcttagggtggctgtttgc
tgctccctgggtgttgataccgaggttgttgtggccggtcccaggcaccgaagtgacctt
catatccctggagagtgagccacaggcacagagaaggcaatgccaggggctgtggggtcc
ctgagggaccgagggcttcacggtgggcactggcagggcccacttggtgggcgtgtgatg
ggcatcagctcagggtgtagataccccaagtcacttcagccttaactctacttggagtca
ctgagtgtttggtgtctaatgttgctatttttttctcacagctgcccagcctcagtcaac
actcaggccaggtgagtccccagaatccttcctcgggatacccttctcttctgctcag
ttaccccttccctactccacagagccctcctgcttctctgcagatactctggggcatatt
atttcaccccaactctgtaactgagaccctagcatggggcttcttaaccacacatggga
tttagcttctgccttctcttcagtccatctcagctttcatcacacagttccatgctgtcc
caatgaacaactcttagaagttcagaagaagcctgctgtttaatgagctttggcctctt
tatattcagggctgacacaaccttctgggaattgagggtgagactctctaatgttctgt
tgaaggcaaggtcagtacaggcttgatacccccatctctcactacttgaaaaaccccag
attctgcagggccacgtctgcattcagaagaggcagaggccatgctgaggggagagagag
```

FIG. 5B - 3

```
gctaagaaatgtttctggtgccttcacttaccaggaaacctgatttcccccagggcggac
ccctagtatcccgaacattttagctgcaagtgtcaagtcttggcagtggtgtcagatgag
ccagtcagtccacgcgtcagtggatggtggggatggggtggtgaaggtttcctaactg
cgaataggtcatccctctctcagagagaggtggaagggcctgcatggtgtcctttgtccc
tgaatgagttccctgggcaggagacctgggcagacacatggggagcaagtggccagacct
tcgagtggaattgttttcacagtgcttgcctggtccagagaaccgcttgttttttacctt
tttcccttcaagtccaattgtatccttctctttgttgctgtttacagaaagttggcctg
tcaggatatcaccacctgtacccacagaaggtaaagaatcctctcaacactccctggggc
tcactttctacctctggatacactttggatttcatagttcacttatgattgccataaaga
gaggtggggaagtgggctaagcgtgggagggtggcagcaggtgataaacagttggctcaa
gagtcagctcggcactgggaacaagagcaggacctcccagaagatcattaagaatcatta
ggctcatgataggatgaggctcaaggtgggccccttgcttttcatgtttctgtgggttg
ggtagggaggaagctggagtctctgaaaacccagaattagatgtgatattggagggtgga
gggtgctggtgacctgtctcctgtgggatcctgttccaagtggtcagaaaagatcctat
ctatgggctcagaacaagccctgggggtctccctaatcctatggggacctcatccctgcc
atctctggtactctgccagtcagatcccagataggaccatgctcctgaataagggagggg
tctgggcctgccatctggagctgagcagctccatcctctgtgtacccaactggggagtgg
ggcatccattcccatcacatccactggggtcacaggtgcttccccaaaagttgagcatcc
atagacctgggcagagtaggttatcagtgctactttcacggtgatgaagcctagtctgtg
gtcatatgcaaaggtgactgcctgcctaggtgacttagttcattaggaagtaccctgagt
gtggaacttaccttagattcttgacctcatgatagggatggatgaagggttcttgtgttc
ccctgtaggatctgaatccagtttggccctgaggctggtgaatggaggcgacaggtgtcg
aggccgagtggaggtcctataccgaggctcctggggcaccgtgtgtgatgactactggga
caccaatgatgccaatgtggtctgcaggcagctgggctgtggctgggccatgtcagcccc
aggaaatgcccagtttggccagggctcaggacccattgtcctggatgatgtgcgctgctc
aggacacgagtcctacctgtggagctgccccacaatggctggctcacccacaactgtgg
ccatagtgaagacgctggtgtcatctgctcaggtgggccttcaagaacttgggctcactc
tcttggggtggagtttgctccaaaagaaactcctaattacattctgatctcctcactcaa
agcttctatgttttctatgtttctgaagacttgtcagctctctgctaagaatccatatgt
actcactgcctagtgttcctgtggtcacttaggacaggggatcaaactaaaacaacccag
agttttccccttcctgaggcaaggcaaggaagaggcagaagagaaaagtgccggctccc
cagggctccatttctcccctgctgagtagcacggtgtgagggtataatggatgcagcaca
gacagcaaggcaggggagggatcccctcactgcgaggaactctgaactaaagatgcttgg
ctaaaagtgggttctcagctgagacccagtgaggaggtctggaaatagaggctcaagggt
taggagtgcaaatgggtgtctgtttgtatcaggcctgggttgcgtggggttggagttctt
gacctcagctcttctcagaacgctgctgagcattgcctgtgttctaggtctggtgagggg
agggcagtccccatgaggccagccagacatggccttgtcattgcctgtgattggggcttg
aagatcgcacaagggattttggctggagtggcttcctcagccttgctgactcaggaacac
ctaagatgtgcaagggagtgggttggtttaggtcaaccgggttaccctgggcagacacaa
tttgatcacctcagagctggcaatagtggacaggatctgcctcgaccccttacacggtgc
atctctgtggggatgtgcatggcaatgtccctccctgtgtgataggaactaggatggact
gagtgtcagactcgctcatttcttccctcctcgttccagttttgccgacttctgtgtaa
tgttcctgatctgaccttctcttctctttctcacagctccccagtcccggccgacaccca
gcccaggtaggtccccagtgtccttcctcaaaatgtcccttctctttctgcccaatcacc
ccttccacactccacagagctctcctgtttctctgtgtggatactgtggggcatattatt
tccaccccaacaccggctgtgtaactgagatcccagcacagcgcttttaaacacacac
aggattgaggaggcctctgtcttcttttcaacccctctcagctttcatgaaacagtttca
tactgtcccagtggacaacccttacaggttcaggaagtggcccatgtttaatgagcttt
ggtccttttatattccggactcacatatagtttctgaaaattgagggtgtcaccctctga
cccgttcaaggcatcgtcagggcaggctcgatacccccatccatcactgctggaaacatt
ccgagattatgattccgagatttctatccagaagaggcagagtttgtgctcgggcaggga
gagggataataaaggtttgtgatgtctctgcttaaccagaaacctgattcctgattgtcc
cctgggcagcccctggttcccctaacattttacctggcagtgtccgagcttcagcaatgg
cgtctgatgtcctagtcagtccatgcatcagcagatgtgggatggcatggtggggcatc
ctctaacagatagaaagataccccaggattacagaaatggagggctcagtctggtctcca
```

FIG. 5B - 4

```
gcaggacctttgtccctggatgagttcacagcacaggagacctgggaagacacatgggaa
acaaatggcaggaacaagaagtggaattgttgtcacgttgattcctcctcccagagatcc
ttttgttctgtgccttttcccttcaagtctaattctgtcttttccttttgttgcaattta
cagatacttggccgacctcacatgcatcaacagcaggtaaataaccctctcacccctccc
taggactcactatctctggacatattttgtgtttgaaactgataggatgaggctcaatgt
gggcttctctgttttcatgtccctgtgggttgcgtgggaggaaggtggaatctctgagga
gccagtcctgggtctgatgtttgaggacggagggtgttggtgacctgtctcccatggaat
cctgttccaagtggtcaggaagatcctcatccaggtgctcaggacgagcactggagggc
tccttaatgctgctgggacctcattcctggccctcaggccatgggatccagacctctgaa
gagcgggtgaaagtgccggtccctgcacctgtgtggccaaggccttgccatcactggcaa
tttgccagaaggcagagaggcccatgcaggtgccaataagctcctgaatatggaggggt
ctaggcctgtcatttgtagctgtgtagctccatcctgtgttcacccagagtggggagtgg
ggtgtccattcctgtcctctcctctggggtcatacatgcttacccatagcttgagctttt
atagacttgagtagaatagggcatcacttttccactatgaccaagcttaacctctgggt
gcagccatctgccattgtgactgcgtgccctggtgactttggcatttgtattcaaacttg
actacttttcccattgccctgagtgttgtccatgcctttccttcacctcagaatggaga
tggatgaaggattcttgtgttccctgtaggacctgaatccagtttggccctgaggctgg
tgaatggaggtgacaggtgtcagggccgagtggaggtcctataccgaggctcctggggca
ccgtgtgtgatgatagctgggacaccagtgacgccaatgtggtctgccggcagctgggct
gtggctgggccacgtcagccccaggaaatgccggtttggccagggttcaggacccattg
tcctggatgacgtgcgctgctcaggctatgagtcctacctgtggagctgccccacaatg
gctggctctcccataactgtcagcacagtgaagacgctggtgtcatctgctcaggtgggc
ctccaagaccttgggctccctctcttggggtagattttgctcaggaagcgaggtctcatt
atgttctgatctcctcactcagagcttttcagcctttcctatatatctgatatctcctt
agctctctcctaggaaactgcatgagtcttcattgccaggttttgaggaggtcaggtagg
acaacgggccaaagtgaaataagggtcacgcctttgttcacctaccgaggcagcgcaagc
agagggagaagaggaaagtgccaggtctttgccttttagtgtggctggaaaggaatagct
ggggctggtttgttcatgaggaaagaggctgatttgggtcttggctttgcaggctgcata
ggaccatggtgcaggcgtctgctcagcttctgatgagggcctcgggctgcttgtactcct
agcagaaagggatggggaggtggcctgggcagaggtcacaaggtgagggaggaaggaaga
gagagcaagagggagggctcagactcttcaaccaccagctcttgctaggaactaagagaa
gaactcacccctgaccagggagggcactaagttattcatgcagtgttggtctccatgacc
cagacctggtgcatcaggcctcacctctaaacttggggattcagttgcaatataacactt
ggatgtgacaagcctctaaagtatagcaccctggctctccagggttccatctttcccta
ctgaaagattttgcaaagggttacatggatgaagcacatatagaggatggggagggact
gtctccctgggaggagcccagaaccacaggctcctgctaggaagcgcggtcttctgctga
ggcccaataaggtgatgtcttaatagagacacaaggctaggagtgcggatgtgtgtctgt
ccctctctggcctgagatttggggctgtgagtccttgaccacaactccctccagagcac
tgcagtgtcttgcctgtgcaccggtctggtgtggagtgtgcagtccccatgaggtctgct
aggcaaagcattgttatgaacgcctgtgggctggactggaacatcagaggcaggactttg
gctggagtggcctcctcacatttgctaactcagggactgctaagacatgcaagggagagg
gtaggttttgtgtcaacctgattactatgggcagacacaaggttaatcaccttggagttg
gcaatagtggacaggatctgcccagacaccctccaaggagcatctctgtggggacatgca
tggcaatgccctccctctgtgatggggacctagggtggactgaaggcatgatctgtttag
ttccttccacctttgttccgattttgccagcttctgtatagtgcatctgatctgacctcc
tctttctcacagctgcccactcctggtcgacgcccagtccaggtgagtccccagtgtcct
tccttgggatgtcccttctctttctgtataattatccctttctgcactccacagagccct
cgttcttctctgagtgaatactacatggcatacaattttcccctgctctgtaactgagac
cctggaatggcgcttctgaaccagacatagggttcaagaggcttctgtcttctgttccat
ttatctcagctttcatgaagcagtttcatactgtcccagtggccaacccttagaggttta
ggaagtggcctcatatttaaatagctttgaccctttctattcagagctgatatgacctt
cctgagaattgagagtgattgccaaagtctcctcggaagccaatgtcagctaaagcctta
aacatggctgccgccatgggcaagcaatgtcagtgcaggcctgacacctcccttcctcac
tccttccaacacccagattctgcagcgctacatgtgcatccagaagaggcataggccatg
ctcgggcagggagagggataataaatatttctggtgcctccacttactgggaaacttgat
```

FIG. 5B - 5

```
accccttttggtcagctccttggttttccctaacgttttagctcgagctagtagagtgtcag
caatggtgttagatgtacccgtcagtgcatgtgtcagtgcatggaacaggctaaccctttt
gtgactgagaagaggacatcccacacttcagaggcaggagggatcgaactggtctccagc
aaggcttatgtcccttgctgagcttgctgagctgcagacttgggcagacacatggggagc
aaagtggcaggaatcagaagtggggtagttttcatgatgctcgccttctccggagacttt
tcctttggagattttcaccatcaactttaattctagcctttgtctctgttgcaattaca
gacacgttgccgaccatcaccttacctgcatcgacagtaggtaaataatcctctcgcccc
tccctagggctcactctctacctctggacaaatgttttttctgaaatgataggatgagg
gtcaaggtgggcccctctgtttttcatgtccctgtggttgcatgggaggaaggtagagt
ctctggggacccagctgtgggtctgatgttggaggctggagggtgctggtgacttttctc
ccgtggaatcctgttccaagtggtcaggaaacatcctcatccaggtgccaaggaaaagcc
ctggaagcttccctaatcctactaagacctcattcctgtccctcagcccatgggctgcag
aggtgtgaagagtcagtgaaagtgagtgtccccacacctgtctggccaaggccttgtcat
acctgtgaaattttcagaagccagacaggaccataggattgccaccaagctcctgagatg
gggagagtctggcctgcctactgtagctgtgtagctccatcctgtgtgtgcccaggttag
ggaatggggtttccgttcctgttaactccagtagggtcacaggtgcttccccaaacttga
gccttcataaacccaggcagaactgcttctttgactttgatgaagctgaatctctggttt
tattcatattcaaaggtgactgcctgcccaggtgactttagccattaggacgtgccttga
gtgtggaacattccttagattcttgacctcatgatagggatggatgaagggttcttgttt
tcccctgtaggatctgaatccagtttggccctgaggctggtgaatggaggtgacaggtgt
cagggccgagtggaggtcctataccgaggctcctggggcaccgtgtgtgatgacagctgg
gacaccaatgatgccaatgtggtctgcaggcagctgggctgtggctgggccatgttggcc
ccaggaaatgcccggtttggtcagggctcaggacccattgtcctggatgacgtgcgctgc
tcagggaatgagtcctacttgtggagctgccccacaatggctggctctcccataactgt
ggccatagtgaagacgctggtgtcatctgctcaggtgggcctccaagacttttggtttcc
tctcttggggtagattttgctcaggaaggttttattatgttctaatctcctcacttagag
cttttcaacttttcctatatttctgatacctccttagctctctcctaggaaaccgcatg
agtcttcaccacattgccaggttttgaggaggtcagagaggacaatgggccaaagtgaaa
taagggtcacacctttgttcccctactgaggcagcgcaagcagagggagaagacgaaagc
gccgggtctttgccttttagtgtggctggaaaggaatagctggggccaggttgttcatga
agatagaggttgatttgggtcttgggtctttgcaggctgcataggagcatggtgcaggca
tctgctcggcttctgctgaggacctcaggctgcttgtactcctggcagaggggatgggga
gctggcctgggcagaggtcacatggcgagggatgaagcaagatggcagaagaagatgggg
aggtggcctggacagaggtcacatggtgagggaggaagcaagaaagagcaagagggaggg
cccagacagttttcaaccaccagctctttctaggaactaagagaagaacttacccctgac
cagggaggacactaagttattcatgaagagttggccttcatgacccagacatggcacatc
aagcctcacctctatacttggggatccaatcccaacatgagtcttagatgggacaaacat
ccaaactatagcatgctgcctctccagggttccacctttcccctactgaaaggtttaggt
gagggtgaggtggatgcagcacatataggcattgagggagggacggtctgactgggagga
ttccagaaccaagggctcatgctgggaagggagggttttctgctgaggactaataaggag
gcatcagaccggaaacacaaggctgggagtggagattcgtgactgtccatatctgacctg
ggttttgggggtgtgagtgcttgattgcaattccctccagagcactgcagtgtcttgcct
gtgcaccggtcaggtgtggggcaggcagtgcccatgaggcttactgagcaaagccttgtt
atgaatgcctgtgggctgggctagaagatcacaggctggatatttttttttgcaggagt
ggcctcttcatacttgctgactcagggactgctaagatgtgcaagggagtgggttggttt
tgtgtcaacctgattactatgggcagacacaaagtccttcaaacaccccagatgcagca
gggccccatctacatgcggaaaggcagaggccgtgctcaggcaaggagagagatattaga
tatttctggtacctccacttgccaggagactttatactcctttgggcagctccctgatcc
ttctaacattttagctgtaacaatcagaggctcagcaatggtgtcagatgtgtccattag
tccatgtgtcagtggatggggcaggcaaacccttgtagctgagaagaggatatcccaca
cttcagaggtaggagggattggactggtctccagcgaggcctatgtcccttcctgagctt
actggctgaagagttgggcagacacatggggagcaagtggcaaaaaccagaaatccagt
agttttcatgatgcttgccctatctggagacttttccttttggagcttttcaccctcaag
tttaattctagcctttgtctttgttgcaattaaagacacgttgccgaccaccacattacc
tgcatcaacagtaggtacagaatcttctcacccccactagggctcactctctacttctgg
```

FIG. 5B - 6

```
acaaatgttttttctgaaaatgagaggatgagggtcagggtgggtccctgtctttttca
tatccctgtgcattgagtgggaggaagttggagtctctggggagccagtcctgcttctgg
tgttggagggtagaggggctggtgacctgtctcccttgggatcctcttccaagtatcag
gaaataataaagaaaaaaaaaaagatcctcatccaggtgctgaggacaagccctggagg
gctccctactcctattcgacctcgttcctggccctccagccatgcactgcagacctgcaa
gggtgggtgacagtttctgtccctgcagctgtctggccaaagccttgccatccttggcaa
tttgccagaagccagggaggaccatggggtgccacctaactcttgaacatggggacagc
atggtcctgccctctggagctgtggagctccatcctgtgtgtgcccagagtagggagtcg
gttgtctattcctgtcacctccactggggtcacaggtgcttccccaaaacttgagccttc
ataaacccaaggagaatagtgtatcacctctccttctactgtgatgaagctgaacctctg
gttgcagtcatctttaatcgtgactgcctgcccaggtgactttggccattaggaagtgcc
ctgagtgtggaatgtgccttagatccttgacctgctgatagggattgatgaagggttctt
gtgttctcctataggacctgaatccagtttggccctgaggctggtgaatggaggtgacag
gtgtcagggccgagtggaggtcctataccgaggctcttggggcaccgtgtgtgatgacag
ctgggacaccaatgatgccaatgtggtctgcaggcagctgggctgtggctgggccacgtc
agccccaggaaatgcccggtttggtcagggctcaggacccattgtcctggatgatgtgcg
ctgctcaggacatgagtcctacctgtggagctgccccaacaatggctggctctcccacaa
ctgtggccatcatgaagatgctggtgtcatctgctcaggtgggcctccagcaattttggt
ttcctctcttggggtagattttgcccaggaagagaggtcttatgttctaatctcctcact
cagagcttttttcaacctttcctatgtttctgatatctccttagctctcttctaggaaact
gcatgagtcttcaccacagtgccaggttttgaggaggtcagagaggacaatgggccaaag
tgaaataagggtcatgcctttgttcccctaccaaggcagcgcaagcagagggagaagagg
aaagggctgggtctttgcatttagtgtggctggaaaggaatggctggggtcaggttatt
catgaagaaagaggcagatttgggtcttggctttgcaggctgcataggagcgtggtatct
gcttggcttctgctgacagcctcaggctgcttgtgctcctggcagaaggagatggggagg
tggcctgagcagaggtcacgtggcaagggaggaagcaagagagggcaagaaggaaggccc
aggctcttttcaaccaccagttcttgctagaaactaagagaagaactcacccctgatcag
ggagggcactaagttgttcatgaatggttggcttccatgacccagacatggcacatcagg
cctcacctctatacttggggatccaatcccaacatgagtcttgtatgggacaaacatcca
atctatagcacactggctctccaggttccatctttccccactgaaaggtttaggtgag
ggtgaggtggatggagcacatataggtgttgggggacggacgatctcaccgggaggagtc
cagaaccaaaggcttatgctgggaagggagggtcttccgctgaggcccagtaaggaggca
tcagactggaaacacaaggctgggagtgcagatctgtgtctgtccaagtctggcctgggt
tttgggggtgtgagtgcttgactgcaattccctccagagcactgcagcatcttgcctgta
caccagtcaggtgtagggcgggcagtgcccattagggctgctgagcaaagccttgttatg
aatgcctgtgggctgggctagaagatcacaggctggattttgctggagtggcctcttca
tacttgctgactcagggactgctaagacgtgtaagggagagggttggttttgtgtcaacc
tgattactgtgggtagacacaaacttaatcactttggagctggcagtagtggacaagatc
tgcccagatgcctttcaaggagcatctttgtggggacgtgcatggcaatgcccctccctc
tgtgatggggacatagggtggactgaaggcgctaccagtttagttccttgtacctttgtt
ctggttttgccagcttctgtatagtgcatctgatctgacctcctcttttctcacagctgcc
cagtcccggtcgacgcccaggccaggtgagtccccagtgtccttccttgggatgtcccttt
ttctttctgcacaattatcctttttcccattccacagagccctccttcttacctgtgtgg
atactgtgggtcatactattttccctgctctgtaactgagaccctagcatggagcttctt
aaccagacatggttaagaaggtatgatctttctaagaattgagagtgattgccaaagtct
cctgggaaggcaatttcagctaaagccttaaacatgcctgtccatgggcaagaatgtcag
tgcaggcctgatacctccattcctcactccttcagacaccccagatgcggcagggcccc
atctacctccagacaggcagaggctgtgctcaggcagggagagcgatattagatatttcc
gttgcctccacttgccaggagactttatactcccttaggcagctccctgatccttctaac
attttagtttcaagcgtgagaggctcagcattggtgtcagatgtgcccatcagtccatgt
gtcagtggatggggcaggtaaacccttgtagctgagaagagggtattccacacttcaga
ggcaggagggatcggactggtctccagtgaggactatgtccctggctgtgcttcctgagc
tacagacttgggcagacacatggggagcaagtggcaggaactagaaatggaagaatattc
atgatgcttgccttgtccagagacctttccttttggagcttttctccctcaactttaatt
ctagcctttgtctttgttgcaatttacagacacgttgtcgaccatcacgttacctccatc
```

FIG. 5B - 7

```
gacagtaggtaaataatcctctcacccctccctagggctcactctctacctctggacaaa
tgttttctctgaaaatgataggatgagggtcaaggtgggcccctgtcttttcacatccc
tgtgcgctgagtgggaggaagttgagtctctggggaaccagtcccgggtcgggtgttaga
gggtggagggtgttggtgacctatctcctgttggaccgtgttccaagtatcagtaaagat
cctcattcaggtgctggacaaaccctggagagctccctactcctgggacctcattcctgg
ccttctggccatgcattgcagacctgcaagggagggtgaaaatttctgtccctgcagttg
tctggccaatgtgttgccatccctggcaatttgccagaagccagagaggaccacgtgggt
gccaccaaactcttcgacatggggatagcataggcctgccctctggagcagtggagctcc
atcctgtgtgtgctcagagtagggagtggggtgtccattcctgtcacctccactggggtc
acaggcgctttcccaaaatctgagcctccataaacccaggcagaatagggtatcacctct
ccttccagtatgatgaagctgaacctctggttgcagtcgtattcaatcgtgactgcttgt
ccaggcgaccttggccattaggaagtaccctgagtgtggaacgtgccttagatccttacc
tcatggtagggatggataaagggttcttgtgttccctgtaggatctgaatccagtttga
ccctgaggctggtgaatggaagtgacaggtgtcagggccgagtagaggtcctataccgag
gctcctggggcaccgtgtgtgatgacagctgggataccaatgatgccaatgtggtctgca
ggcagctgggctgtggctgggccacgtcggccccaggaaatgcccggtttggccagggct
caggacccattgttctggatgatgtgcgctgctcaggacacgagtcctacctgtggagct
gcccccacaatggctggctctcccacaactgtggccatcatgaagatgctggtgtcatct
gctcaggtgggcctccaagaccttgggctccctctcctagactggagtttgctcaggaag
aaaatcctaattacattctgatctcctcactcaaagattcttctatgtttcctatattta
tgtagtcttgttagctctctgctaaggatctgtatgaattttactacagggcttggtgtt
cctgtggtcacttaggacaggccccaaactgaaacaacaacccagactttatccccttcc
tgaggcagtgcaagaaagaggccgaagagaaaactgctggctccccagggttccatttct
cctcagctgagtagcactgggtgagggtatcatggacataggacagacagcaaggtaggg
gaggaatcctctcactgagaggaactctgagctaaagatgcttgtctgaaagtgagttct
cagctgagacccagtgaggaggtctggaaatagaggctcaagggttaggagtgcaaatgg
gtgtctggttctatcaggcctgggttgtgtgaggttggagtccttgacctcaggtcctct
cagaacgctgcagagcactgccttgccctgggtctggtgtggggagggcagcccccatga
gacaggccaggcatggccttgttattgcctgtggtcggggcttgaagatcacacaaggga
ttttggctggagtggcttcctcagccttgctgactcaggaacacctaagatgtgcaaggg
agtgggttggtttaggtcaaccgggttaccctgggcagacacaatttgatcacctcagag
ctggcaatagtggaaggatctgcctcgaccccttacacggtgcatctctgtggggatgtg
catggcaatgtccctccctgtgtgataggaactaggatggactgagtgtcagactcgctc
atttcttccctcctcgttccagttttgccgacttctgtgtaatgttcctgatctgacct
tctcttctctttctcacagtttcccagtcccggccgacacccagtccaggtaggtcccca
gtgtccttcctcaaaatgtcccttctcttctgcccaatcaccccttccacactccacag
agctctcctgtttctctgtgtggatactgtggggcatattatttccaccccaacaccgg
ctgtgtaactgagaccccagcacagcgcttttaaacacacacaggattgaggaggcctc
tgtcttcttttcaaccctctcagctttcatgaaacagtttcatactgtcccagtggaca
accttacaggttcaggaagtggcccatgtttaatgagctttggtcctttatattccg
gactcacatatagtttctgaaaattgagggtgtcaccctctgacccgttcaaggcatcgt
cagggcaggctcgataccccatccatcactgctggaaacattccgagattatgattccg
agatttctatccagaagaggcagagtttgtgctcgggcagggagagggataataaaggtt
tgtgatgtctctgcttaaccagaaacctgattcctgattgtccctgggcagcccctggt
tccctaacattttacctggcagtgtccgagcctcagcaatggcgtctgatgtcctagtc
agtccatgcatcagcagatgtgggatggcatggtgggggcatcctctaacagatagaaag
atacccaggattagagaaatggagggctcagtctggtctccagcaggacctttgtccct
ggatgagttcacagcacaggagacctgggaagacacatgggaaacaaatggcaggaacaa
gaagtggaattgttgtcacgttgattcctcctcccagagatccttttgttctgtgcctttt
tcccttcaagtctaattctgtcttttccttttgttgcaatttacagatacttggccgacc
tcacatgcatcaacagcaggtaaataaccctctcacccctccctaggactcactatctct
ggacatattttgtgtttgaaactgataggatgaggctcaatgtgggcttctctgttttca
tgtccctgtgggttgcgtgggaggaaggtggaatctctgaggagccagtcctgggtctga
tgtttgaggacggagggtgttggtgacctgtctcccatggaatcctgttccaagtggtca
ggaaagatcctcatccaggtgctcaggacgagcactggagggctccttaatgctgctggg
```

FIG. 5B - 8

```
acctcattcctggccctcaggccatgggatccagacctctgaagagcgggtgaaagtgcc
ggtccctgcacctgtgtggccaaggccttgccatcactggcaatttgccagaaggcagag
aggcccatgcaggtgccaataagctcctgaatatggagggggtctaggcctgtcatttgt
agctgtgtagctccatcctgtgttcaccagagtggggagtggggtgtccattcctgtcc
tctcctctggggtcatacatgcttacccatagcttgagcttttatagacttgagtagaat
agggcatcacttttccactatgaccaagcttaacctctgggtgcagccatctgccattg
tgactgcgtgccctggtgacttacgtgccctggtgactttggcatttgtattcaacttg
actacttttcccattgccctgagtgttgtccatgccttttccttcacctcagaatggaga
tggatgaaggattcttgtgttccctgtaggatctgaatccagtttggccctgaggctgg
tgaatggaggtgacaggtgtcagggccgagtggaggtcctataccgaggctcctggggca
ccgtgtgtgatgatagctgggacaccagtgacgccaatgtggtctgccggcagctgggct
gtggctgggccacgtcagccccaggaaatgcccggtttggccagggttcaggacccattg
tcctggatgacgtgcgctgctcaggctatgagtcctacctgtggagctgcccccacaatg
gctggctctcccataactgtcagcacagtgaagacgctggtgtcatctgctcaggtgggc
ctccaagaccttgggctccctctcttggggtagattttgctcaggaagcgaggtctcatt
atgttctgatctcctcactcagagcttttcagccttttcctatatatctgatatctcctt
agctctctcctaggaaactgcatgagtcttcattgccaggttttgaggaggtcaggtagg
acaacgggccaaagtgaaataagggtcacgcctttgttcacctaccgaggcagcgcaagc
agagggagaagaggaaagtgccaggtctttgccttttagtgtggctggaaaggaatagct
ggggctggtttgttcatgaggaaagaggctgatttgggtcttggctttgcaggctgcata
ggaccatggtgcaggcatctgctcagcttctgatgagggcctcgggctgcttgtactcct
agcagaaagggatggggaggtggcctgggcagaggtcacaaggtgagggaggaaggaaga
gagagcaagagggagggctcagactcttcaaccaccagctcttgctaggaactaagagaa
gaactcaccctgaccagggagggcactaagttattcatgcagtgttggtctccatgacc
cagacctggtgcatcaggcctcacctctaaacttggggattcagttgcaatataacactt
ggatgtgacaagcctctaaagtatagcaccctggctctccagggttccatctttcccta
ctgaaagattttgcaaaggggttacatggatgaagcacatatagaggatgggggagggact
gtctccctgggaggagcccagaaccacaggctcctgctaggaagcgcggtcttctgctga
ggcccaataaggtgatgtcttaatagagacacaaggctaggagtgcggatgtgtgtctgt
ccctctctggcctgagatttgggggctgtgagtccttgaccacaactccctccagagcac
tgcagtgtcttgcctgtgcaccggtctggtgtggagtgtgcagtccccatgaggtctgct
aggcaaagcattgttatgaacgcctgtgggctggactggaacatcagaggcaggactttg
gctggagtggcctcctcacatttgctaactcagggactgctaagacatgcaagggagagg
gtaggttttgtgtcaacctgattactatgggcagacacaaggttaatcaccttggagttg
gcaatagtggacaggatctgcccagacaccctccaaggagcatctctgtggggacatgca
tggcaatgccctccctctgtgatggggacctagggtggactgaaggcatgatctgtttag
ttccttccacctttgttccgatttttgccagcttctgtatagtgcatctgatctgacctcc
tctttctcacagctgcccactcctggtcgacgcccagtccaggtgagtccccagtgtcct
tccttgggatgtcccttctctttctgtataattatccctttctgcactccacagagccct
cgttcttctctgagtgaatactacatggcatacaattttcccctgctctgtaactgagac
cctggaatggcgcttctgaaccagacatagggttcaagaggcttctgtcttctgttccat
ttatctcagcttttcatgaagcagtttcatactgtcccaatggccaacccttagaggttta
ggaagtgacctcatatttaattagctttggcacttttctattcagagctgatatgacctt
cctgagaattgagagtgattgccaaagtctcctgggtagccaatgtcagctaaagcctta
aacatggctgccgccacaggcaagcaatgtcagtgcaggcctgacacctcccttcctcac
tccttccaacaccccagattctgcagggctacatgtgcatccagaagaggcataggccat
gctcgggcagggagagggataataaatatttctggtgcctccacttactgggaaacttga
tacccctttggtcagctccttggtttccctaacattttagctcgagctagtagagtgtca
gcaatggtgttagatgtacccgtcagtgcatgtgtcagtgcatggaacaggctaacccct
tgtgactgagaagaggacatcccacacttcagaggcaggagggatcgaactggtctccag
caaggcctatgacccttgctgagcttgctgagctgcagacttgggcagacacatggggag
caagtggcaggaaccagaagtggggtagttttcatgatgtttgccttctccggagacctt
tccttttggagattttcaccatcaactttaattctagcctttgtctctgttgcaattaca
gacacattgccgaccatcaccttgcctgcatcgacagtaggtaaatattcctctcgcccc
tccctagggctcactctctacctctggacaaatgttttttctgaaaatgataggatgagg
```

FIG. 5B - 9

```
gtcaaggtgggcccctctcttttcatgtccctgtgggttgcatgggaggaaggtagcgt
ctctggggacccagctctgggtctgatgttggaggctggagggtgctggtgacttgtctc
ccgtggaatcctgttccaagtggtcaggaaacatcctcatccaggtgctgaggaaaagcc
ctggagggttccctaatcctactaagacctcattcctgtccctcagcccatgggctgcag
aggtgtgaagagtcggtggaagtgactgtccccacacctgtctggccaaggccttgtcat
acctgtgaaattttcagaagtcagacaagaccataggattgccaccaagctcctgagatg
gggagagtctggcctgcctactgtagctgtgtagctctgtcctgtgtgtacccaggttag
ggaatggggtttccattcctgttaacttcagtagggtcacagatgcttccccaaaacttg
agccttcataaacccaggcagaatagggtgtcactgcttctttgactttgatgaagctga
atctctgattttattcatattcaaaggtgactgcctgcccaggtgactttagccattagg
acatgccttgagtgtggaacattccttagattcctgacctcatgatagggatggatgaag
gattcttgtgttccctgtaggatctgaatccagtttggccctgaggctggtgaatggag
gtgacaggtgtcagggccgagtggaggtcctataccaaggctcctggggcaccgtgtgcg
atgacagctgggacaccaatgatgccaatgtcgtctgcaggcaactgggctgtggctggg
ccatgtcagccccaggaaatgcccggtttggtcagggctcaggaccccattgtcctggat
atgtgcgctgctcaggacacgagtcttacctgtggagctgcccccacaatggctggctct
cccacaactgtggccatagtgaagacgctggtgtcatctgctcaggtgggccttcaagaa
cttgggatcactctcttggggtggagtttgctccagaagaaactcctaattacattctga
tctcctcactcaaagcttcttctatgttttctatatttctgaagacttgttagctctctg
ctaagaatccctatgtactcactgcctagtgttcctgtggtcacttaggacaggggacca
aactcaaacaacccagagttttccccttcctgagggaaggcaaggaagaggcagaagag
aaaagtgctggctccccagggctccatttctcccctgctgagtagcacggtgtgagggta
taatggatgcaggacagacagcaaggcggggtagggatcctctcactgtgaggaactctg
aactaaagatgcttgtctgaaagtgggttctcagctgagacccagtgaggaggtctggaa
atagaggctcaagggttaggagtgcaaatgggtgtctgattctatcacgcctgggttgtg
tgaggttggagtccttgacctcaggtcctctcagatcactgctgagcattgcctgtgccc
caggtctggtgtggggagggcagcccccatgaggccggccaggcatggccttgtcattgc
ctgtgatcagggcttgaggacggcacaagggattttggctggagtggcttcctcagcctt
gctgactcaagaatgcctaagacgtgcaagggagagggttggtttaggccaaccgggtta
ccctgggcagacacaagttgatcacctcagagctggcaatagtggacaggatctgcctcg
accccttacatggtgcatctctgtggggatgtgcatggcaatgcccctccctgtgtgata
ggaactaggatggactgagtgtcagactcgcccatttcttccctcctcgttccactttg
ccgacttctgtgtaatgttcctgatctgaccttctcttctctttctcacagcttcccagt
cccggccaacacctagtccaggtgggtccccagtgtccttcctcaaaatgtcccttctct
ttctgcccaatcacccccttccacactccacagagctctcctgtttctctgtgtggatact
gtggggcatattatttctaccccaacaccagttgtgtaactgagaccccagcacagcgc
ttttaaacacacacaggattgaggaggcctctgtcttcttttcaacccctctcagctttt
catgaaacagtttcatactgtcccagtggacaacccttacaggttcaggaagtggcccca
tgtttaatgagctttggtcctttatattccggactcacatatagtttctgaaaattgtg
agtgtcaccctctgacctgttcaaggcatcatcagggcaggctcgataccccatccttc
actgctggaaacattccgagattatcatgggccacatttgtatccagaaaaggcagagtt
tgtgcttgggcagggagagggataataaaggtttgtgatgtcactgcttaaccagaaacc
tgattcctgattgtcccctgggcagcccctggttcccctaacatttatctgccagtgtc
cgagcctcagcaatggcgtctgatgtcctagtcagtccatgcatcagcagatgtgggatg
gcatggtgggggcatcctctaagagatagaaagataccccaggattagagaaatggaggg
ctcagtctggtctccagcaggacctttgtccgtggatgagttcacagcagaggagacctg
ggaagacacatgggaagcaagtggcaggaacaggaagtggaattgttgccaggtggattc
cccctcccagagaaccttttgttctgcaccttttcccttcaagtctaattctgtctttttc
ctttgttgcaatttacagacacttggccaacctcacatgcatcaacagcaggtaaataat
cctctcacccctccctagggctcactgtctctggacatattttgtgtttgaaactgatag
gatgaggctcaaggtgggcccctcttttttcactcccctgtgggttgcgtgggaggaagg
tggaatctctgaggagccagtgctgggtctgatgtttgaggatggagggtgctggtgact
gtctcccatggaatcctgttccaagtggtcaggaaagatcctcatccaggtgctcaggat
gagcactggagggctccttaatcctactgggacctcgttcctggccctcaggccatggga
tccagatctctgaagagcaggtgaaagtgccagtctctgcacttgtgtggccaaggtctt
```

FIG. 5B - 10

```
gccatcactggcaaattgccagaaggcagagaggaccatgcaggtgccaatgagctcctg
aattcggaggggggtctgggcttgtcatttgtagctgtgtatctccatcctttgtgtaccc
agagtggggaatggggtgtccattcctgtcccctcctctggggtcatacatgcttaccca
tagcttgacttttatagacttgagtagaatagggcatcacttttttccactatgacaaag
cttaacctctgggtgcagctatcttccatcatgactgcatgccctggtgacttctgcatt
cgtattgaaacttgactactttgcccactgccctgattgttgtccatgccttatccttga
cctcatatttgagatggatgaagcgttcttgtgttcccctgtaggatctgaatccagttt
ggccctgaggctggtgaatggaggtgacaggtgtcagggccgagtggaggtcctataccg
aggctcctggggcaccgtgtgtgatgactactgggacaccaatgatgccaatgtggtttg
caggcagctgggctgtggctgggccacgtcagccccaggaaatgcccggtttggccaggg
ttcaggacccattgtcctggatgatgtgcgctgctcaggacatgagtcctatctgtggag
ttgcccccacgatggctggctctcccacaactgtggccatcatgaagacgctggtgtcat
ctgctcagnnnnnnnnnnn
```

FIG. 5C - 1

| FIG. 5C-1 | FIG. 5C-2 | FIG. 5C-3 |
| --- | --- | --- |
| FIG. 5C-4 | FIG. 5C-5 | FIG. 5C-6 |
| FIG. 5C-7 | FIG. 5C-8 | FIG. 5C-9 |

FIG. 5C

Sequence SC3

```
gatctgcctcaaccccttacacggtgcatctctgtggggatgtgcatggcaatgtccctc
cctgtgtgataggaactaggatggactgagtgtcagactcgcccatttctttccctcctc
attccagttttgtcgacttctgtgtaacattcctgatctgaccttctcttctctttctca
cagcttcccagtcccagccgacacccagcccaggtaagttcccagtgtccttcctcaaaa
tgtcccttctctttctgcccaatcaccccttccccactccacagagctctcctgtttctc
tgtgtggatactgtggggcatattatttctaccgccaccaccggctgtatttcacatggg
tccttttctattttccctaagtgtcagccggtctgagaaataaagggaaggcatacaaaa
gagcaaaattttaaagctgggtgttgggggagacatcacatgtcagcaggttccgtgat
ccctcctgagtagcaaaaccagcaagtttttattggtgattttcaaaaggggagggagtg
cacaaatagggtgtgggtcacagagatcacatccttcacaaggtaataaaatatcacaag
gtaaatggaggcagggcaagatcacaggactggggtgaaattaaaattgctaatgaagtt
tcgggcacgcattgtcattgaaaacatttatcaggagacagggtttgagagcagacaac
tggtctgaccaaaatttattaggaggcaatttcctcatcctaataagcctggaagcgcta
cgggggaccggggcttatttcatcccttatctgtaagcgtaaaagacagacgttcccaaa
gcggccatttcagaggcctccccttaggaacacattctctttctcagggatgttccttgc
tgagaaaaggaattcagcgatatttctcctatttgcttttgaaggaagagaaatgtggct
ctgttctgcctggcccacaggcagccagccttaaggttatctcccttgttcctgaaca
acgctgttatcctgttcttttttcacagtgcccagatttcatattgtttaaacaatttct
gcagttaacgcaatcatcacagggtcctgaggtgacattcatcctcagtttatgaagaag
atgggattaagagattaaagtaaagacaggcataggaaatcacaagagtattgattgggg
aagtgataagtgtccatgaaatcttcacaatttatgttcagagattgcagtaaagacagg
cgtaagaaattataaaaatattaatttggggaactaataaatgtccatgaaatcttcaaa
tttatgttcttgtgccatggcctcagccggtccctctgtttggggtccctgacttcccgc
aacacagcacagtgctttgaaaacacacataggattcaggaggcctctgtcttcttttca
accccctctcagctttcatgaaacagtttcatactgtcccagtggacagcccttacaggtt
caggaagtggccccatgtttaatgagttttggtccttttatattcaggactcacatatag
tttcgaaaattgagggtgtcaccctctgacctgttcaaggcattgtcagggcaggctcga
tacccccatccatcactgctggaaaaattctgagattatgatggaccacatttgtatcca
gaagaggcagggtttgtgcttggcagggaaagggataataaaggtttgtagtgtctctg
cttagccagaaacctgattcctgattgtcccctgggcagccctggttcccctaacattt
tatctgccagtgtctgagcctcagcaatggcatctgatgtcctagtcagtccatgcatca
gcagatgtgggattgcatggtgggggcatcctctaacagatagaaagataccccaggat
tagagaaatggagggctcagtctggtctccagcaggacctttgttcatggatgagttcac
agcagaggagacctgggaagacacatgggaagcaagtggcaggaacaggaagtggaattg
ttgccaggttgattccccctcccagagaaccttttgttctgtgccttttcccttcaagtc
taattctgtctttttctttgttgctatttacagacacttggccaacctctcgtgcatca
acagcaggtaaacaatcctctcacccctccctagggctcactatctctggacatattttg
tgtttgaaactgataggatgaggctcaaggtgggcccctctcttttcatgtccctgtggg
ttgggtgggaggaaggtggagtttctagggagtcagccctgggtttgatgtttgaggatg
gagggtgctggtgactgtctctcatgggaccctgttccaagtgttcaggaacgatcctca
tccaggtgctcaggacgagcactggaaggctccctaatcctgctgggacctcttttcctgg
ccctctgaccacgcactgcagacctgcaagggtgggtgaaaatttctgtccctgcagctg
```

FIG. 5C - 2

```
tctggccaagtccttgccatccctggaaatttgccagaaaccagagaggaccatgtggat
gccaccaaactcttaaacatggggccagcatgggcctgctctctggagctgtggagctcc
atcctgtgtgtgcccagagtagggagtggggcattcattcctgtcacttccagtggggtc
acaggtgcttccccaaaatctgagcctccataaacccaggcagcatagtgtatcacctct
cctttccctatgataaagctgaacctccggtagcagttgtatgcaattgtgactgcttgc
ccaggtgactctggccattaggaagtaccctgagtgtggaacttgccttagattgttgac
ctcctggtggggatggatgaagggttcttgtgttcccctgtaggatctgaatccactttg
gccctgagactggtgaatggaggtgacaggtgtcgaggccgagtggaggtcctataccaa
ggctcctggggcaccgtgtgtgatgactactgggacaccaatgatgccaacgtggtctgc
aggcagctgggctgtggctgggccatgtcagccccaggaaatgcccagtttggccagggc
tcaggacccattgtcctggatgatgtgcgctgctcaggacacgagtcttacctgtggagc
tgcccccacaatggctggctctcccacaactgtggccatcatgaagatgctggtgtcatc
tgctcaggtgggctttcaagaccttgggctccctctcttaagttgaagtttgctcaggaa
gaaaatcctaattacattctgatctcctcactcaaagcttttctatgttttctatattt
ctgaagtcttgttagctctctgctaagaatctttatgaattttgctacagtacctggtgc
agctgtggccacttaggccagggctccgaactgaaacaacaacccagactttatccccat
cctgaggcagtgcaaggaagaggcagaagagaaaagtgctggctccccacggctccattt
cttccctgctgagtagcactggttagggtatcgtggacacagcacagatagcaggggca
gggagggatcctctcactacaaggaactgtgaactaaagatgcttgtctggaagtgggtt
ctcagctgagacccagtgaggaggtctggaaatagaggctcaagggttaggagtgcaaat
gcatgtctgtttgtgtcaggcctgcttggagtccttgacctcaggtcctctaagaatgct
gcagagcactgcctgtgccccaggtctggtgtggggagggcagcccccatgagtctggcc
aggcatggccttgttattgcctgtggtcgggctgtaagatcacacaaggcatttgggct
ggagtggcctcctcagccttgctgactcaggaactgccaaaacatccaagggagagtgtt
ggttttgggtcaacctggtcaccctgggcagacacaaagttactcacctcggagctgaca
atagtggccaggatctgcctgcacccttatatggtgcatctctgtgggaatttacatgg
caatgcccctccctctgtgatagggactaggatggactgagtgtcaggcttgcccagttc
cttctatctttgttccagttttgccattttctgtatagtgcatctgatctgaccttctct
tctctttctcacagctgctcagtcccagtcaacgcccaggccaggtgagtccccagcatc
cttcatcgggatgtcccttctcttctgcccagttacctcttccccactccacagagctc
tcctgcttttctgtgcggatactgtggggcatattattttcctcccaccactctgtaac
tgagaccccagcatagtgcttcaacagacatagggttcaggaggcttctgtcttctgttc
aatttatttcaggtttcatgaagcagtttcatactgtacaatggacaagccttacaggtt
caggaagtggcctcatgtttaatgagctttagctcatttatattcagagctgatacaacc
tttctgagaattgagagtgactgccaaagtcacctgggaaggcaatgtcagttcaagcct
taaacatgacttctgccatgggcaagcaatgtcagtgcaggcctgatacctccgtccctc
actccttcaaatacccccagattttgcaaggccatatctgcatccagaaaaggcagaggcc
atgctcgggcagggagagggataataaatatttctggtgcctccacttatcaggaaactt
gataccccttgggcggctccttggttcccctaacattttagctcgaactgtcagagtct
cagcaatggtgtcacatgtgcccatcagtccatgtgtcactggatggggcaggctaaccc
ttcgtagctgagaagaggacatctcacacttcagaggtaggagggatcgaactggtctcc
agcaaggcctttgttcctggctgtgctcactgagctgaagacttgggtagcacttggagc
aagtggcaggaaccagaaattgaatagttttcatgatgcttgcctggttcagagattttt
ttttgtagctttcctccctcaagtctaattttgtcctttctctttgttgcaatttacaga
tacttggctgaccaccaacttaccggcattgacagtaggtaaataatcctctcgcccctc
cctagggctcactctctacctctggacaaacgtttcttttgaaaatgaaagaatgaggct
caagctggcgcctctgttttcatgtttccgcgagttgcctggggaggtagactccctgg
gaacctagtcctgggtcagatgttggaggctggagggtgctggtgacctgtctcccctgg
gattctgtttatgtagtcaggaaagatcctcagccaggtgctcaggacaagccctggag
ggctccctaatcctactgggaccttgttcctggccctcaggccacaggctgcagacctgc
gaatagtggggaaagtgcctgtccccatagctgtctggccaatgtcctaccattcctggc
actttgctagaagccagagaggatcatgtgggtgccaccaaactcctgaacgtgaggcag
gtcttggcctcctatctggagctgtgcagcttcatcctgtgtgagaatggagctcacaat
gaggagtgaggcgtccattcctgtcacctccagtggggtcacaggtgcttccccaatact
tgagcttccatagacttgggtggagtaggacatcactgcttcttccactatcatgaagct
```

FIG. 5C - 3

```
gaacctctgtctgtattcatattcaaaggtgattacctgcacacgtgactttggccaatt
aggaagtgccctgagtgtggaacattccttaaatccttgacctcataatcagtatggatg
aagggttcttgtgttccnctgtaggatctgaatccagtttggctctgaggctggtgaatg
```
gaggtgacaggtgtcgaggccgagtggaggtcctgtatcgaggctcctggggaaccgtgt
gtgatgacagctgggacaccaatgatgccaatgtggtctgcaggcagctgggctgtggct
gggccatgtcggccccaggaaatgcccggtttggccagggctcaggacccattgtcctgg
atgatgtgcgctgctcagggaatgagtcctacctgtggagctgcccccacaaaggctggc
tcacccacaactgtggccatcacgaagacgctggtgtcatctgctcaggtgggcttcaa
gacctggggctccctctcttggggtggagtttgctccagaagaaactcctaattacattc
tgatctcctcactcaaagcttctcctgtgtttcctgtgtttttgaagacttgttagctct
ctgctaagaatccatatgaattcactgcctagtgttcctgtggtcacttaggacagggga
ccaaactgaaacaacaacccagactttatccccttcctgaggcagtgcaaggaagaggca
gaagaaaaaatttctggctcccagggctccatttctcccctactgagtagcactgggtg
agggtatggtggacacagcacagacagcggggcagaggagggatcctctccttaggagga
ggctcatggtaaggaaaggacatatgttggggtagggaattctcacttgaggccccagta
aggagcatttggattggaggcatatgggctaagagtgcaaacgggtatctgtgcatgtgt
gacctgggtcttggtcagtttcagctccttccaaagaactgcagtgcattgtgtgtctag
caagcatggtgttgggagggcagctcccatgagatctgccaggcaaagccttgttattac
gtgtggtttgggatggaagatcacacaggggattttgctggagtggtatcctgagactt
gctgacttggtgaattgctaaaacctgcaagggaaagggttggttttggttcaattggac
atcacatccagacacagagttaattgccttggagctggaaatggtggacagaatctgctt
ggatcccttataaggagcgtcttgaatccagccaaagcactagcattcagcaggtctgg
gtgaaactcctgggtcttgcttgaagcctctggccgctccctacctcaatcaatgtggta
tctaccagttgtcaattgatctttaaagaggatctattattagggatgcttttgtttgca
catggcaggaactcaactcaaacactcttaagctagaaaggaattcattgtctcagttat
ccagaatgtttagtggtggatctggagcttcaggtacagctggttccagaagttccaagt
ctttttcccatgctttgcttacatctactcttttatctgtgtgggcttcactatcaac
ttgcttttgcatgtggctgagagacagcagtgggcagccccaagtctatatcccaccag
gagaaggagtcagtctgtcccagtacctctggctgacaaggcctggagggactttgattg
acctgcttgtaaacaggtgctttcttccaaaccatctctattagctctgacggctcagcc
agagttctatacccatctttgtgttccttggggcgacgggaaggatgggggcactaggc
tctacttgaatcttgtaggatgctacttttaaaataggaatgactgtttctattagaat
aaaaaacaggcaggatgtttgtgacagagatagccatccctcagttggacccttccttc
ttttgatactatctgctctttgctggttgacgttacccctctatcctgagatggaacctt
ccctctccctggctgttgcccatgttcattaccatcatctctatctagttccaggactt
ttcattatccccaactgaaagctcttacccttaaccattcataatccatttctctttcc
ctcagcccctggcaaccactaatctgctttctgcctctgtatacagattttactaagaat
tgtggtcactttctatgaatggaatcatagccttttctgtctggcttcattcacttaaca
taatgttttcaaggttcattcatatttagcatgtgtcagaactccactacttttaactg
ccaactaatattccattgtatggctacgccatctttgtctatccatttatcagcttatgg
acatatgggttgcttccatcttttggctgttgtgaataagtctgctatgagaattagtgt
acggttttttgtttgcacttgtgtttccaattttgggagatatatacctaggagtgggat
tgctcggtaatagggtaattatgtttaattattgtggaaacactgaacagttgccacag
ctgctgcaccaaatttgcattccccaagcaatgcctgagaattctgattcctcgtatc
ctcaccaacacttgttatgatgtcttttcatcatggccatcctagtgggtgtaaggtgg
tatttcatggtgttttgatttgcatttccttgatgactaatgatgttgagcatcttttca
tgtgttggtgggccctttgtatatattcttgggagaacaggggcttcattttatagatac
taagctgaaggccagaggaactagactaatgtcagtatcttagcccaggctcacaggaca
gggttcaggtacacagagggatcaggatgcctggcccagtgttgtgtctagcatgtgaca
ttccttcatggaggcctaactctgccatttttctccattctcaggcataggcactgcta
ggtatgcacaactaagtgtcctcatagttgcttctgcccactgtccctgtagctcatggt
attcagtaggtccaggttttgtttcagattgaaggcaagctgtgggtttgaaagtgactc
aggaataagcctcgggcctgatggggtggtccctgtgagcagagtgagtcagccagaggt
ggagaggtggactctcccaagaaccaggtcctagggctgcaccttgccaggcagctggga
gctggtctcggttgcatcctgctgcaggggcacttgagcccagtggtccctgcagatcca

FIG. 5C - 4

```
tgctgatggctcctgcactttaacctctgaatctgaaggcctggctcagcacttgaattg
ctggtcactggggtaactccatcagagaacatgcacagctcagtccacacccaagggttc
tagaaaacaacccttaagttgatgaagaacatcaacttaaaatgatgaagaacaggcttc
cgtcaatgtctatgctgctggagaacattaactggagacccagaaaccttggccttctgg
aagaattctgaacttcacttgacctcagatcctcttcctttaggagatacaggagagagt
taattttcctgtcttttctagaatccaattctggtttggccctgaggctggtgaatggag
gtgaccagtgtcagggccaggtggaggtcctgtaccaagtctcctggggcaccgtgtatg
atgacaccaatgacgccaatgtggtctgcaggcagctgggccgtggctgggccgtggcat
tcccaggaaatgcctggtttgatcagggctcaggacccattgtcctggatgatgtgtgct
gctcagggaatgagtcctaactgtggagctgcccgcacaatggctggctctcccacagct
gtcagcacagtgaagatgctgtgtcatctgttcagatgggcctccaagaccttgggcctc
tatttagtgtgtggttttctccatgacaaggcttctctttgcactggcctcttcccagc
ctgagcttctcttcaagatggccagtttctctgatacctcagcaaggcaataacctcagc
aaatgttgttggcgtctttgaattttatgggtaggcactagcttcttcttatgtaggtt
cctatagcaaacaagggttcaatctactttcaggctgtaagaatgaattcttccaacatc
ttttttgagactaaccgttaaggtttatatctactattccactctcctggatgactctt
ggggagcatttctaagtgatgagatggggacaggcactcagcatttctctcgctcatcat
cctgggcactgggactgactcatgttttcttcttttccttgcagccacccaaataaattc
tactacgacaggtgagtctgctacaccccagtccagcaatatttctcttgggaattccac
cctctcttgtttccagaagtaggaggagtagggtagactcccctggggggtaatttct
ctctgaggactctgatctttgttagggtgacgagctgagttcccactgccatcactctca
tgtctggttcaccgtggagggccccgtggcctcctgctattgcctgctgatagtgctaa
gtgctggcagagatgctgctgtggaaggaggctttggtcctcccattatttcagatgaaa
ataactgtctaaattaacccatggaaaattaggaccttcatttagaaacatagccaagt
aatacttctgcacgtatttgtcaaataaagaacactttcactttgagggagccatccgca
aagcgttttgtgccacagtgaaaatatcctgggccaaatatgttgggaggtgctacata
ctctagaccttactggccatgaacagtgtaaactggaatggtcaaggctctgagaagtcc
tgtactaaggaaaaggatttaactttgtcagtcaaacaaattactatggaatggaaaaat
tatctactaaaatcctaaacagcttcatttttttctagattggtggcatccaacaact
acaaccactgcaagtaggtatcacattttctacctgaaccataggtcatacatttcttat
ccccaagcttggctatccatgagcgaatgctctgccccaccccagccttcctcaatctgc
acatagccctggcctgtcccactatacccttcacctcttcatttgaatcaatgagataag
tattcttaaaataatagacttaaaggcttttattttggggggtatctccaaagctttagg
aggaagaagggagacaaatagtaaatggataatttactacaaattatgcttttccatgt
cattttatttcaccatatggctatgtttcaatagattttcattgcttttaaaaaataat
agggatacttttctgtgttattaaatcttttctcacaatcattttaagtccctgtattgt
attctattatacagatatgccatgaattatttgacaaatcatcagatgctagatatttgt
ttgtatttcttcattactgtaaatgatttgtgatgaagaatatttttatagataatttt
tttgcatacctcactaattttcctttaggatataaatgggtttactggaccaaagtcaa
tgtcattgtagtgcctggtacatagaatgtacttcatgcatattaacttttactgtgtta
ggtatttaagatcttgctgtgtgtatggtcaaactaccatcaagaatggttgtaaaatt
atggaatgatgtaagagacaaactgatcttcttcctcagagctcacaatattattttgta
cacaacaaactagaaaattacagttgtgacaactgtttccaaggaaaagttcagtgtgca
agaggaagtattagtagagatcttccttgattggggagttaggggaagttccttatgga
agtgacatttaagctgggagttaatagaggagcaggttcatttgctgaagtgtcttctaa
ccagaagggatgctttgaaggccctagggtgggaaggagcttggctctttgaaggagggt
ggggtgcgggcaaggagggactgcaggaaatctgtcgggtgaggccagatcattcagggc
cttgtgggtgggttaagactcccatctttatcctaaaggtagggaggctgcagaaagatt
ttaatcttgagaattagctaattggaaatatatttgcaaaagatcatgtttatctttct
gccaaactgcatttcctgaaggcaggggccatgtctgccttttttcataatgtatccttat
tatctagcattgtgtctgcctttcaagaactgtttattgaaggaataaatgagtgaatga
atgaatggataaattaatgaataaatacataattactgttggcatttggcatacattcc
atacactgtatacacacacacaaacacacacacacacagtatggcatgctttatatcc
cattgtataatccatcattttcatttaagtgtatataatactttttttcatgacccttaaaa
ttagcattttataacattgaaattatttgtatagaagaaggtttaatgactatatgatt
```

FIG. 5C - 5

```
ttccactgtatagatatatcatcatttagttaaacggttactaattgtggggcaaaaaca
ttgtttccaattatattttataatgttaagtgactatatacaatagcatattttataacc
atttatatttaatgattagaaatatgtaactcgtatccttgtctctgaaagtttgacttt
atccttaattatttcccagtgtagaaatagaaagggagggcaggccacatgatcttcaag
aaacactgtcttcccatcaaatgggagaacgtatttctatctcataagggacttgtatct
aggatatataagtgactcttgtagtcaatgataaaaagtcaaataacccaactgaacaat
gagcaaaagacctgaaagatatttctctacagaagattcacagatagcagagaaggcatt
ggaaagatgctcaatgtcattagccgtcagggacatgcaaatgaaacacccagtaggtgg
gctgtagtcaaaaagccagataatagcaagtgttgatgaggatgtggagaaattggaaac
cttatgcacggctgcagggaatgtaaaatggtacagccactttgagaagcagtttggtgg
ctcctcgaaaggttagacctggagtcaccatatgacccagcagttgtattcctaggcata
tacccaggagaaatgaaaacatatgtccatacagaaacttgtatgtgaatgttcaggaca
gctttattcatagtagccaaatgtgaatgcaatgcaaatgtccatcatggtgaatcgaga
aacaaatatgatatgtccatgcagtggagtattatttggcaataaaaatgaatttaatag
tggccgggcgcggtggctcatacctgtaatcccagcatttgggaggccaagatgggcgg
attggctgaggtcaggacttcgagaccagcctggacaacgtggtgaaaccctgtctctac
taaaaatacaaaaattagctgggcatagtggtgggcggctgtaatcccagctacttggga
agctggggcaggagaatcgcttgaacccgggaagcggaggttgcagtaagctgagatcgt
gccactgcactccagcctgggtgacaagagcgaaactccatctcaaaacaaaacaaaaga
aaaaaagaatttaatattgatttatgctacaacatgatgaactttgaaaacacattgag
aagtcagtcaaaaaaactaccatattgtacaatttgttttatatgaaatgtccacaatag
gcaaatctatagagacagaaaagtagatcagtgggtgccaggaatggagggtgttgagaa
gaaatggggagtgattgctaatgagtacagggtttcttttttggggtgatgaaaataatct
aaaattgactgtggtgatttcagagctctcagtatgctaaaaaccatggacttatcccct
tagaaaagtaaagaaagagttatgaaaagaaaaaaaagacgttttaatttctatcac
tgagtgtgcacatgtttttaaaaagttttattactataaaccaaccaacaaaatgtttg
accacttaatatttatccttttctgataaataacaatagctaatattgctgggtgcttat
gtgcctggcactctctaagagtttatatagacatagaaacctatcttatgtttatgtata
aatgttcatatatacatatcttatttaataccctcatcagacagatgaggcagatgccat
taccactctcattttctgatgaggaaactgaggcagagaggttaagtaactggctccag
atcatggagctgatagaggcagagccaagatgcaaacccaggcttcttgttgcagaaacc
ctgctcctaacccaacgttgtgctacttgtgaattggcagagtcctgtgctcatggaaga
cgctagggaacacactgtgttatggagtgctctccacgggtcagcactgtgttcagccag
gactatcccacgtccctgtctgtagctgattgaacaatgatagctgtcactttgttgctt
tcttggcattttgctagaggtgacacatgctccctctgaagcttgggtcacctcctcgc
agagggttgctgtccaggcctaacagggaaagcagggacttgaatcaaagcttctaatgt
tgggccacctagaaccaggcccaagagaggggacttgtttacagggaaagttaagtcttg
ttataaagtgcagaagatgaaactggatgatacttacacagatgattccttgtcacaaaa
tacctgaagacctggtacaatggagatgtcccctctctcctctctaggaccctcttcaaa
ttgtggtggcttcttattctatgccagtgggacattctccagcccatcctaccctgcata
ctaccccaacaatgctaagtgtgtttgggaaatagaagtgaattctggttatcgcataaa
cctgggcttcagtaatctgaagtaagtaatgcctggtcatctggtgaggggtgagttcct
ctgcagcacacccactggtttagactgtgtcctgggctgggatgcttttcactctcatgt
gccatggacaagcttttggtggctttgattcctaccataaagcatcagggaacactgatg
tcctttgacttaattgaggaagagctagaagaaaaacctgtattcaatggcatccctcgt
aaagtgcaaactatttataaaatggaggggcaataggaatttcaatgttgacttgaatac
attttctccatacagattggaggcacaccataactgcagttttgattatgttgaaatctt
tgatggatcattgaatagcagtctcctgctggggaaaatctgtaatgataccaggcaaat
atttacatcttcttacaaccgaatgaccattcactttcgaagtgacatcagttttccaaaa
cactggcttttggcttggtataactccttcccaagcggtaagtgcacactagaccatgc
ctatgaggcttggtggatttacccagctgcctctttggggcaccatggttccccaagga
aatcaaagaagggcctcagcgatgcacggcccattctctttctcttggcactgactgtgt
gggcaggcccttgggaaggcagcaaagggtgcagactgggggttccacctggccttgggt
ctgccaccaactctccaggggacctggtgactctccttcagagccacccctctccgtctg
gaggtgagggatctgagcttggcgatgtctagagccccttcagctctgcatggagcgg
```

FIG. 5C - 6

```
tccagtacctccaccccagcttttccacatttctatttggcgactttagaggtgggaaaa
ggcctgtgggatgcttggcctttgaggtttgttgtgggacatttgttgtgggacatggcc
atgatctctcagttaatgtgtctttcagatgccaccttgaggttggtcaatttaaattca
tcctatggtctatgtgccgggcgtgtagaaatttaccatggtggcacctgggggacagtt
tgtgatgactcctggaccattcaggaagctgaggtggtctgcagacagctagggtgtgga
cgtgcagtttcagcccttggaaatgcatattttggctctggctctggccccatcaccctg
gacgatgtagagtgctcagggacggaatccactctctggcagtgccggaaccgaggctgg
ttctcccacaactgtaatcatcgtgaagatgctggtgtcatctgctcaggtatggcccaa
tgccatggaaggcccatttcacctgtaacttgctataaagcaagagcttaaggccagtgg
ctgatggtgtctgtggcccaggcaggagctggtcattgtgtcctcgtggcctgcgcactc
cagaagagcatgcagggggctgctttatctttggccagtttctggacccagggccattat
gctgaacactcatctgactaaaggacctccagcaatgattttacttctttatgcttcagt
ttccttgactgttgagtcgggtggctatgacagtacttgctactggtgacaattgggat
ggttttagaacaatcatggtcaaggagagagtgatgggtgttatgacctcagctgtaatc
ctgatgaccacaagtatgacgggacttagggagcatctggggaagctgggaaggcttctc
aatagcaattgctgggtggacctggggaccctcgccaggggggtcaggttatggccat
gtaagtgtatctctgtctcattccggcccctcctccaagccacatgtctgtgacctatgc
ttttttctattccttttcaggaaaccatctatcgacacctggtaagtccctccgattt
ccattccacttccctggtctccaggtctctccattactgctgcctagactgtgcaggca
tgttgctcactctccaaggagttcatctgtggtaccatcctctacagcccctgtcccctc
ccctgccggccaccaggatagtgtgcccctctctgtgcttcagtggcctgacccacctaa
gattaggatctccagtcagtcccgaggtgaggcccgccacctgtcagatttgactgtcct
cacagacaccagaccctgaccagtgttggccaaatggggcccactgcatcgcagagctcc
tccctgcctgccctgagctgctctgagtgttccagcatggccctggcacctctccaac
accccccactgccccgcccctgcttgctttgtcatccctcctggcctcccatagcagc
agcttcaggcctgtgccctcccatccattctacactgtgcagccccttcaagagattcct
cagggtcttctggtgatgaccccgctcctcagcacagcatgactgccagggctccccatg
atctgctccctatgcttggtgccctctccccatcctctgcctgctccatctacacggagg
ttcccaaatctattccacccaggtgcagttgcacctgctgttcctctgcctgggacaccc
cgtttctacctctttgcctgcccctaattactgccttttttccccactccatctgggg
caggggccagacttccaggctcctctccttccccaggctttggtcaatctcatcctttc
ccagtgtgctgggattcgctctcctccagacctccccaaaggcaagtgagctccccaagg
gcaaggcctgtgtccagctcctccctgtggactcaggcttggcacagcatctgcacagct
catgagcagtagacagctgtgtcagggatgccagaaaactgatcctgatcttttctttt
gtcaacagctccttttctcaacatcacccgtccaaacagtaagttctgagctccctgaca
agtctgtggcagagtggcctggaaattccccttcccatttcctcagtgacaatggggctg
gggaggagatggcttcccccaaagtggtctccctgcaagagtgccctgccagccctcagt
ggacggtccagatctaggccacctcttgctcttacttggtttctgtcttgggaattattt
tataaaattttaaagtaatttaaatttaaagtagtccgcaggtagactgtgcagtgtgct
ctgggggtcaccgacattcccactttttgtcctgacagcagattattcctgcggaggctt
cctatcccaaccatcaggggacttttccagcccattctatcccgggaactatccaaacaa
tgccaagtgtgtgtgggacattgaggtgcaaaacaactaccgtgtgactgtgatcttcag
agatgtccagtaagtgtgcgcccagaagaatgccttggggccccacagaccttcaagag
ggaataaatggtgcttaagtgtgcgcccagaagaatgccttggggccccacagacctttc
aagagggaataaatggtgcttagaaagccaggagagaagtttgctgagagacattttga
cctagcccagaggcatcccgtggagagttggggagggggcacgagagccttggagtggac
aaaagctctggtttcaagtcctaggtcttcaccaatttgctgtgtgaccacaggaagtc
actcaactttcctgagcctcagtcaaaagaggggaataaaatacctgcttcctcacctc
actgtttactgggaaggtcacgagaaacagagaggagagagagggagagagatgtgaaaa
tatttacaaaatgttgtccagtggaaaagatggttgttaagtagtaatgatagacttagg
ggcaataatagcactaataatcctattaacaaccacactggccaggtatgctgcctcagg
gttgtaatcccaacactttgggaggccgaggcaggaggatcacctgaatgcaggagttca
agaccagcctgagcaatatagggagacccctatctctacaaaaaagtacaaaaattagc
tgggtgtggtggcctgcacctgtagtcccagctactaaggaggctgaggtgggagaatcg
ctagagccctgggagttgaaggttgtggtgaactatgatagcgccagtgcactccagctt
```

FIG. 5C - 7

```
gtggaacaaaacgagaccctgtctcaggaaaacaaaacaaaacaaaaagaacaattgtat
ctgttttgtggaaccctttttctccacccattcctttcttcatgtgagttccccaggggt
cgggcagagatggaggaattgctgctccagagggtagggtatctgctctgcatccaatca
taagtagaaatcatcgttttaagcagagaggacattactaaaagcacttttctttctttc
tttctttctttctttctttcttttctttctttctttctttctttctttctttctttcttt
ttctttctttctctctctctctctctcttctctctctctctctctctctctctctctctc
tctctttctctctctttctttctttcttttttttccggacatggagtctcgctctgtca
cccaggctggaatgtagtggcacggtctcggctcactgcaacctctgcctcccggttca
agcgattctcctgcctcagcctttcaagtagctgggcttacaggcacacgccacaatgcc
tggctaattttttgtatttttattagagacggggtttcaccatattggtcaggctggtctt
caactcctggcctcaggttatcctcccacctcggcctcccaaagtgctgggattacaggt
gtgagccaccatgcctgatgtcaaaagtacattaatatatgatttatccaaggaggcggg
tggcccagctaactgtgaagaggcaccagtgtttgctagtgtcctgaacaaggggctaca
ctaatttcttctctaacagccactgttgaacaaaatagttttccctgttgatttctgttt
gcagtgggctttggagtctctgctttagtgattcatttgggatttgcaaaagatacatc
atttattctctttgtcattacaatacaaagattgcacttaaagctgatgcagtcctatg
ggaaaaggttgaccatgactggttctttaaccagcatcttgatagcaatgaccatcacca
tttgtgacattttacaaagcccttttctgtatgttgttttatttgagcttcaccatagcc
ctcttcagtgtgcatggatcagattactttgcctttgtaaataggaaaagctttagagag
attatttgacttgcccagtatttatttattcaattatttatttctctcactatgaattca
tgcatattgatttattctgtgggggcactagggacttttcgatggaagaaaaatggtct
aaatcaggatgcgagccccttccttcctgatgtaaagggctgacaggtgaggggctgtag
atttcatatgtgtgattgcaaagggcaggactaagacccaggcatggaggttgagggaag
atgagactctcttgatttaaggatacctatgactttcttttgtttaaattttttattttttc
tttttatttttttgagacagggcctcactctgtcgcccaaactggagtgcagtggcacgat
ctcggctcactgcaacctctgcctccttggttcaagtgattttcctgcctcagcctcctg
agtagcctccctcacccacaggcttgtgccaccacgcccggctaattttttggattttta
gtagagacagggtttcaccacgttggccaggctggtctcgaacttatgacctcagatgat
ccacctgccttggtctcccaaagtgctgggattataagtgtgagctactgcgcccagcca
aggagacctatgactttcatcgatgaactttgtcagagtttctggcacagaggtgtgacc
ccaccctgagatctgacccctgcgtcaaattctgggaggaaatgaagccaaatggtgtg
tcctctctctgcaggcttgaaggtggctgcaactatgattatattgaagttttcgatggc
ccctaccgcagttcccctctcattgctcgagtttgtgatggggccagaggctccttcact
tcttcctccaacttcatgtccattcgcttcatcagtgaccacagcatcacaaggagaggg
ttccgggctgagtactactccagtccctccaatgacagcaccagtaagtccccttgtgga
aatgctctgttgggactggggacatcctgagagcatctgtggctcaactgtcctgttgtt
gtgaaataagaaatgaaggaaccctttcaggtcaccagggcttgattttcagctgaaagg
gaccaggagcagtgggacttgggactctggctgcccagaaataaagtcagggctagaact
ggctgatgggtgatgattggtcttactgtggtcagcagagactaagtagagggtccagat
gatgctcttcgtggagagtgatgagtcagtgccaaaggcagaggtgacctcttggcttga
aaccttgtgaccttctcagagtgtgggacactgtggccatggcctgagacctaacacatt
tggtttctatctgaagatggactgagctgggtggctggaagtggctgagataaggtcact
cagacacttccagcagagcctgtatggccatgatttgagttgctgtatggactgatatgt
agaatggccaagggccaggcaaggtgacatccagggtctcttatgcagtcaggattaaag
actgacttgcttcatggctaaaagaccttgtttcatgacattcccacaatttgatcatac
agttactttactttatagataaatggtaacttggccaaacataccacttatttaaaaatc
ctgcctccaattctccatcagagaaatcctgagtccacgtgctctccttgggctttcata
aggatggggctgacttgaccctcgggtccttggggattgcagtgaggtctatgcccaca
tcctaagtgctgacctccctgtcagccaccctggtctgtgcacttttttaagtggaaaca
gcctctggccccgtaggacttgtggagtctggggcagtgactgagtgccttatctgtcct
tgtctatcagacctgctctgtctgccaaatcacatgcaagccagtgtgagcaggagctat
ctccaatccttgggcttttctgccagtgaccttgtcatttccacctggaatggatactac
gagtgtcggccccagataacgccgaacctggtgatattcacaattccctactcaggctgc
ggcaccttcaagcaggtaagcctggggcttcccattccatttcccagtgcacaagctttc
ttagagcggtatgtcctgtgcttcttgaattctggggatgaagaaattatgatttggga
```

FIG. 5C - 8

```
taatcaggacataattggaataaaggaagataaaaaacctttggtgctatgatatggctg
cagctacttccaaataggaagaaggaagctgagcagaaagagtatctcccgctgtgtcca
gcagagagggcttctggcagaccgccactcccatcagcaataacaacagcagctcctgga
gcaggtccagattttgcagggcctgaagattatacagttagggttgggggtgagaggcag
gtgttgagatgggcagggcctcattaagtcaaagaatgcaatatctatgaactttata
aactttgcaaaaacgtatggctgtgcaaacacattgctaggccttggaggaggcctgcac
attgcagtaggcagggaagaggggggcccaaaagcttcagcttcattagctccatagtcag
ctggcctctgcagctaccatttgttgagctatcaccatctaagatggcccctgcatcca
attttgggtgaaagtgaagccaatatggtgtgtcccttctctacaggcttgaaggtggct
gcaactatgattatactgaagttttcaacagcccctaccaccgatttctgtggtttgcct
gggactttgcagattttagcatagaaagtcccacgttccaggaaaccctcactcccagg
caaatgaggacggttagtcacctacaagtggcagatgctgtgattggtccttgtcatac
tcccccagtgaaggcctggccttaattgtgttgggttctggcttgctgtgagtttggtca
gtggaagtcagtccactgaaggtgaccattgttcctatgccaagtgagcagcctggagac
tccctgagcggccccgctgagggcccttcacacccattcacacccattcacactcgttca
cacccattcacacccgtttggagcggccagacaactctgtcagccctgtttcttctaact
tggctgatcatgaatagcacacgccacattcttattcctccactcatttatttatttta
ttttatttttaattttttaatgacaggttctcattctgttgcccaggctggatgcccaggc
aggggtgcatcatagctcacagcagacttgaactcctgggcttaagcgatcttccagcct
cagcctccagagtagctgggactataggcatgcaccaccacacccagctaattaacaaat
ttttttttgtagaggtgggatcttgctatgtgtcccaggctgatctcgaactcctgagct
caagtgatcctcctgccttggcctcccaaatgctgggattatgggcatgaaccactgctc
ctggcctcctctatttctttaaataaccatattgcctatcacactgagtgcctcaggggc
agggccaatgttttgttcatctttgcaaccccagtgcccctggtcctgagcctaagagt
tgatatagtattattaacagctcatacagatatcagacactgaactaagtgtgctatata
acttttaaaattctcaggacaactttattcccacttaattatgaggcaacggaggcttgc
agaaggtaagccacttgcccagaaccatatggccatgagctgcgggtctaagacacagaa
gtagggctgtgccatccatggctggagcttcccacagctccaccaggctggcctgtgata
gtgaattttatctaaaattagaactgcttcttctgaccaagaaataaatctgcactcca
tgttcattatttggagtggattcagaatttacctccatcgtaggcaccacaggcaaatgt
gacatccatgcaaatgatcatgttaatgtacagggttcaatggaaagcacttgagagcat
ctttgaaagagtaagaagggtcatactgtcatgtgcgtccgtgtgaaaagaccaccaaac
aagctttgtgtgagcaataaagcttttaattacctgggtgcaggtgggctgagtccaaa
aagagagtcagcgaagagagatagggtggggccgttttataggatttgggtaggtagtg
gaaaattacagtcaagggggttgttctctggcgggcagggcgggggtcacaaggtgct
cagtggggagcttctgagccaggagaaggaatttcacaaggtaacgtcatcagttaagg
caggaaccagccattttacttgttttgtgattcttcagttacttcaggccatctggatg
tatatgtgcaggcttgggctcagaggcctgacaaaagggtttattgcggtcgtatggttt
aagtcatacggtttattgtgacaactgttggcactgaaatataaagcaaaaacaaatttt
taagacagtttaaagtcagaaaatgtacgctaagagcaggtggacaaggtagaaccccctt
cctgtgggtcttccccagacctggacccagagtgtaagctctggcaccctgtgctggctc
atagccaaaggataggcacgtgccatggccatctctgagtggttctgggaggggtggaag
tcttgttgagtcatgtccctctcattcacacccaaatcagctatgggattcccttagcag
gtgacatgtgcctgactctgctctcttgcctgcctctcctaggcagacaatgacaccatc
gactattccaacttcctcacagcagctgtctcaggtggcatcatcaagaggaggacagac
ctccgtattcacgtcagctgcagaatgcttcagaacacctgggtcgacaccatgtacatt
gctaatgacaccatccacgttgctaataacaccatccaggtcgaggaagtccagtatggc
aattttgacgtgaacatttcctttatacttcctcatctttcttgtatcctgtgaccagc
cgcccttactacgtggacctgaaccaggacttgtacgttcaggctgaaatcctccattct
gatgctgtactgaccttgtttgtggacacctgcgtggcatcaccatactccaatgacttc
acgtctttgacttatgatctaatccggagtgggtaaggagtgtctttatgctatggcctt
aaacctttacttgataactcaaacatgagtagccccaaaggcttgaagaatgcaaatttt
gatgaactgcagttcccagtacttccagcttaactggatccccttctacatgtagtgatg
tcctgtagcttcacctttgaggtgcttttactctgtgttctgtatcacatccctgattt
ctcatcaggtaggatgaccatgtatcatctccagttaacatctggggagatgggtgtctg
```

FIG. 5C - 9

```
gagaatagaacagctcagcagtgttcactcagcaggttagctgtaaactgtgatcagact
ctaggtgactgaactccagccatacggttaaaaagacctgcgtatagtgggaaaagcatt
gatttggagcagaccaaggttgaaatgccagctctgccacgtgccagttgcatgattctg
ggccagtgaaagcacctctatggaccagttgctcgcctgtcaagtggggataatgacacg
cacatcataaggctgttgggaggatggaatgagagagagtggatgtggcactgagcacag
agagtgtgcggcaggtggtccaccaggaatgtgcactgaagatggcaggagccctgctgc
cctccttcagcctgggaatagaagctctgggagtccatgggttccagtcaagctcaggag
gtgcagaggtcaggccagagatgtcaggctggggcagagggtgtgcaggctgggctgct
ctaccatagcccagcttccctggatgactgcatgtgggtgaagtggggtttgactcttct
gcactcatgatgacaccatgatgtgcaactccagcccctctgaagtctctgttgatgga
tgtgtaccacacttcttggcttacaatatagacctggacacttcagtagccattgccttc
caagagaatttataccaataggataaagagttctactaggaattagaggtgggcagattc
aattcgacaccctcttgatatgctaaacgtagcacctctttccaggcacagtgtgaacat
atgtcagttcagtaggtaggtgttgaggctcaccttgtttacagtctatgcagcttgctc
aattcacagcagccccttggtggctgagaggaggggagaaagcttaaccagattcccgt
tgtacaaatagtcataaggtgacttttgaatttgtgtgaattgattgacattaatgaaaa
tgagtgggtgaccttagttcttccttgccaaggattctttctggtcaaatcctgccatt
tctatatgacaatgcaatttgctgggaagacggggatgtgtgtgcaggggtagatgtacc
ctggctatacctggagcacagggacttattggctacacctggccatcaacaagatcatcc
acctggaagtccattagaatgacctggggctccaaacacaccctgcccaggccctacccg
tacattctctgtttggcctggtggggcttgggcatgttacgtttaaaaaatcttgagtga
ttctgaggtggagtcatggctgtggcttcgctgtggcattctggtctgcgtggagccctg
aatggcagggttttacggcaaatgcaatgactgcccagggggcttctaagtgaccctgacc
tttttcccaagtgtcccacctctgaacaagcctctggctattttgcttcctcctttgcc
actaagggagctactgtgaaaaaaaaaacaaaaacaaaaaacaaaacttggtatttgag
agaatctgggttgcctatggaggaaggaaggaggctctagaagacagaaggagggagca
gatcctggccaggttcccaggctgagccagactgccctggagaccacatccaccacccac
gagaaatgcccatcctaggccagtgggccagttttcctggcttttctctttgccatgccc
ttcaaaatcccaccaatctataataactgggttagtgtgagctgcttcttccatcttagg
aaaattcctgtaagcatatccttaggttatttccctctgaccctgctgagaggaggtg
ccccagggaatgaggagggggtttatatcggtataggggctcctggagggttcgcaggcc
agtgtggaacgtacagctgcatggggctcagggcaggctgaggagggtcaggaaagagag
gccctgggagagggagggtcagggcactgtactcagagtgcagccgaatgagaccttgcc
tggccctgacaccaggtgagagaagggaaggtcatttacttttctgccctgtctctgggt
cccgctcctgggctccaaactccagctacttccctgactcatctggtttacctgggtgca
tggagcatgtggtcattgtgggattaggcctcaacccactgtgcagtatgggacctgctt
gtctattgggaaagccctcgcaggctttgctgcctaaggatggcggtgaggtaccggagc
tgccaggatttctctgcaggcccctcagtgagtgtctgatccacacgttctgacagaagg
aaggtgaggtgtgcaggaggcagggcagtgaggacaggctgtggagttcctcacctggt
acaactgagtcatgaaggaagaatcgggccttggtgagagctaaggggctactgttctct
tccagatgcgtgagggatgacacctacggaccctactcctcgccgtctcttcgcattgcc
cgcttccggttcagggccttccacttcctgaaccgcttcccctccgtgtacctgcgttgt
aaaatggtggtgtgcagagcgtatgaccccctcttcccgctgctaccgaggctgtgtgttg
aggtcgaagagggatgtgggctcctaccaggaaaaggtggacgtcgtcctgggtcccatc
cagctgcagacccccacgccgagaagaggagcctcggtaggtggtcgctctcagaccc
cactgtccaccagggcgcagacccctgactcggggacttggatgttcctcttggtgtca
tattccaactcagattgagccctacattgtgctgcacctggtcatacggagttgaatcag
acctggttcccgcctcccccaaggctcatggtccttggaggacccgttgcagggcaggt
caagagagttctgacctggatggcccatagacctgacgtcccagaatccatgcttctcat
ctgcaaaatgaaaatgtcaatacttacttcttagcactgttgagagggttacttacataa
aggaattttggtgaaactgcctcagcctgttcctggtgcaagtcatttgagtgcttggta
aatggtacttttgttactcctgttgttgtcacccctgtt
```

FIG. 5D - 1

| FIG. 5D-1 | FIG. 5D-2 |

FIG. 5D

Sequence SC4

```
tcttcctctcctcctctgccaggctctgtcctggtgccctgtctgttattgtggtctcct
ctccttcccagacgtgttggtggctgatgtggaggagacagccagcacccaggggaggta
tcacagcactgccatctcttctggggtcttcctggctgtggttctggttgtggcagcctt
cacccctggggaggaaggcacacagcaccagtggccggcctctgagctcctagatatgaag
cccagagaaggtgtttagatattggctctgccagcccaggcacccgagagaggatggaag
aaacaagggtgcagagcttggcgcccagcagcacctgaactccatttagcttggcacagg
tgtatggtggggtgggtggaggtggggtgaagaaagatggggtgggtagaggtggggtga
agaaaggtggagcgaggttttccccagatccgaaggctcagtgctgggtcaaaatgtcaa
aggtaaacaggtgctaacgtctaaagcctcacctgcaactctaagccaaacattagtaac
agcagagctttctctaggtggaatttctgagcctttttttttttttttttgagacagt
gtcttgctttgttgcccaggcttgagtgcagtggcacaatctcaactcactgcaacctcc
gtctcccgggttcaagcgattcttctgcctcagcctccctagtagctaagattacagaca
ggctagaccatgcccagctaagttttgtatttttagtagagacggggtttcatcatgttg
gccaggctggtctcaaactcctgacttcaagtgatctgcctgcctaggcctcccaaagtg
ccgggattacaggtgtgagccactgcacccggcctcttttctgacctttataagctcgc
ttcttaggcctgtagcataaatctcagcctttccttagggtagagccagctgaataaaga
acctttttcagagtaagtgtcaatttggccactgttgccttcgtttcccctaagaactag
atcctttcaaattaagcagacaggtggggtggttgtcatacagaatgagaaggggcaact
cgtgtgtcttcccagtgtccttggagtgttggttcttcccaaagcaggatatgcaggatg
cagcctggagaaagacaagaatgctaaatgcattgtaagtttcagtggctgtgattgaaa
attaaagatgattgcctccatttctctagggatctgcctcttttggttttgacacttca
tctccagaactatgggctggggcggttcagggaaagaagcaaactccttagggcccttag
gaagggagtcctgtttgcatgaggtctccagagagaaggagattgacaggtgacccaagg
agctcagaagaaacaaagggatgagctgggttccaaggaagcagtacatttgcctagaaa
atcagagagaaatcaggctcagggctcctaggtcaggcttggcaggaatgggagcttttg
tgtactgccctggcaatgccagtgtttgccccatgaagccaatctcaggacccctgtccc
aagaggggacagctaagacagcctaactctggatgtgtgagttgagctgcatgagacccc
agcagggcaatggctacaggggaaaccccaggacaaggggacagagaattccagcagaga
cttggccatagctgccagctctgactagggctgcccaagagctgcccaccaccggcagct
gtggtgagacgccatgagcctccgtgggattcagagtgcgtcctgagccctaccaggagt
cagaggagctaggggcccagggactgtctcttgttggtttccattctccttgccatca
cccccaacactcacccttaacctcccaggctggggcagttaaggaaagccttaagggttc
cctgtgaccatgagtctgccctgaaaagcaatgtcaatgcagtggaatgcaggcaccag
cccaggactggatctgagcagatgcagaagcagcaggaagctggagtggtgtgcgggttt
gaggtacacatcaatcagagtaacaaagtggcaagtcagacatccgagaattcaaaaaag
ttcagaggctgggaacccaacatggaatcccaactccatccattcattcgttcgttcatt
cattcattcattcattcattcattcgttcattcactcattcatgaatgtctaagttgtac
cctgtgcttgagaaggagcagtggaggctgtgggtccctgctgtgaggatgaggggacc
ctggggctggggctcagcaggcttgccctgagtggtccccatgagcgccagccccaagc
caggctctgtacttgaacctgtggatacaaagaggggtcatgcagggtcaccattataa
ggggaaatttatttccacaggaaacatttccacctcctgaagtgtccctctccttaaaa
atagccccagtagccagtgcttcttcgcagataaccaccacagtgttagccacttggcag
cctctcaaggaaggaggtaatggccccctttatcagcagggcccagccaggagagtggcta
gtagggacagatgagtttggtagcaagaggcagtgaggtccaggtgaaaggtagagcaga
agacagggccaccggtgacaggggctctggactaaagctgtcagagtgtgactgagggtc
cagtcacaggggacacagagaagtgggcttgcttgggagcagggacccatcctcccatc
```

FIG. 5D - 2

```
cacaccacatctccacactcagggaggattgggctgacaccaagtggctgtgattcccag
caactgagactgtggtttgaggcaagggtgctcaactctactgcacgtgagaatggcccg
ggggcttttgaacctgctgctgccaggctgcacccaagccagttagatcagaatctaatc
agagggcaggcctggacattggtgacccaccagactcaggttgttccaagattgagagct
gctggtttaggactccttaaatccctctgagagagtccaggttgtgccctgtgcttaaga
aggagcagtggagactatgggtccctgctgtgaggatgaggggggaccctggtgcggggtt
ctcagcaggcttgccctgagtgttcctgaaagatctactttccaag
```

PROTEIN CONTAINING A SCAVENGER RECEPTOR CYSTEINE RICH DOMAIN

The present invention relates to a protein containing an SRCR domain, a nucleic acid encoding such a protein and a method to produce same. In addition, this invention concerns the use of the nucleic acid and protein as well as antibodies directed against the protein.

The expression "SRCR" domain means "scavenger receptor cysteine rich" domain. Such a domain comprises about 110 amino acids and is found in many proteins involved in elemental processes of the cell, e.g. cell differentiation or cell-to-cell contact. Nevertheless, these processes have not yet been understood in detail.

Therefore, it is the object of the present invention to provide a product by means of which it is possible to investigate, and optionally interfere with, elemental processes of the cells.

According to the invention this is achieved by the subject matters defined in the claims.

Therefore, the subject matter of the present invention relates to a protein containing an SRCR domain, the protein comprising the amino acid sequence of FIG. 1 (SEQ ID NO:1) or an amino acid sequence differing therefrom by one or several amino acids.

The present invention is based on the applicant's discovery that in animals, particularly mammals, more particularly human beings, there exists a protein containing an SRCR domain, which has homologies to known proteins containing an SRCR domain but differing from these proteins on the DNA level by hybridization under conventional conditions. Such a protein comprises the amino acid sequence of FIG. 1 (SEQ ID NO:1) or an amino acid sequence differing therefrom by one or several amino acids. In addition, the applicant recognized that the protein also contains a CUB domain which also comprises about 110 amino acids. Moreover, he found that the protein can be present in tumor cells in a form other than that existing in normal cells. The modified form can present itself as additions, substitutions, inversions and/or deletions of one or several amino acids. In particular, the applicant found that the protein may have a deletion of one or several amino acids in medulloblastomas and glioblastomas and in the case of breast cancer.

The present invention refers to the above protein as "a protein containing an SRCR domain" (SRCR protein).

A further subject matter of the present invention relates to a nucleic acid coding for an (SRCR protein). It may be an RNA or a DNA. The latter may be e.g. a genomic DNA or a cDNA. Preferred is a DNA which comprises the following:

(a) the DNA of FIG. 1 (SEQ ID NO:1) or a DNA differing therefrom by one or several base pairs, (b) a DNA hybridizing with the DNA from (a), or (c) a DNA related to the DNA from (a) or (b) via the degenerated genetic code.

The expression "hybridizing DNA" refers to a DNA which hybridizes with a DNA from (a) under normal conditions, particularly at 20° C. below the melting point of the DNA.

The DNA of FIG. 1 (SEQ ID NO:1) was deposited with the DSMZ (Deutsche Sammlung von Mikroorganismen und Zellkulturen Gmbh, Mascheroder Weg 1b, D-38124 Braunschweig, Germany) as HFL2 under deposit accession number DSM11281 on Nov. 8, 1996 under the Budapest Treaty on the International Recognition of the Deposit of Microorganisms for the Purposes of Patent Procedure.

A nucleic acid according to the invention is described below in the form of a DNA, particularly cDNA. It is exemplary for every nucleic acid, particularly DNA, falling under the present invention.

For the production of a cDNA according to the invention it is favorable to use mRNA from human fetal lung as a basis. Such an mRNA is known, it can be purchased e.g. from Clonetech. Full-length CDNA is generated from the mRNA, e.g. via oligodT-priming in combination with Cap-snatching. A person skilled in the art is familiar with the methods and conditions. A cDNA adapter, e.g. from the marathon kit from Clonetech, is ligated to the full-length cDNA in a blunt-end fashion. Then, the cDNA is subjected to a PCR method which uses primer pairs, one primer being specific to the cDNA adapter and the other primer being specific to DNA sequences from known proteins containing an SRCR domain. An example of the latter primer is:

cubf1 5'-TGCACATCTCTGAAGACCACAG-3' (SEQ ID NO:12)

in the 5' direction, and

41nr1 5'-GTGGTCTGCAGGCAGCTG-3' (SEQ ID NO:9)

in the 3' direction.

The 41nr1 primer is localized in a strongly preserved or conserved region of SRCR domains, the cubf1 primer is localized in a strongly preserved region of CUB domains. In accordance with the primer combination, an amplified cDNA is obtained which was amplified in the 5' direction and 3' direction, respectively. The amplified cDNA is hybridized with a labeled DNA probe specific to a nucleic acid according to the invention. Such DNA probes are e.g. the below DNA probes aime2e4f1 and a60kexf2:

DNA probe aime2e4f1: 5'-AGGCCAGATACTTG (SEQ ID NO:10)

DNA probe a60kexf2: 5'-CTTCAGATTACTGAA (SEQ ID NO:11)

A cDNA which hybridizes with the DNA probe aime2e4f1 and was amplified in the 5' direction, is ligated with a cDNA which was amplified in the 3' direction and hybridizes with the DNA probe a60kexf2. The ligation product is a cDNA according to the invention.

A cDNA according to the invention can be present in a vector and expression vector, respectively. A person skilled in the art is familiar with examples thereof. In the case of an expression vector for E. coli these are e.g. pGEMEX, pUC derivatives, pGEX-2T, pET3b and pQE-8, the latter being preferred. For the expression in yeast e.g. pY100 and Ycpad1 have to be mentioned, while e.g. pKCR, pEFBOS, cDM8 and pCEV4 have to be indicated for the expression in animal cells. The bacculovirus expression vector pAcSGHisNT-A is especially suitable for the expression in insect cells.

The person skilled in the art is familiar with suitable cells to express a cDNA according to the invention, which is present in an expression vector. Examples of such cells comprise the E. coli strains HB101, DH1, x1776, JM101, JM109, BL21 and SG13009, the latter being preferred, the yeast strain saccharomyces cerevisiae and the animal cells L, 3T3, FM3A, CHO, COS, Vero and HeLa as well as the insect cells sf9.

The person skilled in the art knows in which way a DNA according to the invention has to be inserted in an expression vector. He is also familiar with the fact that this DNA can be inserted in combination with a DNA coding for another protein and peptide, respectively, so that the cDNA according to the invention can be expressed in the form of a fusion protein.

In addition, the person skilled in the art knows conditions of culturing transformed cells and transfected cells, respectively. He is also familiar with processes of isolating and purifying the protein expressed by the cDNA according to the invention. Thus, such a protein, which may also be a fusion protein, is also a subject matter of the present invention.

A further subject matter of the present invention relates to an antibody directed against an above protein and fusion protein, respectively. Such an antibody can be prepared by common methods. It may be polyclonal and monoclonal, respectively. For its preparation it is favorable to immunize animals—particularly rabbits or chickens for a polyclonal antibody and mice for a monoclonal antibody—with an above (fusion) protein or with fragments thereof. Further "boosters" of the animals can be effected with the same (fusion) protein or with fragments thereof. The polyclonal antibody may then be obtained from the animal serum and egg yolk, respectively. For the preparation of the monoclonal antibody, animal spleen cells are fused with myeloma cells.

The present invention enables to investigate elemental processes of the cell. By means of a nucleic acid according to the invention, particularly a DNA, and primers derived therefrom, it can be determined in mammals, particularly human beings, whether they contain and/or express a gene which codes for an (SRCR protein). It can also be determined in which form the (SRCR protein) is present and which significance the individual forms have for the cell and processes thereof, respectively. For example, the applicant discovered that in medulloblastomas and glioblastomas as well as in breast cancer the (SRCR protein) includes a deletion. This deletion can also be identified on a genomic level. The genomic DNA clones pBa112, pBa74, pBa36, pBa41, PG141BF17, PG141BA10, pBa60, pBa101 and pBa131 are provided which in the listed order indicate a DNA range from 5'->3' (cf. FIGS. 3, 4, and 5) which is present in normal cells but has deletions on both allels in tumor cells, particularly in cells of a medulloblastoma, glioblastoma or breast cancer. Said DNA clones also represent a subject matter of the present invention. They were also deposited with the DSMZ: pBa74 under DSM 11280, pBa36 under DSM 11272, pBa41 under DSM 11278 and pBa60 under DSM 11279, on Nov. 8, 1996 each; and PG141BF17 under DSM 11649, PG141BA10 under DSM 11648, pBa101 under DSM 11646 and pBa131 under DSM 11647, on Jul. 4, 1997 each. In addition to the coding sequence the genomic clones provide intron sequences. They are suitable for mutation analysis in tumors, e.g. as hybridization probes or with primers derived therefrom. The genomic clones thus provide diagnostic agents. For carrying out the above investigations conventional methods such as reverse transcription, PCR reaction, hybridization and sequencing can be used. According to the invention a kit is also provided which contains an above nucleic acid, particularly DNA, and/or primers derived therefrom as well as carriers and conventional auxiliary agents. Moreover, diagnostic steps can be taken with an (SRCR protein) according to the invention. In particular, it can be determined whether autoantibodies exist against such a protein.

Furthermore, the present invention is suitable to interfere with elemental processes of the cell. An (SRCR protein) can be inserted in mammals, particularly human beings. For this purpose, it may be favorable to couple the (SRCR protein) to a protein which is not considered foreign by the respective body, e.g. transferrin or BSA. A nucleic acid according to the invention, particularly a DNA, can also be inserted and expressed in mammals, particularly human beings. For this purpose, it may be favorable to control the expression of the nucleic acid according to the invention by a tissue-specific promoter. The expression of an (SRCR protein) can be controlled and regulated by an antibody according to the invention.

Thus, the present invention represents a great contribution to the diagnostic and therapeutic detection of elemental processes of the cell. In particular, tumoral diseases, particularly of the central nervous system, e.g. medulloblastomas or glioblastomas, as well as the breast can be diagnosed on a genetic level and steps can be taken thereagainst. The diagnostic detection of elemental processes of the cell cannot only be made postnatally but also already prenatally in this connection.

BRIEF DESCRIPTION OF THE DRAWINGS

FIG. 1 shows the base sequence (SEQ ID NO:1) and the amino acid sequence (SEQ ID NO:2), derived therefrom, of an (SRCR protein) according to the invention, FIG. 2 shows the base sequence (SEQ ID NO:3) and the amino acid sequence (SEQ ID NO:4) derived therefrom, comprised by an (SRCR protein) according to the invention, the above FIG. 1 representing a section of FIG. 2 (nucleotides 2958 to 4957), FIG. 5 shows the sequence of sequence ranges SC1 (SEQ ID NO:5), SC2 (SEQ ID NO:6), SC3 (SEQ ID NO:7) and SC4 (SEQ ID NO:8) (FIGS. 5(*a*), (*b*), (*c*), (*d*)). Furthermore, a range is marked in SC4 by underlining, which codes for a transmembrane domain.

Figure 3:
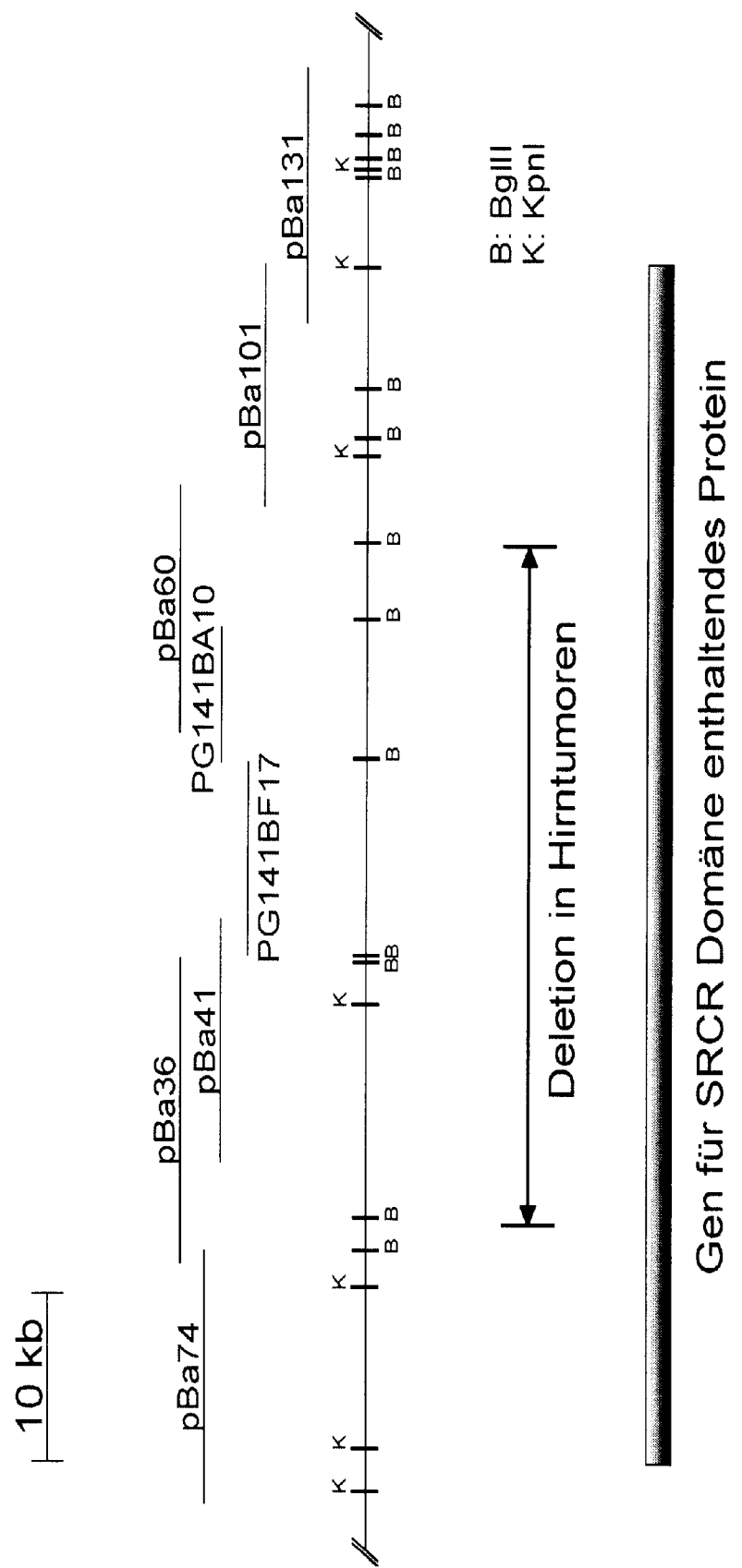
FIG. 3 shows the restriction map and the relation of the genomic clones pBA74, pBa36, pBa41, PG141BF17, PG141BA10, pBa60, pBa101 and pBa131 with respect to one another.
Figure 4:
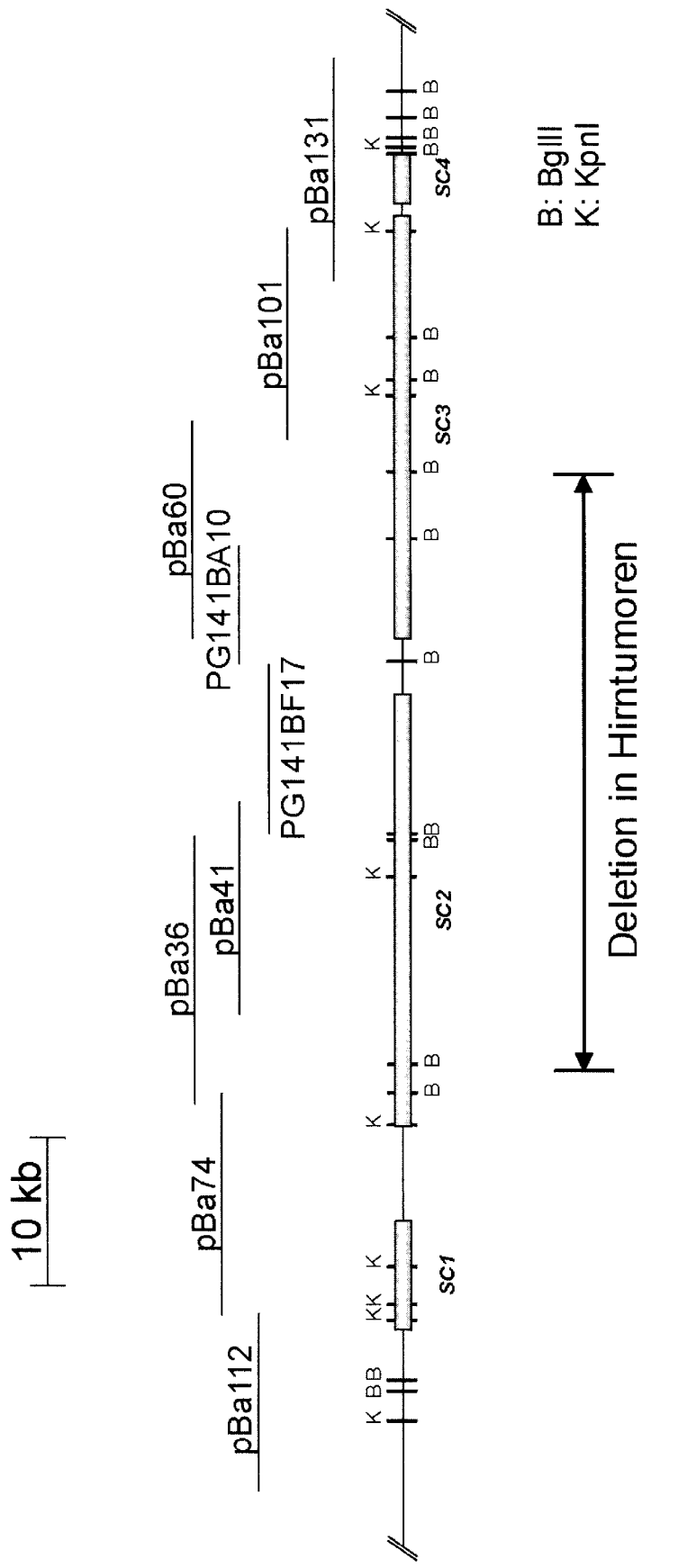
FIG. 4 shows the restriction map and the relation of the genomic clones pBa112, pBA74, pBa36, pBa41, PG141BF17, PG141BA10, pBa60, pBa101 and pBa131 with respect to one another. Furthermore, the sequence ranges SC1, SC2, SC3 and SC4 comprised by these clones are indicated.

The present invention is explained by the below examples.

EXAMPLE 1

Preparation and Purification of an (SRCR Protein) According to the Invention

For preparing an (SRCR protein) according to the invention, an mRNA from human fetal lung (Clonetech) was used. Full-length cDNA was prepared from the mRNA, oligodT priming being carried out in combination with "Cap snatching". A cDNA adapter from the marathon kit from Clonetech was ligated to the full-length cDNA in blunt-end fashion. The cDNA was then subjected to a PCR method. The primer pairs used were:

cubf1 5'-TGCACATCTCTGAAGACCACAG-3' (SEQ ID NO:12)

in the 5' direction and

41nr1 5'-GTGGTCTGCAGGCAGCTG-3' (SEQ ID NO:9)

in the 3' direction, respectively, each in combination with a primer specific to the cDNA adapter.

The PCR batch and PCR conditions were as follows:
PCR Batch

Template DNA: 1 $\mu$l=10 ng

10×TaKARa long-range PCR buffer: 2.5 $\mu$l $MgCl_2$ (25 mM): 2.5 $\mu$l

Taq/Pfu polymerase mix (19:1): 0.25 μl
dNTP mix (10 mM each): 1 μl
oligonucleotides (10 pmol/μl): 1 μl
H$_2$O bidist.: ad 25 μl
PCR Conditions

| | | |
|---|---|---|
| 95° C. | 3 min. | 1 cycle |
| 94° C. | 15 sec. | |
| 60° C. | 10 sec. | |
| 68° C. | 4 min. | 15 cycles |
| 94° C. | 15 sec. | |
| 60° C. | 10 sec. | |
| 68° C. | 4 min. | 10 cycles having an extension of 10 sec. of the 68° C. step each per cycle |

The amplified cDNA was subjected to hybridization with the above-indicated DNA probes aime2e4f1 and a60kexf2. Their sequences are specific to the above-mentioned genomic DNA clone pBa60. cDNA was identified which hybridized with the DNA probes. This cDNA had been amplified in the 5' direction and 3' direction, respectively. The cDNA was purified over an agarose gel electrophoresis and cleaved by SwaI. After another agarose gel electrophoresis, a cDNA amplified in the 5' direction was ligated with one amplified in the 3' direction. The ligation product was sequenced. It comprised the DNA of FIG. 1. The ligation product was cleaved by NotI and inserted in the expression vector pQE-30 NST (Quiagen company) cleaved by NotI. The expression plasmid pQ/SRCR protein was obtained. Such a protein codes for a fusion protein from 6 histidine residues (N terminus partner) and an (SRCR protein) according to the invention (C terminus partner). pQ/SRCR protein was used for the transformation of E. coli SG 13009 (cf. Gottesman, S. et al., J. bacteriol. 148 (1981), 265–273). The bacteria were cultured in an LB broth with 100 μg/ml ampicillin and 25 μg/ml kanamycin and induced with 60 μM isopropyl-β-D-thiogalactopyranoside (IPTG) for 4 h. By the addition of 6 M guanidine hydrochloride, lysis of the bacteria was achieved, then a chromatography (Ni-NTA resin) was carried out with the lysate in the presence of 8 M urea in accordance with the instructions from the manufacturer (Diagen company) of the chromatography material. The bound fusion protein was eluted in a buffer having a pH of 3.5. After its neutralization, the fusion protein was subjected to 18% SDS polyacrylamide gel electrophoresis and stained using coomassie blue (cf. Thomas, J. O. and Kornberg, R. D., J. Mol. Biol. 149 (1975), 709–733).

It showed that a (fusion) protein according to the invention can be prepared in highly pure form.

EXAMPLE 2
Preparation and Detection of an Antibody According to the Invention

A fusion protein of Example 1 according to the invention was subjected to 18% SDS polyacrylamide gel electrophoresis. After staining the gel with 4 M sodium acetate, an about 260 kD band was cut out of the gel and incubated in phosphate-buffered common salt solution. Gel pieces were sedimented before the protein concentration of the supernatant was determined by SDS polyacrylamide gel electrophoresis which was followed by coomassie blue staining. Animals were immunized with the gel-purified fusion protein as follows:

Immunization Protocol For Polyclonal Antibodies in Rabbits

35 μg of gel-purified fusion protein in 0.7 ml PBS and 0.7 ml of complete Freund's adjuvant and incomplete Freund's adjuvant, respectively, were used per immunization:

Day 0: 1$^{st}$ immunization (complete Freund's adjuvant)

Day 14: 2$^{nd}$ immunization (incomplete Freund's adjuvant; icFA)

Day 28: 3$^{rd}$ immunization (icFA)

Day 56: 4$^{th}$ immunization (icFA)

Day 80: bleeding to death.

The rabbit serum was tested in an immunoblot. For this purpose, a fusion protein of Example 1 according to the invention was subjected to SDS polyacrylamide gel electrophoresis and transferred to a nitrocellulose filter (cf. Khyse-Andersen, J., J. Biochem. Biophys. Meth. 10 (1984), 203–209). The Western blot analysis was carried out as described in Bock, C.-T. et al., Virus Genes 8, (1994), 215–229. For this purpose, the nitrocellulose filter was incubated with a first antibody at 37° C. for one hour. This antibody was the rabbit serum (1:10000 in PBS). After several wash steps using PBS, the nitrocellulose filter was incubated with a second antibody. This antibody was an alkaline phosphatase-coupled monoclonal goat anti-rabbit IgG antibody (Dianova company) (1:5000) in PBS. 30 minutes of incubation at 37° C. were followed by several wash steps using PBS and subsequently by the alkaline phosphatase detection reaction with developer solution (36 μM 5'-bromo-4-chloro-3-indolylphosphate, 400 μM nitro blue tetrazolium, 100 mM Tris-HCl, pH 9.5, 100 mM NaCl, 5 mM MgCl$_2$) at room temperature until bands were visible.

It showed that polyclonal antibodies according to the invention can be prepared.

Immunization Protocol For Polyclonal Antibodies in Chickens

40 μg of gel-purified fusion protein in 0.8 ml PBS and 0.8 ml of complete Freund's adjuvant and incomplete Freund's adjuvant, respectively, were used per immunization.

Day 0: 1$^{st}$ immunization (complete Freund's adjuvant)

Day 28: 2$^{nd}$ immunization (incomplete Freund's adjuvant; icFA)

Day 50: 3$^{rd}$ immunization (icFA)

Antibodies were extracted from egg yolk and tested in a Western blot. Polyclonal antibodies according to the invention were detected.

Immunization Protocol For Monoclonal Antibodies in Mice

12 μg of gel-purified fusion protein in 0.25 ml PBS and 0.25 ml of complete Freund's adjuvant and incomplete Freund's adjuvant, respectively, were used per immunization. The fusion protein was dissolved in 0.5 ml (without adjuvant) in the 4$^{th}$ immunization.

Day 0: 1$^{st}$ immunization (complete Freund's adjuvant)

Day 28: 2$^{nd}$ immunization (incomplete Freund's adjuvant; icFA)

Day 56: 3$^{rd}$ immunization (icFA)

Day 84: 4$^{th}$ immunization (PBS)

Day 87: fusion.

Supernatants of hybridomas were tested in a Western blot. Monoclonal antibodies according to the invention were detected.

What is claimed is:

1. A protein comprising a Scavenger Receptor Cysteine Rich domain, wherein the protein comprises the amino acid sequence of SEQ ID NO: 1.

2. A protein comprising a Scavenger Receptor Cysteine Rich domain according to claim 1, wherein the protein comprises the amino acid sequence of SEQ ID NO: 3.

3. A method of producing a protein comprising a Scavenger Receptor Cysteine Rich domain, the method comprising culturing a transformant that expresses a protein comprising the amino acid sequence of SEQ ID NO: 1.

4. A method of producing a protein comprising a Scavenger Receptor Cysteine Rich domain, the method comprising culturing a transformant that expresses a protein comprising the amino acid sequence of SEQ ID NO: 3.

5. The protein of claim 1, wherein the protein is a fusion protein comprising the Scavenger Receptor Cysteine Rich domain.

6. The protein of claim 2, wherein the protein is a fusion protein comprising the Scavenger Receptor Cysteine Rich domain.

7. The protein of claim 1 consisting of the amino acid sequence of SEQ ID NO: 1.

8. The polypeptide of claim 2 consisting of the amino acid sequence of SEQ ID NO: 3.

9. A fusion protein comprising a Scavenger Receptor Cysteine Rich domain, wherein the fusion protein is a product of a bacterial culture deposited with the *Deutche Sammlung von Mikroorganismen und Zellkulturen* under Accession No. DSM 11281.

10. A polypeptide comprising a Scavenger Receptor Cysteine Rich domain selected from the Scavenger Receptor Cysteine Rich domains of SEQ ID NOS: 1 or SEQ ID NO: 3, wherein the polypeptide binds to an antibody which also binds to a Scavenger Receptor Cysteine Rich domain of a fusion protein, which is a product of a bacterial culture deposited with the *Deutche Sammlung von Mikroorganismen und Zellkulturen* under Accession No. DSM 11281.

11. A fusion protein comprising a Scavenger Receptor Cysteine Rich protein, which is a product of a bacterial culture deposited with the *Deutche Sammlung von Mikroorganismen und Zellkulturen* under an Accession No. selected from the group consisting of: DSM 11280, DSM 11277, DSM 11278, DSM 11279, DSM 11646, DSM 11647, DSM 11648 and DSM 11649.

12. The fusion protein of claim 11, wherein the Scavenger Receptor Cysteine Rich protein is deposited under Accession No. DSM 11280.

13. The fusion protein of claim 12, wherein the bacterial culture is deposited under Accession No. DSM 11277.

14. The fusion protein of claim 12, wherein the bacterial culture is deposited under Accession No. DSM 11278.

15. The fusion protein of claim 12, wherein the bacterial culture is deposited under Accession No. DSM 11279.

16. The fusion protein of claim 12, wherein the bacterial culture is deposited under Accession No. DSM 11646.

17. The fusion protein of claim 12, wherein the bacterial culture is deposited under Accession No. DSM 11647.

18. The fusion protein of claim 12, wherein the bacterial culture protein is deposited under Accession No. DSM 11648.

19. The fusion protein of claim 12, wherein the bacterial culture is deposited under Accession No. DSM 11649.

* * * * *

SEQUENCE LISTING

<160> NUMBER OF SEQ ID NOS: 12

<210> SEQ ID NO 1
<211> LENGTH: 666
<212> TYPE: PRT
<213> ORGANISM: Homo sapiens

<400> SEQUENCE: 1

```
Gly His Glu Ser Tyr Leu Trp Ser Cys Pro His Asn Gly Trp Leu Ser
 1               5                  10                  15

His Asn Cys Gly His His Glu Asp Ala Gly Val Ile Cys Ser Ala Ala
            20                  25                  30

Gln Ser Gln Ser Thr Pro Arg Pro Asp Thr Trp Leu Thr Thr Asn Leu
        35                  40                  45

Pro Ala Leu Thr Val Gly Ser Glu Ser Ser Leu Ala Leu Arg Leu Val
    50                  55                  60

Asn Gly Gly Asp Arg Cys Arg Gly Arg Val Glu Val Leu Tyr Arg Gly
65                  70                  75                  80

Ser Trp Gly Thr Val Cys Asp Asp Ser Trp Asp Thr Asn Asp Ala Asn
                85                  90                  95

Val Val Cys Arg Gln Leu Gly Cys Gly Trp Ala Met Ser Ala Pro Gly
            100                 105                 110

Asn Ala Arg Phe Gly Gln Gly Ser Gly Pro Ile Val Leu Asp Asp Val
            115                 120                 125

Arg Cys Ser Gly Asn Glu Ser Tyr Leu Trp Ser Cys Pro His Lys Gly
        130                 135                 140

Trp Leu Thr His Asn Cys Gly His His Glu Asp Ala Gly Val Ile Cys
145                 150                 155                 160

Ser Ala Thr Gln Ile Asn Ser Thr Thr Thr Asp Trp Trp His Pro Thr
                165                 170                 175

Thr Thr Thr Thr Ala Arg Pro Ser Ser Asn Cys Gly Gly Phe Leu Phe
            180                 185                 190

Tyr Ala Ser Gly Thr Phe Ser Ser Pro Ser Tyr Pro Ala Tyr Tyr Pro
            195                 200                 205

Asn Asn Ala Lys Cys Val Trp Glu Ile Glu Val Asn Ser Gly Tyr Arg
        210                 215                 220

Ile Asn Leu Gly Phe Ser Asn Leu Lys Leu Glu Ala His His Asn Cys
225                 230                 235                 240

Ser Phe Asp Tyr Val Glu Ile Phe Asp Gly Ser Leu Asn Ser Ser Leu
                245                 250                 255

Leu Leu Gly Lys Ile Cys Asn Asp Thr Arg Gln Ile Phe Thr Ser Ser
            260                 265                 270

Tyr Asn Arg Met Thr Ile His Phe Arg Ser Asp Ile Ser Phe Gln Asn
            275                 280                 285

Thr Gly Phe Leu Ala Trp Tyr Asn Ser Phe Pro Ser Asp Ala Thr Leu
        290                 295                 300

Arg Leu Val Asn Leu Asn Ser Ser Tyr Gly Leu Cys Ala Gly Arg Val
305                 310                 315                 320

Glu Ile Tyr His Gly Gly Thr Trp Gly Thr Val Cys Asp Asp Ser Trp
                325                 330                 335

Thr Ile Gln Glu Ala Glu Val Val Cys Arg Gln Leu Gly Cys Gly Arg
            340                 345                 350

Ala Val Ser Ala Leu Gly Asn Ala Tyr Phe Gly Ser Gly Ser Gly Pro
```

```
            355                 360                 365
Ile Thr Leu Asp Asp Val Glu Cys Ser Gly Thr Glu Ser Thr Leu Trp
            370                 375                 380

Gln Cys Arg Asn Arg Gly Trp Phe Ser His Asn Cys Asn His Arg Glu
385                 390                 395                 400

Asp Ala Gly Val Ile Cys Ser Gly Asn His Leu Ser Thr Pro Ala Pro
            405                 410                 415

Phe Leu Asn Ile Thr Arg Pro Asn Thr Asp Tyr Ser Cys Gly Gly Phe
            420                 425                 430

Leu Ser Gln Pro Ser Gly Asp Phe Ser Ser Pro Phe Tyr Pro Gly Asn
            435                 440                 445

Tyr Pro Asn Asn Ala Lys Cys Val Trp Asp Ile Glu Val Gln Asn Asn
            450                 455                 460

Tyr Arg Val Thr Val Ile Phe Arg Asp Val Gln Leu Glu Gly Gly Cys
465                 470                 475                 480

Asn Tyr Asp Tyr Ile Glu Val Phe Asp Gly Pro Tyr Arg Ser Ser Pro
            485                 490                 495

Leu Ile Ala Arg Val Cys Asp Gly Ala Arg Gly Ser Phe Thr Ser Ser
            500                 505                 510

Ser Asn Phe Met Ser Ile Arg Phe Ile Ser Asp His Ser Ile Thr Arg
            515                 520                 525

Arg Gly Phe Arg Ala Glu Tyr Tyr Ser Ser Pro Ser Asn Asp Ser Thr
            530                 535                 540

Asn Leu Leu Cys Leu Pro Asn His Met Gln Ala Ser Val Ser Arg Ser
545                 550                 555                 560

Tyr Leu Gln Ser Leu Gly Phe Ser Ala Ser Asp Leu Val Ile Ser Thr
            565                 570                 575

Trp Asn Gly Tyr Tyr Glu Cys Arg Pro Gln Ile Thr Pro Asn Leu Val
            580                 585                 590

Ile Phe Thr Ile Pro Tyr Ser Gly Cys Gly Thr Phe Lys Gln Ala Asp
            595                 600                 605

Asn Asp Thr Ile Asp Tyr Ser Asn Phe Leu Thr Ala Ala Val Ser Gly
            610                 615                 620

Gly Ile Ile Lys Arg Arg Thr Asp Leu Arg Ile His Val Ser Cys Arg
625                 630                 635                 640

Met Leu Gln Asn Thr Trp Val Asp Thr Met Tyr Ile Ala Asn Asp Thr
            645                 650                 655

Ile His Val Ala Asn Asn Thr Ile Gln Val
            660                 665

<210> SEQ ID NO 2
<211> LENGTH: 2001
<212> TYPE: DNA
<213> ORGANISM: Homo sapiens

<400> SEQUENCE: 2
ggacacgagt cttawabcct gtggagctgc ccccacaatg ctggctctc ccacaactgt      60 ggccatcatg aagatgctgg tgtcatctgc tcagctgctc agtcccagtc aacgcccagg    120
ccagatactt ggctgaccac caacttaccg gcattgacag taggatctga atccagtttg    180
gctctgaggc tggtgaatgg aggtgacagg tgtcgaggcc gagtggaggt cctgtatcga    240
ggctcctggg gaaccgtgtg tgatgacagc tgggacacca atgatgccaa tgtggtctgc    300
aggcagctgg gctgtggctg ggccatgtcg gccccaggaa atgcccggtt tggccagggc    360
```

-continued

```
tcaggaccca ttgtcctgga tgatgtgcgc tgctcaggga atgagtccta cctgtggagc      420
tgcccccaca aaggctggct cacccacaac tgtggccatc acgaagacgc tggtgtcatc      480
tgctcagcca cccaaataaa ttctactacg acagattggt ggcatccaac aactacaacc      540
actgcaagac cctcttcaaa ttgtggtggc ttcttattct atgccagtgg gacattctcc      600
agcccatcct accctgcata ctaccccaac aatgctaagt gtgtttggga atagaagtg       660 aattctggtt atcgcataaa cctgggcttc agtaatctga aattggaggc acaccataac      720
tgcagttttg attatgttga aatctttgat ggatcattga atagcagtct cctgctgggg      780
aaaatctgta atgataccag gcaaatattt acatcttctt acaaccgaat gaccattcac      840
tttcgaagtg acatcagttt ccaaaacact ggcttttttgg cttggtataa ctccttccca     900
agcgatgcca ccttgaggtt ggtcaattta aattcatcct atggtctatg tgccgggcgt      960
gtagaaattt accatggtgg cacctggggg acagtttgtg atgactcctg gaccattcag      1020
gaagctgagg tggtctgcag acagctaggg tgtggacgtg cagtttcagc ccttggaaat     1080
gcatattttg gctctggctc tggccccatc accctggacg atgtagagtg ctcagggacg     1140
gaatccactc tctggcagtg ccggaaccga ggctggttct cccacaactg taatcatcgt     1200
gaagatgctg tgtcatctg ctcaggaaac catctatcga cacctgctcc ttttctcaac      1260
atcacccgtc aaacacaga ttattcctgc ggaggcttcc tatcccaacc atcagggac       1320 ttttccagcc cattctatcc cgggaactat ccaaacaatg ccaagtgtgt gtgggacatt     1380
gaggtgcaaa acaactaccg tgtgactgtg atcttcagag atgtccagct gaaggtggc      1440 tgcaactatg attatattga agttttcgat ggcccctacc gcagttcccc tctcattgct     1500
cgagtttgtg atggggccag aggctccttc acttcttcct ccaacttcat gtccattcgc    1560
ttcatcagtg accacagcat cacaaggaga gggttccggg ctgagtacta ctccagtccc    1620
tccaatgaca gcaccaacct gctctgtctg ccaaatcaca tgcaagccag tgtgagcagg    1680
agctatctcc aatccttggg cttttctgcc agtgaccttg tcatttccac ctggaatgga     1740
tactacgagt gtcggcccca gataacgccg aacctggtga tattcacaat tcctactca    1800 ggctgcggca ccttcaagca ggcagacaat gacaccatcg actattccaa cttcctcaca    1860
gcagctgtct caggtggcat catcaagagg aggacagacc tccgtattca cgtcagctgc    1920
agaatgcttc agaacacctg ggtcgacacc atgtacattg ctaatgacac catccacgtt    1980
gctaataaca ccatccaggt c                                              2001
```

<210> SEQ ID NO 3
<211> LENGTH: 1785
<212> TYPE: PRT
<213> ORGANISM: Homo sapiens

<400> SEQUENCE: 3

```
Met Gly Ile Ser Thr Val Ile Leu Glu Met Cys Leu Leu Trp Gly Gln
 1               5                  10                  15

Val Leu Ser Thr Gly Gly Trp Ile Pro Arg Thr Thr Asp Tyr Ala Ser
            20                  25                  30

Leu Ile Pro Ser Glu Val Pro Leu Asp Gln Thr Val Ala Glu Gly Ser
        35                  40                  45

Pro Phe Pro Ser Glu Ser Thr Leu Glu Ser Thr Ala Ala Glu Gly Ser
    50                  55                  60

Pro Ile Ser Leu Glu Ser Thr Leu Glu Ser Thr Val Ala Glu Gly Ser
65                  70                  75                  80
```

```
Leu Ile Pro Ser Glu Ser Thr Leu Ser Thr Val Ala Glu Gly Ser
                85                  90                  95

Asp Ser Gly Leu Ala Leu Arg Leu Val Asn Gly Asp Gly Arg Cys Gln
            100                 105                 110

Gly Arg Val Glu Ile Leu Tyr Arg Gly Ser Trp Gly Thr Val Cys Asp
        115                 120                 125

Asp Ser Trp Asp Thr Asn Asp Ala Asn Val Val Cys Arg Gln Leu Gly
130                 135                 140

Cys Gly Trp Ala Met Ser Ala Pro Gly Asn Ala Trp Phe Gly Gln Gly
145                 150                 155                 160

Ser Gly Pro Ile Ala Leu Asp Asp Val Arg Cys Ser Gly His Glu Ser
                165                 170                 175

Tyr Leu Trp Ser Cys Pro His Asn Gly Trp Leu Ser His Asn Cys Gly
            180                 185                 190

His Gly Glu Asp Ala Gly Val Ile Cys Ser Ala Ala Gln Pro Gln Ser
        195                 200                 205

Thr Leu Arg Pro Glu Ser Trp Pro Val Arg Ile Ser Pro Val Pro
    210                 215                 220

Thr Glu Gly Ser Glu Ser Ser Leu Ala Leu Arg Leu Val Asn Gly Gly
225                 230                 235                 240

Asp Arg Cys Arg Gly Arg Val Glu Val Leu Tyr Arg Gly Ser Trp Gly
                245                 250                 255

Thr Val Cys Asp Asp Tyr Trp Asp Thr Asn Asp Ala Asn Val Val Cys
            260                 265                 270

Arg Gln Leu Gly Cys Gly Trp Ala Met Ser Ala Pro Gly Asn Ala Gln
        275                 280                 285

Phe Gly Gln Gly Ser Gly Pro Ile Val Leu Asp Asp Val Arg Cys Ser
    290                 295                 300

Gly His Glu Ser Tyr Leu Trp Ser Cys Pro His Asn Gly Trp Leu Thr
305                 310                 315                 320

His Asn Cys Gly His Ser Glu Asp Ala Gly Val Ile Cys Ser Ala Pro
                325                 330                 335

Gln Ser Arg Pro Thr Pro Ser Pro Asp Thr Trp Pro Thr Ser His Ala
            340                 345                 350

Ser Thr Ala Gly Pro Glu Ser Ser Leu Ala Leu Arg Leu Val Asn Gly
        355                 360                 365

Gly Asp Arg Cys Gln Gly Arg Val Glu Val Leu Tyr Arg Gly Ser Trp
370                 375                 380

Gly Thr Val Cys Asp Asp Ser Trp Asp Thr Ser Asp Ala Asn Val Val
385                 390                 395                 400

Cys Arg Gln Leu Gly Cys Gly Trp Ala Thr Ser Ala Pro Gly Asn Ala
                405                 410                 415

Arg Phe Gly Gln Gly Ser Gly Pro Ile Val Leu Asp Asp Val Arg Cys
            420                 425                 430

Ser Gly Tyr Glu Ser Tyr Leu Trp Ser Cys Pro His Asn Gly Trp Leu
        435                 440                 445

Ser His Asn Cys Gln His Ser Glu Asp Ala Gly Val Ile Cys Ser Ala
    450                 455                 460

Ala His Ser Trp Ser Thr Pro Ser Pro Asp Thr Leu Pro Thr Ile Thr
465                 470                 475                 480

Leu Pro Ala Ser Thr Val Gly Ser Glu Ser Ser Leu Ala Leu Arg Leu
                485                 490                 495

Val Asn Gly Gly Asp Arg Cys Gln Gly Arg Val Glu Val Leu Tyr Gln
```

-continued

```
                    500                 505                 510
Gly Ser Trp Gly Thr Val Cys Asp Asp Ser Trp Asp Thr Asn Asp Ala
            515                 520                 525
Asn Val Val Cys Arg Gln Pro Gly Cys Gly Trp Ala Met Ser Ala Pro
            530                 535                 540
Gly Asn Ala Arg Phe Gly Gln Gly Ser Gly Pro Ile Val Leu Asp Asp
545                 550                 555                 560
Val Arg Cys Ser Gly His Glu Ser Tyr Pro Trp Ser Cys Pro His Asn
                565                 570                 575
Gly Trp Leu Ser His Asn Cys Gly His Ser Glu Asp Ala Gly Val Ile
                580                 585                 590
Cys Ser Ala Ser Gln Ser Arg Pro Thr Pro Ser Pro Asp Thr Trp Pro
            595                 600                 605
Thr Ser His Ala Ser Thr Ala Gly Ser Glu Ser Ser Leu Ala Leu Arg
            610                 615                 620
Leu Val Asn Gly Gly Asp Arg Cys Gln Gly Arg Val Glu Val Leu Tyr
625                 630                 635                 640
Arg Gly Ser Trp Gly Thr Val Cys Asp Asp Tyr Trp Asp Thr Asn Asp
                645                 650                 655
Ala Asn Val Val Cys Arg Gln Leu Gly Cys Gly Trp Ala Met Ser Ala
                660                 665                 670
Pro Gly Asn Ala Arg Phe Gly Gln Gly Ser Gly Pro Ile Val Leu Asp
            675                 680                 685
Asp Val Arg Cys Ser Gly His Glu Ser Tyr Leu Trp Ser Cys Pro His
            690                 695                 700
Asn Gly Trp Leu Ser His Asn Cys Gly His His Glu Asp Ala Gly Val
705                 710                 715                 720
Ile Cys Ser Ala Ser Gln Ser Gln Pro Thr Pro Ser Pro Asp Thr Trp
                725                 730                 735
Pro Thr Ser His Ala Ser Thr Ala Gly Ser Glu Ser Ser Leu Ala Leu
                740                 745                 750
Arg Leu Val Asn Gly Gly Asp Arg Cys Gln Gly Arg Val Glu Val Leu
            755                 760                 765
Tyr Arg Gly Ser Trp Gly Thr Val Cys Asp Asp Tyr Trp Asp Thr Asn
            770                 775                 780
Asp Ala Asn Val Val Cys Arg Gln Leu Gly Cys Gly Trp Ala Thr Ser
785                 790                 795                 800
Ala Pro Gly Asn Ala Arg Phe Gly Gln Gly Ser Gly Pro Ile Val Leu
                805                 810                 815
Asp Asp Val Arg Cys Ser Gly His Glu Ser Tyr Leu Trp Ser Cys Pro
                820                 825                 830
His Asn Gly Trp Leu Ser His Asn Cys Gly His His Glu Asp Ala Gly
            835                 840                 845
Val Ile Cys Ser Ala Ser Gln Ser Gln Pro Thr Pro Ser Pro Asp Thr
            850                 855                 860
Trp Pro Thr Ser Arg Ala Ser Thr Ala Gly Ser Glu Ser Thr Leu Ala
865                 870                 875                 880
Leu Arg Leu Val Asn Gly Gly Asp Arg Cys Arg Gly Arg Val Glu Val
                885                 890                 895
Leu Tyr Gln Gly Ser Trp Gly Thr Val Cys Asp Asp Tyr Trp Asp Thr
                900                 905                 910
Asn Asp Ala Asn Val Val Cys Arg Gln Leu Gly Cys Gly Trp Ala Met
            915                 920                 925
```

-continued

```
Ser Ala Pro Gly Asn Ala Gln Phe Gly Gln Gly Ser Gly Pro Ile Val
    930                 935                 940
Leu Asp Asp Val Arg Cys Ser Gly His Glu Ser Tyr Leu Trp Ser Cys
945                 950                 955                 960
Pro His Asn Gly Trp Leu Ser His Asn Cys Gly His His Glu Asp Ala
                965                 970                 975
Gly Val Ile Cys Ser Ala Ala Gln Ser Gln Ser Thr Pro Arg Pro Asp
            980                 985                 990
Thr Trp Leu Thr Thr Asn Leu Pro Ala Leu Thr Val Gly Ser Glu Ser
        995                 1000                1005
Ser Leu Ala Leu Arg Leu Val Asn Gly Gly Asp Arg Cys Arg Gly Arg
    1010                1015                1020
Val Glu Val Leu Tyr Arg Gly Ser Trp Gly Thr Val Cys Asp Asp Ser
1025                1030                1035                1040
Trp Asp Thr Asn Asp Ala Asn Val Val Cys Arg Gln Leu Gly Cys Gly
                1045                1050                1055
Trp Ala Met Ser Ala Pro Gly Asn Ala Arg Phe Gly Gln Gly Ser Gly
            1060                1065                1070
Pro Ile Val Leu Asp Asp Val Arg Cys Ser Gly Asn Glu Ser Tyr Leu
        1075                1080                1085
Trp Ser Cys Pro His Lys Gly Trp Leu Thr His Asn Cys Gly His His
    1090                1095                1100
Glu Asp Ala Gly Val Ile Cys Ser Ala Thr Gln Ile Asn Ser Thr Thr
1105                1110                1115                1120
Thr Asp Trp Trp His Pro Thr Thr Thr Thr Ala Arg Pro Ser Ser
                1125                1130                1135
Asn Cys Gly Gly Phe Leu Phe Tyr Ala Ser Gly Thr Phe Ser Ser Pro
            1140                1145                1150
Ser Tyr Pro Ala Tyr Tyr Pro Asn Asn Ala Lys Cys Val Trp Glu Ile
        1155                1160                1165
Glu Val Asn Ser Gly Tyr Arg Ile Asn Leu Gly Phe Ser Asn Leu Lys
    1170                1175                1180
Leu Glu Ala His His Asn Cys Ser Phe Asp Tyr Val Glu Ile Phe Asp
1185                1190                1195                1200
Gly Ser Leu Asn Ser Ser Leu Leu Gly Lys Ile Cys Asn Asp Thr
                1205                1210                1215
Arg Gln Ile Phe Thr Ser Ser Tyr Asn Arg Met Thr Ile His Phe Arg
            1220                1225                1230
Ser Asp Ile Ser Phe Gln Asn Thr Gly Phe Leu Ala Trp Tyr Asn Ser
        1235                1240                1245
Phe Pro Ser Asp Ala Thr Leu Arg Leu Val Asn Leu Asn Ser Ser Tyr
    1250                1255                1260
Gly Leu Cys Ala Gly Arg Val Glu Ile Tyr His Gly Gly Thr Trp Gly
1265                1270                1275                1280
Thr Val Cys Asp Asp Ser Trp Ser Ile Gln Glu Ala Glu Val Val Cys
                1285                1290                1295
Arg Gln Leu Gly Cys Gly Arg Ala Val Ser Ala Leu Gly Asn Ala Tyr
            1300                1305                1310
Phe Gly Ser Gly Ser Gly Pro Ile Thr Leu Asp Asp Val Glu Cys Ser
        1315                1320                1325
Gly Thr Glu Ser Thr Leu Trp Gln Cys Arg Asn Arg Gly Trp Phe Ser
    1330                1335                1340
```

```
His Asn Cys Asn His Arg Glu Asp Ala Gly Val Ile Cys Ser Gly Asn
1345                1350                1355                1360

His Leu Ser Thr Pro Ala Pro Phe Leu Asn Ile Thr Arg Pro Asn Thr
            1365                1370                1375

Asp Tyr Ser Cys Gly Gly Phe Leu Ser Gln Pro Ser Gly Asp Phe Ser
        1380                1385                1390

Ser Pro Phe Tyr Pro Gly Asn Tyr Pro Asn Asn Ala Lys Cys Val Trp
    1395                1400                1405

Asp Ile Glu Val Gln Asn Asn Tyr Arg Val Thr Val Ile Phe Arg Asp
1410                1415                1420

Val Gln Leu Glu Gly Gly Cys Asn Tyr Asp Tyr Ile Glu Val Phe Asp
1425                1430                1435                1440

Gly Pro Tyr Arg Ser Ser Pro Leu Ile Ala Arg Val Cys Asp Gly Ala
            1445                1450                1455

Arg Gly Ser Phe Thr Ser Ser Asn Phe Met Ser Ile Arg Phe Ile
        1460                1465                1470

Ser Asp His Ser Ile Thr Arg Arg Gly Phe Arg Ala Glu Tyr Tyr Ser
    1475                1480                1485

Ser Pro Ser Asn Asp Ser Thr Asn Leu Leu Cys Leu Pro Asn His Met
1490                1495                1500

Gln Ala Ser Val Ser Arg Ser Tyr Leu Gln Ser Leu Gly Phe Ser Ala
1505                1510                1515                1520

Ser Asp Leu Val Ile Ser Thr Trp Asn Gly Tyr Tyr Glu Cys Arg Pro
            1525                1530                1535

Gln Ile Thr Pro Asn Leu Val Ile Phe Thr Ile Pro Tyr Ser Gly Cys
        1540                1545                1550

Gly Thr Phe Lys Gln Ala Asp Asn Asp Thr Ile Asp Tyr Ser Asn Phe
    1555                1560                1565

Leu Thr Ala Ala Val Ser Gly Gly Ile Ile Lys Arg Arg Thr Asp Leu
    1570                1575                1580

Arg Ile His Val Ser Cys Arg Met Leu Gln Asn Thr Trp Val Asp Thr
1585                1590                1595                1600

Met Tyr Ile Ala Asn Asp Thr Ile His Val Ala Asn Asn Thr Ile Gln
            1605                1610                1615

Val Glu Glu Val Gln Tyr Gly Asn Phe Asp Val Asn Ile Ser Phe Tyr
        1620                1625                1630

Thr Ser Ser Ser Phe Leu Tyr Pro Val Thr Ser Arg Pro Tyr Tyr Val
    1635                1640                1645

Asp Leu Asn Gln Asp Leu Tyr Val Gln Ala Glu Ile Leu His Ser Asp
    1650                1655                1660

Ala Val Leu Thr Leu Phe Val Asp Thr Cys Val Ala Ser Pro Tyr Ser
1665                1670                1675                1680

Asn Asp Phe Thr Ser Leu Thr Tyr Asp Leu Ile Arg Ser Gly Cys Val
            1685                1690                1695

Arg Asp Asp Thr Tyr Gly Pro Tyr Ser Ser Pro Ser Leu Arg Ile Ala
        1700                1705                1710

Arg Phe Arg Phe Arg Ala Phe His Phe Leu Asn Arg Phe Pro Ser Val
    1715                1720                1725

Tyr Leu Arg Cys Lys Met Val Val Cys Arg Ala Tyr Asp Pro Ser Ser
    1730                1735                1740

Arg Cys Tyr Arg Gly Cys Val Leu Arg Ser Lys Arg Asp Val Gly Ser
1745                1750                1755                1760

Tyr Gln Glu Lys Val Asp Val Val Leu Gly Pro Ile Gln Leu Gln Thr
```

Pro Pro Arg Arg Glu Glu Glu Pro Arg
1780                1785

<210> SEQ ID NO 4
<211> LENGTH: 5802
<212> TYPE: DNA
<213> ORGANISM: Homo sapiens

<400> SEQUENCE: 4

| | | | | | |
|---|---|---|---|---|---|
| tttatagcag | cagcagaaat | ataccaccct | agaggacaca | cctccttta | gctaggtacc | 60 |
| tataaatgtc | caggatttc | tattcaattg | agaagaaccc | agcaaatgg | ggatctccac | 120 |
| agtcatcctt | gaaatgtgtc | ttttatgggg | acaagttcta | tctacaggtg | ggtggatccc | 180 |
| aaggactaca | gactacgctt | cactgattcc | ctcggaggtg | cccttggatc | aaactgtagc | 240 |
| agaaggttct | ccatttccct | cggagtcgac | cctggagtca | actgcagcag | aaggttctcc | 300 |
| gatttccttg | gagtcaaccc | tggagtcaac | tgtagcagaa | ggttctctga | ttccctcaga | 360 |
| gtcaaccctg | gagtcaactg | tagcagaagg | atctgattct | ggtttggccc | tgaggctggt | 420 |
| gaatggagat | ggcaggtgtc | agggccgagt | ggagatccta | taccgaggct | cctggggcac | 480 |
| cgtgtgtgat | gacagctggg | acaccaatga | tgccaacgtg | gtctgtaggc | agctgggttg | 540 |
| tggctgggcc | atgtcagctc | aggaaatgc | ctggtttggc | cagggctcag | gacccattgc | 600 |
| cctggatgat | gtgcgctgct | caggacacga | atcctacctg | tggagctgcc | ccacaatgg | 660 |
| ctggctctcc | cataactgtg | gccatggtga | agatgctggt | gttatctgct | cagctgccca | 720 |
| gcctcagtca | acactcaggc | cagaaagttg | gcctgtcagg | atatcaccac | ctgtacccac | 780 |
| agaaggatct | gaatccagtt | tggccctgag | gctggtgaat | ggaggcgaca | ggtgtcgagg | 840 |
| ccgagtggag | gtcctatacc | gaggctcctg | gggcaccgtg | tgtgatgact | actgggacac | 900 |
| caatgatgcc | aatgtggtct | gcaggcagct | gggctgtggc | tgggccatgt | cagccccagg | 960 |
| aaatgcccag | tttggccagg | gctcaggacc | cattgtcctg | gatgatgtgc | gctgctcagg | 1020 |
| acacgagtcc | tacctgtgga | gctgccccca | caatggctgg | ctcacccaca | actgtggcca | 1080 |
| tagtgaagac | gctggtgtca | tctgctcagc | tccccagtcc | cggccgacac | ccagcccaga | 1140 |
| tacttggccg | acctcacatg | catcaacagc | aggacctgaa | tccagtttgg | ccctgaggct | 1200 |
| ggtgaatgga | ggtgacaggt | gtcagggccg | agtggaggtc | ctataccgag | ctcctggggg | 1260 |
| caccgtgtgt | gatgatagct | gggacaccag | tgacgccaat | gtggtctgcc | ggcagctggg | 1320 |
| ctgtggctgg | gccacgtcag | ccccaggaaa | tgcccggttt | ggccagggtt | caggacccat | 1380 |
| tgtcctggat | gacgtgcgct | gctcaggcta | tgagtcctac | ctgtggagct | gccccacaa | 1440 |
| tggctggctc | tcccataact | gtcagcacag | tgaagacgct | ggtgtcatct | gctcagctgc | 1500 |
| ccactcctgg | tcgacgccca | gtccagacac | attgccgacc | atcaccttgc | ctgcatcgac | 1560 |
| agtaggatct | gaatccagtt | tggccctgag | gctggtgaat | ggaggtgaca | ggtgtcaggg | 1620 |
| ccgagtggag | gtcctatacc | aaggctcctg | ggcaccgtg | tgcgatgaca | gctgggacac | 1680 |
| caatgatgcc | aatgtcgtct | gcaggcaacc | gggctgtggc | tgggccatgt | cagccccagg | 1740 |
| aaatgcccgg | tttggtcagg | gctcaggacc | cattgtcctg | gatgatgtgc | gctgctcagg | 1800 |
| acacgagtct | tacccgtgga | gctgccccca | caatggctgg | ctctcccaca | actgtggcca | 1860 |
| tagtgaagac | gctggtgtca | tctgctcagc | ttcccagtcc | cggccaacac | ctagtccaga | 1920 |
| cacttggcca | acctcacatg | catcaacagc | aggatctgaa | tccagtttgg | ccctgaggct | 1980 |

-continued

```
ggtgaatgga ggtgacaggt gtcagggccg agtggaggtc ctataccgag gctcctgggg      2040
caccgtgtgt gatgactact gggacaccaa tgatgccaat gtggtttgca ggcagctggg      2100
ctgtggctgg gccatgtcag ccccaggaaa tgcccggttt ggccagggtt caggacccat      2160
tgtcctggat gatgtgcgct gctcaggaca tgagtcctat ctgtggagct gccccacaa       2220 tggctggctc tcccacaact gtggccatca tgaagacgct ggtgtcatct gctcagcttc      2280
ccagtcccag ccgacaccca gcccagacac ttggccaacc tcacatgcat caacagcagg     2340
atctgaatcc agtttggccc tgaggctggt gaatggaggt gacaggtgtc agggccgagt      2400
ggaggtccta taccgaggct cctggggcac cgtgtgtgat gactactggg acaccaatga     2460
tgccaatgtg gtttgcaggc agctgggctg tggctgggcc acgtcagccc aggaaatgc       2520 ccggtttggc cagggttcag gacccattgt cctggatgat gtgcgctgct caggacatga     2580
gtcctatctg tggagctgcc ccacaatggc tggctctcc cacaactgtg gccatcatga       2640
agacgctggt gtcatctgct cagcttccca gtcccagccg acacccagcc cagacacttg     2700
gccaacctct cgtgcatcaa cagcaggatc tgaatccact ttggccctga ctggtgaa       2760 tggaggtgac aggtgtcgag gccgagtgga ggtcctatac caaggctcct ggggcaccgt      2820
gtgtgatgac tactgggaca ccaatgatgc caacgtggtc tgcaggcagc tgggctgtgg      2880
ctgggccatg tcagccccag gaaatgccca gtttggccag gctcaggac ccattgtcct       2940 ggatgatgtg cgctgctcag gacacgagtc ttacctgtgg agctgccccc acaatggctg     3000
gctctcccac aactgtggcc atcatgaaga tgctggtgtc atctgctcag ctgctcagtc      3060
ccagtcaacg cccaggccag atacttggct gaccaccaac ttaccggcat gacagtagg      3120 atctgaatcc agtttggctc tgaggctggt gaatggaggt gacaggtgtc gaggccgagt     3180
ggaggtcctg tatcgaggct cctggggaac cgtgtgtgat gacagctggg acaccaatga    3240
tgccaatgtg gtctgcaggc agctgggctg tggctgggcc atgtcggccc aggaaatgc      3300 ccggtttggc cagggctcag gacccattgt cctggatgat gtgcgctgct cagggaatga    3360
gtcctacctg tggagctgcc ccacaaagg ctggctcacc cacaactgtg gccatcacga      3420
agacgctggt gtcatctgct cagccaccca aataaattct actacgacag attggtggca     3480
tccaacaact acaaccactg caagaccctc ttcaaattgt ggtggcttct tattctatgc      3540
cagtgggaca ttctccagcc catcctaccc tgcatactac cccaacaatg ctaagtgtgt     3600
ttgggaaata gaagtgaatt ctggttatcg cataaacctg ggcttcagta atctgaaatt     3660
ggaggcacac cataactgca gttttgatta tgttgaaatc tttgatggat cattgaatag     3720
cagtctcctg ctggggaaaa tctgtaatga taccaggcaa atatttacat cttcttacaa     3780
ccgaatgacc attcactttc gaagtgacat cagtttccaa aacactggct ttttggcttg     3840
gtataactcc ttcccaagcg atgccacctt gaggttggtc aatttaaatt catcctatgg     3900
tctatgtgcc gggcgtgtag aaatttacca tggtggcacc tgggggacag tttgtgatga     3960
ctcctggacc attcaggaag ctgaggtggt ctgcagacag ctagggtgtg acgtgcagt       4020 ttcagcccCtt ggaaatgcat attttggctc tggctctggc cccatcaccc tggacgatgt     4080
agagtgctca gggacggaat ccactctctg gcagtgccgg aaccgaggct ggttctccca     4140
caactgtaat catcgtgaag atgctggtgt catctgctca ggaaaccatc tatcgacacc     4200
tgctcctttt ctcaacatca cccgtccaaa cacagattat tcctgcggag gcttcctatc     4260
ccaaccatca ggggactttt ccagcccatt ctatcccggg aactatccaa acaatgccaa     4320
gtgtgtgtgg gacattgagg tgcaaaacaa ctaccgtgtg actgtgatct tcagagatgt    4380
```

```
ccagcttgaa ggtggctgca actatgatta tattgaagtt ttcgatggcc cctaccgcag   4440 ttccctctc attgctcgag tttgtgatgg ggccagaggc tccttcactt cttcctccaa    4500
cttcatgtcc attcgcttca tcagtgacca cagcatcaca aggagagggt tccgggctga   4560
gtactactcc agtccctcca atgacagcac caacctgctc tgtctgccaa atcacatgca   4620
agccagtgtg agcaggagct atctccaatc cttgggcttt tctgccagtg accttgtcat   4680
ttccacctgg aatggatact acgagtgtcg gccccagata acgccgaacc tggtgatatt   4740
cacaattccc tactcaggct gcggcacctt caagcaggca gacaatgaca ccatcgacta   4800
ttccaacttc ctcacagcag ctgtctcagg tggcatcatc aagaggagga cagacctccg   4860
tattcacgtc agctgcagaa tgcttcagaa cacctgggtc gacaccatgt acattgctaa   4920
tgacaccatc cacgttgcta ataacaccat ccaggtcgag aagtccagt atggcaattt    4980 tgacgtgaac atttccttt atacttcctc atctttcttg tatcctgtga ccagccgccc    5040
ttactacgtg gacctgaacc aggacttgta cgttcaggct gaaatcctcc attctgatgc   5100
tgtactgacc ttgttttgtgg acacctgcgt ggcatcacca tactccaatg acttcacgtc   5160
tttgacttat gatctaatcc ggagtggatg cgtgagggat gacacctacg accctactc    5220 ctcgccgtct cttcgcattg cccgcttccg gttcagggcc ttccacttcc tgaaccgctt   5280
cccctccgtg tacctgcgtt gtaaaatggt ggtgtgcaga gcgtatgacc cctcttcccg   5340
ctgctaccga ggctgtgtgt tgaggtcgaa gagggatgtg ggctcctacc aggaaaaggt   5400
ggacgtcgtc ctgggtccca tccagctgca gaccccccca cgccgagaag aggagcctcg   5460
gtaggtggtc gctctcagac cccactgtcc accggggcgc agaccctga ctcggggact    5520 tgggatgttc ctcttggtgt catattccaa ctcagattga gccctacatt gtgctgcacc   5580
tggtcatacg gagttgaatc agacctggtt cccgcctccc caaggctca tggtccttgg    5640 aggacccgtt gcagggcgag gtcaagagag ttctgacctg gatggcccat agacctgacg   5700
tcccagaatc catgcttctc atctgcaaaa tgaaaatgtc aatacttact tcttagcact   5760
gttgagaggg ttacttacat aaaggaattt tggtgaaact gc                      5802
```

<210> SEQ ID NO 5
<211> LENGTH: 7379
<212> TYPE: DNA
<213> ORGANISM: Homo sapiens

<400> SEQUENCE: 5

```
agtattctta ccatcatctt tccctgctgt gctcccggca gacaattcta atctgtcatg     60
acactctgat gatcccagac ccagctgcat tatcattctc agtccaacac tccaggaacc    120
aagggatcac aatccccttc taagaggaat ccagcatgtg cctggtcttg ggcattccct    180
ggtaggtgag taaccctgtt ctctcgtcac ccagtgctta tcagttgctg atctggcagt    240
aggaggatga aacacagtga gcctattctg tgttcctatt ctactcaagg ggtgaagagg    300
cacctggaaa caacaggaag agttgtagga ttaaaaagga catccaagat tgaatgtaac    360
tttcatctgg atgaagccaa aggcagactt ccagccctaa attctgactg gtggctgaca    420
caggacatgg gttcatggta cccttctaga atgcagcata gactactgat gaacagtgca    480
tggcaaagaa gccaagtgtc atttcatggc ctcagcctct cagctgagaa gcagggcaca    540
gctcacccag gctaggaaaa cagaggcaag tcctggaaag ctgtctgctt ttaaccaaga    600
gttactggcc atcaagtgtc ttggttaaaa aataagtgtc aggcaacctt cttggtagat    660
```

-continued

```
agagtgtgtt gggggcgatt atcagagtct ggtaatgact tctgagggtc ccaaagagtg      720
aagtgatatt tacatagcaa atccaaggag ggggattgtg tgcaatatag gtggaggtgg      780
gggcaggttt tgtgggtttg ccaagctcca agggtcatac aatgtgcatg tcaaggacaa      840
gaaatcaaag ccatgtgaaa tggttggagg tggttcagtt tgaggtcatg tgtttctcag      900
ctcctgttgt ggaattagtg tgagacccag aagactgtgg ccaaagctat tatggaccca      960
tggtctctgt ggactcatcc ctcatgcctt ctgctctctg atcacatcca cactcatgtc     1020
atcctcgttc ttccaaggtg aggttactag cactgcacag gggctgatga gagcatgtcc     1080
tgccaggaaa aaccatccca agagatgct ttcccccttg gcactgtgtc ctgtatttgc      1140
tcagcagccc acatcctgtt ctgccccaaa ccttggggca gacttccac aggtgaattt      1200 gaactcccca agattaaaat caagcctgta ttcaggaaac acttgggagt cctcgaggtt     1260
caccgagagg gaagttggaa atttttcact tatgtcagtg cgtttgcagt tgggcaacag     1320
ccagattgtt catatggcaa tcaatcaaac acacctaagt ttttccaca tattagccat      1380 cgactgttag caaaagccct cacttccttt atattgattt atagcagcag cagaaatata     1440
ccaccctaga ggacacacct ccttttagct aggtaccttat aaatgtccag gattttctat    1500
tcaattgaga agaacccagc aaaatgggga tctccacagt catccttgaa atgtgtcttt     1560
tatggggaca agttctatct acaggtatta cgtttaatta ttatattcat taatttctct     1620
cctgcagacc caatcatggc aaattatatc tactactttc cattacaagg gaagttttat     1680
atcaaagagt gggtagcact ttgctgataa ttgtaattgt ttgcaggtat tcaggaggaa     1740
tggctctttt ttgttttatt tctggctgag aaatataaat ggttgtagtt agaaaaagcc     1800
agtcattaag tcaatgtttt cagtaagtca ttcaactaaa ggaatgattg atttgtctta     1860
gaaaaatccc tgaagtttag gaaggtgga tgtgtattat taagaggccc ttaaactttg      1920
cagcaattgg ttaaacacac agtttgtgtg ctatgaaaac ggacagaaag gattcccact     1980
gcaaatgccc tttatgtggc ttcttctac aggtgtgtct ggcttgatgg ctaatatttg      2040
ccgagcaaaa tcaggtcaag taattgagcg cagacaagat cattaagatt ccaagtttgt     2100
cttggaattc caagtttgtc tgtcatgcac agctttaaac aaacacttga agcccagtca     2160
ctcaagcata gctgtatgtt cttagagagt cagatgataa acgtgagaga gccgtcggta     2220
gcgcactctg attgctgcat ctcaatggca ttttgcagag atactagagg aacaagtgat     2280
tctcagtttg cctattctgt ctctctcttc tctctctct gcctctctct ctctctctct      2340
ctctctatct ttctctctta tctattgtgt agttattatc atcttttctc tcccctctct     2400
ctccctctgt ttctgtctgt ctgtgtttct ctctctctct gtatctttct cttttttccca    2460 tcttttgggc agatatcacc ttttcttcct cctcctccct ctgtttctgt ctctgccttt     2520 ctctcccctgc cccctcact gtatcttcct gtctttctca tctatcaggc agttattacc     2580
tttcctccct ccctcctccc ccttctctgt ttctctctcc atctctcttt ctctttattg     2640
ggcagctatt atcaccttc tctctgtctc tgtctctgtc tctctttctc ttcaactatt      2700
gggcaactat tatcacctct cctctctctc tctatctgtt tctcttcatc tgtcaggcag     2760
ctattatcac cttccctccc cctctctttt tctctctcac tctttctcat catctattgg     2820
gcagctctta tcacttttcc tccctatttc tctctctctc tctcccttg tttctatctt      2880 ctttctacct tccttccatc ccttttttctt tctctccctc tctttattca tttctttctt    2940
ccttcttctc tttttatcttt cctactgcct tttttttctt ttatgtcacc ttttgctaga    3000
tttatgaatt tcaggataca gggtaaaaat cacctaattt tcaggtaact tccggaactc     3060
```

```
tcactctccc cctaggctca gtgggggaag atttgaagat taaggttcat ctggttggtt     3120
gctttcatga aagcagcacc tcccaaccca gccctcacac ccgggtggta gggagcaggc     3180 ccacccctg tgatgagcgt gtggagggcc tgggggccac taggcccagg acctcagggg     3240
agtggagact gggcatcctc atcctgcctc catcagaagc atctgaaact gggaggctgc    3300
gtcctcagcc ccagctcttg tcagtaccga gttcaccctc cagattgtct ctgaaccatg    3360
acatggaatt cacatcagcc actgtagaca gggagtgaat tgccttgtct ttatctacaa    3420
agaaacaaca ggcagcagtg ctcttggatt gaggacattt gtagtttgcc catgatgttt    3480
tgtgcatgca tatggacaga catgcacata tgtgcatgca tgcctgtgtt tgccattcag    3540
aggtgggaat tcatgctctc tgaagtggac ccgtattctc ttatttaaat cttctaacat    3600
tcctgaagtt aggaacaatt atttccacat tcagatgggg aaactgagg ctcagaaagg    3660 ttattggctt gtccaaagac agcactggtg agtggctggg ttagggcttg aatctggatc    3720
aaattcacta gcattcagat gacagctctg gcccactggc ccttgctgct ccttgcaggg    3780 aactgaggt atgaactgaa ctgtggcatc taactcagtg cttggagcct gaccacagag    3840
ctttgtgctg gaagtaccga ggtggcaggc acctgtcagc tctggtcttc atgcaaactc    3900
ttgagaaaaa ctcagtatgc ccaggtttgt gctgggcagg aaaggctgtg gtacccactg    3960
ctagccccag caatgcccct cctctgccac ttgcctgctg tggatcctct gtgaccctca    4020
gtttactcat ttataaatgg aggttatgtt ccaacccatg caatatctgg cacatagaca    4080
gagcctcaga accatttagt gttactactc tagacatttt cctcatgttt tatccaaaag    4140
cagcttccta aaagtaatgt gagctcttgg attggatcct gcaacagaaa atgaaaaact    4200
ggtgaaatcc agataaagcc tggagtaaac ttagtaggaa ggtaccagtg tttgttagca    4260
tgagaatcac ttgaactcag gaggcagagg ttgccgtgag ccgagattgt gccactgcac    4320
tccagcctgg gtgacagagt gagactctgt ctcaaaaaaa aaaaaaaaaa ttaataaatc    4380
attttccaga agtgattctt ctcccttcag gcaatttacc accattccca caatggcagc    4440
tggagtaacc tacagctatg tggttgattc ttggaagact acagattggt ctcagtatgt    4500
gcagaagggt ctattcaaaa tgtgtggaca cagcagaacc aggaacaact tcaatgtggt    4560
gttccatgct gtggatgagc cttgtcaagg ctctggctgg atgagttcga ctgccatggg    4620
attaggcagg atacctggga cctggcagtg ggaattgcat ggtgtcaggt agactgtgtt    4680
taaatggccg agttttgaat ggaaggctct cttaggcaca tctatcagct cgttcttgag    4740
tgtgggagca gggatggcac gtcagaaaag aggtggggat gttctggtac agagttccct    4800
agtttgctat ctctgttgaa agaatgttgt ggtttctatt ccgagtttct tcttcatttt    4860
aagggatgca tagccacatg gtttcagtgg cccccttcct aagccatcaa tatgaagcag    4920
ggcagctggg ggagcccatc gtggagctca tattcaggct gttgaggcag gtgaagatgt    4980
tctctgacat atggcaagtc ctgtcactgg cctgttggtt ccattagaga aattcaaatc    5040
tctgaactgt gactgtcact gctctcagga cccacattta caaagaatct gaagagccgg    5100
gcgtggtggc acatgcctgt agttccagct actctagggc tggaggcagg aggcttgctt    5160
gaacccagga atttgaatct agcctgggca atagagcaag actctatctc taaaagtaaa    5220
ataataatct gataattttg tcaaatgcct taatcctcct tttaccagga agtaaaaaga    5280 aaggaataa tgaaagtatg ctggaattgt taataagaat ttaaacatag cagaccttt     5340 tatatcacat acatttttggt atataaacat cataaaagac aaaagaatac catcacaggt    5400
```

-continued

```
attttttttt ttttagcaaa ataagatggt tgaagttctt gttgcaaaat atcatgtgat      5460
gaaatcccta tcgaagtgtg taagagtacc gtattttatt tttgtcctta gaattgtatc      5520
attgaccctg gattcttgaa tttgagaaat tcatctagga tatcaccatc tgaagactca      5580
tagtctgaga tttctgttgt acaatcaatt ctaccattat tagtatctgg agtgctatat      5640
cttgtctcta tattcctctt ctggttcatc taattattgc aaaaacatct tctcttgtca      5700
gttttcttct ctttgccatc acaagtagaa aatgaaaaaa tttgaattct taactgcatt      5760
caatgaaagc taaaaacaga ctatgaagaa agtgtctcca gtcttaaaaa aaaatcttct      5820
tgaaagataa tacaatactt tgggcatgga agaattatga cttatttcac tagttcatct      5880
tccttctagg caacttcacc attctaccat tttcttacta tttaataatt gatgaataat      5940
gatgcaatac tttcttggat gatgaaatag tgaaatgctt caagacatag gaaaaataaa      6000
atcagaagcc aataatgaat cttggattta taaaaggatc taatggatcc atatggtgat      6060
tacaagatag gatgagtttt atcctttttt ttaaatgaat aaatactctc tctgatcttt      6120
gaaagacctc taaatatat aaagttgtg aaatatcaac actcacgagt atagttagaa      6180
ctgctcaaaa agaaactcaa aagctacagt tgagtccgat ggaccttgtc tggcctcact      6240
gaatataaag atccagggat ctctagattt ccatttgctt caagatggaa taaaatattt      6300
tcaggttatg agtcagaagg aacagaatat ctgacattaa catattttct tctttagggg      6360
tcatctgagt ggctgttgca gctatactca aatttcagac tggacaacca gcttaagctg      6420
tcttctcttg tccagccctt ctttccaagc atagattaca tcctgtcacc ataagctgta      6480
gtgttagggg cctagtaaag agacatatgc ttcattacat ctaaaatgat tgagctcctc      6540
atatccaatc cacttgcttt aatccgctat tgcagaattc atttagcaag aacgtcgggg      6600
acacacaaac ccaagattga gccacagcgc cctctggtgt gattgtacgg tgaagcgaaa      6660
gccaatttct gtgacttgta ggaaatcatt tctaaacagt gttctaaga cgaatttgtg      6720 ttcttttccag gtgggtggat cccaaggact acagactacg gtaagacctt tcttcactc      6780 ctcttccctg gtggggttgg ccagttctcc tctgctgctg ttggctagtt gaggctgagc      6840
acagctgagg tcacagagca aacgcctgcc ttgtcgaacg caggaatgcc ggggggacag      6900
gagacgtggg tgccaagacc tggggcatgt ctcaagtgcc cactcggcca atcccagctg      6960
tcattctcct tcctcttgct ctctgactct cagtcattta tcagatgagg ttagtttcag      7020
tttggtgtga ggagagatag ttgaaaataa aggttagtac cttttctttt ttttcttttt      7080
cttttttctt ttttttttga gacggagtct tgctcaccct gtcaccagac tggagtgcag      7140
tggtgcaatc tcagctcact gcaacctccg cctcctgggt tcaagcaatt ctcctgtctc      7200
agcctccaga gtagctggga ctacaggtgc gcgccaccac gcccagctaa ttttgtagt      7260 tttagtagag atgggttttc accatgttgg ccaggatggt cttgatctct tgacctcgtg      7320
atccacccac ctcggcctcc caaagtgctg ggattacagg catgagccac tgcgcccgg      7379
```

<210> SEQ ID NO 6
<211> LENGTH: 29598
<212> TYPE: DNA
<213> ORGANISM: Homo sapiens

<400> SEQUENCE: 6

```
gtacacgtgt atgtgctctg cattttactt gctttgctgt aagtgatggc tgaatgacgt        60
ttggagggta agtagtattg cccctttca tagacaatga aggtcaagcg gttatcttcc       120
tgtccttctg aagttggatg tggtggaggt aggcttcagt ctcagcccct cagagcctgc       180
```

```
tgatgcaatc acttcagcag catcacgacc tggcctggga taccaaatat acatcttcct    240
aagtggcagt ttctccctttt ttaaaatttg aggagggtgg gagaactctt gggacttaag    300
acataaatgt atatcaacat cagattgagg agggaaccca ggcattctat ttactggaaa    360
ttaagtgaca aataaaagat acttaacatg ctcaatggaa aagagaactt ccctggacc    420 taacccagca agtcccagtg ctgatttcct ttgttcacat agtgccagga tgtgtgcaga    480
caccaagagg ttttttttaat tcacaaagaa acctacaagg acactgtccc atggcgtgat    540
ccccaaagag gagtttctgg ttaaactgtc tacttcaaga gcaactctgt catttggagt    600
gtgggctgga ctgagcccat gccaccatgc ctgggtgtg cccttggtaa tccaaccacc    660
aagtgggact gggctcccca aggggcatc gtcctccatg cagccacttt gtgagtggtt    720
tagttttgca ttctggaaag gttggttttc tttcgaaacc accttttttc tggttgaacc    780
accttctcag gtatatttca gtgatggtgg atatttgtca tttgagggtg tgtttgagcc    840
atagaaaccg ccagatgtct tttgacattc aatcttgtga ctagcatggg gttgtgaatg    900
gactgggtga cttttttgaat agaggctgtg gcagcagagg atgggggt agggtaataa    960 gagtaaagga tgctcatgtg gcatcctagc ccagtctggg gccagtacaa tgacaaagcg   1020
attggcacat ggttggcttt tagcaatgga tggtgccgtt aggacctgtg cttccagccc   1080
ttgcttcaga gctgagcaag ccctggacca accctcccca agcgagggct acgatcaatg   1140
agctcttcct ttctccaccc tgcaggttct ctgattccct cagagtcaac cctggagtca   1200
actgtagcag aaggtaacgt ctactatggg ggatccctgt agactcatta ccccctgca   1260 cccctaggtt aatctctgat tcagatgagg tgcagagggc atagaaagta gggtgcttag   1320
ctcccacgag gggcccttcc acaaaaggcc tcaggtctga acaggtatat cttgcatcga   1380
tcatgtctga gactgaggag gaatcaactt gaagacgcgt ctccaaggag ttctcagtgg   1440
agccttttat tctgtctcta gagattctgt tatctttgct tgttgctcac tcctgtgttc   1500
ctcacccagc tgtgctcatc cgtggccagc ctagggttct ggatctctgg ctacagggcc   1560
ttgagggtca ggtgcctacc tgctaacgta gccaaattgc taggacagca tccttgccct   1620
tgccctttct ttaagcctat attatgccac ccttgtttct tcttaacaga gagaaatcac   1680
aatccttcag ctcatgggca tcagagctca tgtacttccc ccttgggtat ctccagtgag   1740
aaatctggga gacatagtca atacatcctg ggattctggc agcctgggct ttgggaaggg   1800
aagtcacttc ccatttccca tgggaaatct tggccctagg agaagctcaa ggacaacatt   1860
ctcaccaagg cctctgcgct gcccaggtt ggcatgcagt tgggaatgct gatggtacat   1920
gcatcgggcc ctcctgttcc tcaggtcgtc ttctttcttc tcccttctcc ctctggccca   1980
tggggtgagg tctgacttaa cctcttcctc tttcctatga tgaaggacac agaagacact   2040
tgaagtgagg gtgagactgg ctttattctg acttagccat gtcccttcgc aagattccca   2100
cattttctta tttgcagcag ctataagagg agaatctgtt ccttcctctt gagtggtttc   2160
ccctgaggtc cctgttacat gttaaggacc acaccttggt gggacaagcc ctttggtata   2220
actggtccag ccagggatgg gagtgagggg gcagaggtat ttggctgatc tgcctgtcac   2280
acaggactgc agataggact tacctggagt tgctcttatc aggaactcta gtgtcagctg   2340
ggagtcacat ttcttctaga tctggagacc tcacgtagca gcccagtgga gagctcagac   2400
agaagctgag tgctgtggct gcagtgggtt aagggtaact ctcagatcac ttcctctcca   2460
agccccagca ctcagtcagc tcctgtaggt gccctggaca aattccaggg ctctggagca   2520
```

```
attcaaaaac ggagattcca agccagtatc ttacttaaag gggaatatta gaagcatttc   2580
tgctaatgtg aaaaacaagg caagtatgcc ctccatctcc actgctgttc aatgttgtac   2640
tggaggtagt agccaatgca atgagagaag agaaatcaat tagaggccta agcatgggaa   2700
aagttatttt tgcatccctc ttctggagtt ctgtataggt tacatgtagg cacatcggaa   2760
tcagagtgag tatgttggta cagaaatatt tcctccccaa gcagccctttt agaatcaaag  2820 aactcaatgc tagacaggtt tcttgacttt cccaaattta cacagcaaga caatatccag   2880
atcaggagtg atggctcctc agcagatcct agtttacttt cagcccatga gtgtcttcag   2940
aggagaccta actttatatt ttctggtttt ttttgggggg gtgtggtggg gtttgttttt   3000
catcttctac aattggcaaa agcagagact accactacaa atactgagtc tactgttgtg   3060
acaggtaatg agtaactttg aatccctttc tgtaggtcat gttgccaact atatccatgg   3120
gctttactgt tactcaggaa aaattttagg gaatgggatg ggagggaatg ttgtgagtac   3180
acagtgacct tctggatccc agaggtcagc tagagtgaag cttccttcat tgcccatgtt   3240
cctggaggta gggagaaatc agtcagaata tggtgtctcc aagagcctgt gtgctttgga   3300
agcagagacc agtgggatca gtctccagtc cagagtgaca gcccagctcc cccatctcca   3360
cagctctgtg ctgaccctaa caatcctggc cctgaggaag gctataaggc caggaatatc   3420
acgtgacaaa tgtgctccaa accaaccta gagctgcaga tacacatcag agctcctccc   3480
gggacatctt gatgttatcg tgctgctctt cagtgtgggg tgttgtgtgt ccctgtctg   3540 agggaatcag gcagagccca tggtctgctt agagaagggt catgtgtatc tctaggtccc   3600
ctccaggatg cagatcagga ggagcctttt attctgctcc agctgaagct ctaaggcttg   3660
ggtttgggcc aagcagtcac tgtcctcttc cccatgaaga actctaacct taaggcctgt   3720
taaagcccag cccaattaga gattctctca agatatctg cctatgggga agaccctgaa   3780
tgccctgcag gccctgagac cttgtgcctc agtaggaatg tgcaagagaa attctgtgcc   3840
ttcctctagg atctgattct ggtttggccc tgaggctggt gaatggagat ggcaggtgtc   3900
agggccgagt ggagatccta taccgaggct cctggggcac cgtgtgtgat gacagctggg   3960
acaccaatga tgccaacgtg gtctgtaggc agctgggttg tggctgggcc atgtcagctc   4020
caggaaatgc ctggtttggc cagggctcag gacccattgc cctggatgat gtgcgctgct   4080
caggacacga atcctacctg tggagctgcc cccacaatgg ctggctctcc cataactgtg   4140
gccatggtga agatgctggt gttatctgct caggtaggca tccagatctc tggagggttg   4200
ggtgtggtgg ctcatgcctt taatccccac actttgggag gatgaggtag gcagattgct   4260
tgagctcagc cgttcaagac cagctctagg caagatggca aaccccatct ctattaaaaa   4320
aagaaaatca cttgggccca ttctggggac agactgtatt cagagaatat agtaacaggt   4380
ttctcactcc agggccccg cccaagtctt tcctggttat ctggtggctc tggagtttag   4440
ttggggcagt tggcctgtgg gtacaatgcc acggtcagca caaatcccca agctgcgagc   4500
agtgccgcaa cattggtttg gaggtgactg aggcaccagt gttcagacac aggtccagc   4560 atgctgacat cagaaatgat gagctttta ttctgctcca ggaacatccg cataactcat   4620 accccattt tccccgaggc tccttctcag ggacagcacg ttttgggat ctggttggtg   4680 aagccttccc tcccccttgaa cactgtatta ccttgagtgt tgtcagccgc tgacccagag   4740
ggaaggatgc aattgtaaat agttcactta tgattgctgt gaagagaggc agggaagtgg   4800
ggtaagggtg ggaggatggc agtgagtcgc aaatggtggg ctcacgagtg agctcagcat   4860
agggagcagg gggacctcct agagtatcac caggaatcca cgtcaaacct cagactcatc   4920
```

```
gcagctcaag cgtggagagt tagggtcttc atctactcat tgcttagggt ggctgtttgc    4980
tgctccctgg gtgttgatac cgaggttgtt gtggccggtc ccaggcaccg aagtgacctt    5040
catatccctg gagagtgagc cacaggcaca gagaaggcaa tgccagggc tgtggggtcc     5100
ctgagggacc gagggcttca cggtgggcac tggcagggcc cacttggtgg gcgtgtgatg    5160
ggcatcagct caggtgtag ataccccaag tcacttcagc cttaactcta cttggagtca    5220
ctgagtgttt ggtgtctaat gttgctattt ttttctcaca gctgcccagc ctcagtcaac    5280
actcaggcca ggtgagtccc cagaatcctt cctcgggata ccccttctct ttctgctcag    5340
ttaccccttc cctactccac agagccctcc tgcttctctg cagatactct ggggcatatt    5400
atttcacccc caactctgta actgagaccc tagcatgggg cttcttaacc acacatggga    5460
tttagcttct gccttctctt cagtccatct cagctttcat cacacagttc catgctgtcc    5520
caatgaacaa ctcttagaag ttcagaaaga agcctgctgt taatgagct ttggcctctt     5580
tatattcagg gctgacacaa ccttttctggg aattgagggt gagactctct aatgttctgt   5640
tgaaggcaag gtcagtacag gcttgatacc cccatctctc actacttgaa aaacccccag    5700
attctgcagg gccacgtctg cattcagaag aggcagaggc catgctgagg ggagagagag    5760
gctaagaaat gtttctggtg ccttcactta ccaggaaacc tgatttcccc cagggcggac    5820
ccctagtatc ccgaacattt tagctgcaag tgtcaagtct tggcagtggt gtcagatgag    5880
ccagtcagtc cacgcgtcag tggatggtgg gggatggggg tggtgaaggt ttcctaactg    5940
cgaataggtc atccctctct cagagagagg tggaagggcc tgcatggtgt cctttgtccc    6000
tgaatgagtt ccctgggcag gagacctggg cagacacatg gggagcaagt ggccagacct    6060
tcgagtggaa ttgttttcac agtgcttgcc tggtccagag aaccgcttgt tttttacctt    6120
tttcccttca gtccaattg tatcctttct ctttgttgct gtttacagaa agttggcctg     6180
tcaggatatc accacctgta cccacagaag gtaaagaatc ctctcaacac tccctggggc    6240
tcactttcta cctctggata cactttggat ttcatagttc acttatgatt gccataaaga    6300
gaggtgggga agtgggctaa gcgtgggagg gtggcagcag gtgataaaca gttggctcaa    6360
gagtcagctc ggcactggga acaagagcag gacctcccag aagatcatta agaatcatta    6420
ggctcatgat aggatgaggc tcaaggtggg ccccttgctt tttcatgttt ctgtgggttg    6480
ggtaggagg aagctggagt ctctgaaaac ccagaattag atgtgatatt ggagggtgga     6540
gggtgctggt gacctgtctc ctgtgggatc ctgttccaag tggtcagaaa agatccttat    6600
ctatgggctc agaacaagcc ctgggggtct ccctaatcct atgggaccct catccctgcc    6660
atctctggta ctctgccagt cagatcccag ataggaccat gctcctgaat aagggagggg    6720
tctgggcctg ccatctggag ctgagcagct ccatcctctg tgtacccaac tggggagtgg    6780
ggcatccatt cccatcacat ccactgggt cacaggtgct tccccaaaag ttgagcatcc     6840
atagacctgg gcagagtagg ttatcagtgc tactttcacg gtgatgaagc ctagtctgtg    6900
gtcatatgca aggtgactg cctgcctagg tgacttagtt cattaggaag taccctgagt     6960
gtggaactta ccttagattc ttgacctcat gatagggatg gatgaagggt tcttgtgttc    7020
ccctgtagga tctgaatcca gtttggccct gaggctggtg aatggaggcg acaggtgtcg    7080
aggccgagtg gaggtcctat accgaggctc ctggggcacc gtgtgtgatg actactggga    7140
caccaatgat gccaatgtgg tctgcaggca gctgggctgt ggctgggcca tgtcagcccc    7200
aggaaatgcc cagtttggcc agggctcagg acccattgtc ctggatgatg tgcgctgctc    7260
```

| | | | | |
|---|---|---|---|---|
| aggacacgag | tcctacctgt | ggagctgccc | ccacaatggc | tggctcaccc | acaactgtgg | 7320 |
| ccatagtgaa | gacgctggtg | tcatctgctc | aggtgggcct | tcaagaactt | gggctcactc | 7380 |
| tcttggggtg | gagtttgctc | caaaagaaac | tcctaattac | attctgatct | cctcactcaa | 7440 |
| agcttctatg | ttttctatgt | ttctgaagac | ttgtcagctc | tctgctaaga | atccatatgt | 7500 |
| actcactgcc | tagtgttcct | gtggtcactt | aggacagggg | atcaaactaa | aacaacccag | 7560 |
| agtttttccc | cttcctgagg | caaggcaagg | aagaggcaga | agagaaaagt | gccggctccc | 7620 |
| cagggctcca | tttctcccct | gctgagtagc | acggtgtgag | ggtataatgg | atgcagcaca | 7680 |
| gacagcaagg | caggggaggg | atcccctcac | tgcgaggaac | tctgaactaa | agatgcttgg | 7740 |
| ctaaaagtgg | gttctcagct | gagacccagt | gaggaggtct | ggaaatagag | gctcaagggt | 7800 |
| taggagtgca | aatgggtgtc | tgtttgtatc | aggcctgggt | tgcgtggggt | tggagttctt | 7860 |
| gacctcagct | cttctcagaa | cgctgctgag | cattgcctgt | gttctaggtc | tggtgagggg | 7920 |
| agggcagtcc | ccatgaggcc | agccagacat | ggccttgtca | ttgcctgtga | ttggggcttg | 7980 |
| aagatcgcac | aagggatttt | ggctggagtg | gcttcctcag | ccttgctgac | tcaggaacac | 8040 |
| ctaagatgtg | caagggagtg | ggttggttta | ggtcaaccgg | gttaccctgg | gcagacacaa | 8100 |
| tttgatcacc | tcagagctgg | caatagtgga | caggatctgc | ctcgacccct | tacacggtgc | 8160 |
| atctctgtgg | ggatgtgcat | ggcaatgtcc | ctccctgtgt | gataggaact | aggatggact | 8220 |
| gagtgtcaga | ctcgctcatt | tctttccctc | ctcgttccag | ttttgccgac | ttctgtgtaa | 8280 |
| tgttcctgat | ctgaccttct | cttctctttc | tcacagctcc | ccagtcccgg | ccgacaccca | 8340 |
| gcccaggtag | gtccccagtg | tccttcctca | aaatgtccct | tctctttctg | cccaatcacc | 8400 |
| ccttccacac | tccacagagc | tctcctgttt | ctctgtgtgg | atactgtggg | gcatattatt | 8460 |
| tccaccccca | acaccggctg | tgtaactgag | atcccagcac | agcgcttttt | aaacacacac | 8520 |
| aggattgagg | aggcctctgt | cttcttttca | acccctctca | gctttcatga | aacagtttca | 8580 |
| tactgtccca | gtggacaacc | cttacaggtt | caggaagtgg | cccatgtttt | aatgagcttt | 8640 |
| ggtccttttta | tattccggac | tcacatatag | tttctgaaaa | ttgagggtgt | caccctctga | 8700 |
| cccgttcaag | gcatcgtcag | ggcaggctcg | ataccccat | ccatcactgc | tggaaacatt | 8760 |
| ccagagattat | gattccgaga | tttctatcca | gaagaggcag | agtttgtgct | cgggcaggga | 8820 |
| gagggataat | aaaggtttgt | gatgtctctg | cttaaccaga | aacctgattc | ctgattgtcc | 8880 |
| cctgggcagc | ccctggttcc | cctaacattt | tacctggcag | tgtccgagct | tcagcaatgg | 8940 |
| cgtctgatgt | cctagtcagt | ccatgcatca | gcagatgtgg | gatggcatgg | tgggggcatc | 9000 |
| ctctaacaga | tagaaagata | ccccaggatt | acagaaatgg | agggctcagt | ctggtctcca | 9060 |
| gcaggacctt | tgtccctgga | tgagttcaca | gcacaggaga | cctgggaaga | cacatgggaa | 9120 |
| acaaatggca | ggaacaagaa | gtggaattgt | tgtcacgttg | attcctcctc | ccagagatcc | 9180 |
| ttttgttctg | tgccttttcc | cttcaagtct | aattctgtct | tttccttttg | ttgcaattta | 9240 |
| cagatacttg | gccgacctca | catgcatcaa | cagcaggtaa | ataaccctct | cacccctccc | 9300 |
| taggactcac | tatctctgga | catattttgt | gtttgaaact | gataggatga | ggctcaatgt | 9360 |
| gggcttctct | gttttcatgt | ccctgtgggt | tgcgtgggag | gaaggtggaa | tctctgagga | 9420 |
| gccagtcctg | ggtctgatgt | ttgaggacgg | agggtgttgg | tgacctgtct | cccatggaat | 9480 |
| cctgttccaa | gtggtcagga | aagatcctca | tccaggtgct | caggacgagc | actggagggc | 9540 |
| tccttaatgc | tgctgggacc | tcattcctgg | ccctcaggcc | atgggatcca | gacctctgaa | 9600 |
| gagcgggtga | aagtgccggt | ccctgcacct | gtgtggccaa | ggccttgcca | tcactggcaa | 9660 |

```
tttgccagaa ggcagagagg cccatgcagg tgccaataag ctcctgaata tggaggggt    9720 ctaggcctgt catttgtagc tgtgtagctc catcctgtgt tcacccagag tggggagtgg    9780
ggtgtccatt cctgtcctct cctctggggt catacatgct tacccatagc ttgagctttt    9840
atagacttga gtagaatagg gcatcacttt ttccactatg accaagctta acctctgggt    9900
gcagccatct gccattgtga ctgcgtgccc tggtgacttt gcatttgta ttcaaacttg    9960 actacttttc ccattgccct gagtgttgtc catgccttt ccttcacctc agaatggaga    10020
tggatgaagg attcttgtgt tccctgtag gacctgaatc cagtttggcc ctgaggctgg    10080
tgaatggagg tgacaggtgt cagggccgag tggaggtcct ataccgaggc tcctggggca    10140
ccgtgtgtga tgatagctgg gacaccagtg acgccaatgt ggtctgccgg cagctgggct    10200
gtggctgggc cacgtcagcc ccaggaaatg cccggtttgg ccagggttca ggacccattg    10260
tcctggatga cgtgcgctgc tcaggctatg agtcctacct gtggagctgc ccccacaatg    10320
gctggctctc ccataactgt cagcacagtg aagacgctgg tgtcatctgc tcaggtgggc    10380
ctccaagacc ttgggctccc tctcttgggg tagattttgc tcaggaagcg aggtctcatt    10440
atgttctgat ctcctcactc agagcttttt cagcctttcc tatatatctg atatctcctt    10500
agctctctcc taggaaactg catgagtctt cattgccagg ttttgaggag gtcaggtagg    10560
acaacgggcc aaagtgaaat aagggtcacg cctttgttca cctaccgagg cagcgcaagc    10620
agagggagaa gaggaaagtg ccaggtcttt gccttttagt gtggctggaa aggaatagct    10680
ggggctggtt tgttcatgag gaaagaggct gatttgggtc ttggctttgc aggctgcata    10740
ggaccatggt gcaggcgtct gctcagcttc tgatgagggc ctcgggctgc ttgtactcct    10800
agcagaaagg gatggggagg tggcctgggc agaggtcaca aggtgaggga ggaaggaaga    10860
gagagcaaga gggagggctc agactcttca accaccagct cttgctagga actaagagaa    10920
gaactcaccc ctgaccaggg agggcactaa gttattcatg cagtgttggt ctccatgacc    10980
cagacctggt gcatcaggcc tcacctctaa acttggggat tcagttgcaa tataacactt    11040
ggatgtgaca agcctctaaa gtatagcacc ctggctctcc agggttccat cttccccta    11100 ctgaaagatt ttgcaaaggg ttacatggat gaagcacata tagaggatgg gggagggact    11160
gtctccctgg gaggagccca gaaccacagg ctcctgctag gaagcgcggt cttctgctga    11220
ggcccaataa ggtgatgtct taatagagac acaaggctag gagtgcggat gtgtgtctgt    11280
ccctctctgg cctgagattt ggggctgtg agtccttgac cacaactccc tccagagcac    11340
tgcagtgtct tgcctgtgca ccggtctggt gtggagtgtg cagtccccat gaggtctgct    11400
aggcaaagca ttgttatgaa cgcctgtggg ctggactgga acatcagagg caggactttg    11460
gctggagtgg cctcctcaca tttgctaact cagggactgc taagacatgc aagggagagg    11520
gtaggttttg tgtcaacctg attactatgg gcagacacaa ggtaatcac cttggagttg    11580 gcaatagtgg acaggatctg cccagacacc ctccaaggag catctctgtg gggacatgca    11640
tggcaatgcc ctccctctgt gatgggacc tagggtggac tgaaggcatg atctgtttag    11700
ttccttccac ctttgttccg attttgccag cttctgtata gtgcatctga tctgacctcc    11760
tctttctcac agctgcccac tcctggtcga cgcccagtcc aggtgagtcc ccagtgtcct    11820
tccttgggat gtcccttctc tttctgtata attatccctt tctgcactcc acagagccct    11880
cgttcttctc tgagtgaata ctacatggca tacaattttc ccctgctctg taactgagac    11940
cctggaatgg cgcttctgaa ccagacatag ggttcaagag gcttctgtct tctgttccat    12000
```

```
ttatctcagc tttcatgaag cagtttcata ctgtcccagt ggccaaccct tagaggttta    12060
ggaagtggcc tcatatttaa atagctttga ccctttctta ttcagagctg atatgacctt    12120
cctgagaatt gagagtgatt gccaaagtct cctcggaagc caatgtcagc taaagcctta    12180
aacatggctg ccgccatggg caagcaatgt cagtgcaggc ctgacacctc ccttcctcac    12240
tccttccaac acccagattc tgcagcgcta catgtgcatc cagaagaggc ataggccatg    12300
ctcgggcagg gagagggata ataaatattt ctggtgcctc cacttactgg gaaacttgat    12360
acccctttgg tcagctcctt ggtttcccta acgttttagc tcgagctagt agagtgtcag    12420
caatggtgtt agatgtaccc gtcagtgcat gtgtcagtgc atggaacagg ctaacccttt    12480
gtgactgaga agaggacatc ccacacttca gaggcaggag ggatcgaact ggtctccagc    12540
aaggcttatg tcccttgctg agcttgctga gctgcagact tgggcagaca catggggagc    12600
aaagtggcag gaatcagaag tggggtagtt ttcatgatgc tcgccttctc cggagacttt    12660
tccttttgga gattttcacc atcaacttta attctagcct ttgtctctgt tgcaattaca    12720
gacacgttgc cgaccatcac cttacctgca tcgacagtag gtaaataatc ctctcgcccc    12780
tccctagggc tcactctcta cctctggaca aatgtttttt tctgaaatga taggatgagg    12840
gtcaaggtgg gcccctctgt ttttcatgtc cctgtgggtt gcatgggagg aaggtagagt    12900
ctctggggac ccagctgtgg gtctgatgtt ggaggctgga gggtgctggt gacttttctc    12960
ccgtggaatc ctgttccaag tggtcaggaa acatcctcat ccaggtgcca aggaaaagcc    13020
ctggaagctt cccctaatcct actaagacct cattcctgtc cctcagccca tgggctgcag    13080
aggtgtgaag agtcagtgaa agtgagtgtc cccacacctg tctggccaag gccttgtcat    13140
acctgtgaaa ttttcagaag ccagacagga ccataggatt gccaccaagc tcctgagatg    13200
gggagagtct ggcctgccta ctgtagctgt gtagctccat cctgtgtgtg cccaggttag    13260
ggaatggggt ttccgttcct gttaactcca gtagggtcac aggtgcttcc ccaaacttga    13320
gccttcataa acccaggcag aactgcttct ttgactttga tgaagctgaa tctctggttt    13380
tattcatatt caaaggtgac tgcctgccca ggtgacttta gccattagga cgtgccttga    13440
gtgtggaaca ttccttagat tcttgacctc atgataggga tggatgaagg gttcttgttt    13500
tcccctgtag gatctgaatc cagtttggcc ctgaggctgg tgaatggagg tgacaggtgt    13560
cagggccgag tggaggtcct ataccgagc tcctgggca ccgtgtgtga tgacagctgg    13620
gacaccaatg atgccaatgt ggtctgcagg cagctgggct gtggctgggc catgttggcc    13680
ccaggaaatg cccggtttgg tcagggctca ggacccattg tcctggatga cgtgcgctgc    13740
tcagggaatg agtcctactt gtggagctgc ccccacaatg gctggctctc ccataactgt    13800
ggccatagtg aagacgctgg tgtcatctgc tcaggtgggc ctccaagact tttggtttcc    13860
tctcttgggg tagattttgc tcaggaaggt tttattatgt tctaatctcc tcacttagag    13920
cttttttcaac ttttcctata tttctgatac ctccttagct ctctcctagg aaaccgcatg    13980
agtcttcacc acattgccag ttttgaggag ggtcagagag gacaatgggc caaagtgaaa    14040
taagggtcac acctttgttc ccctactgag gcagcgcaag cagagggaga agacgaaagc    14100
gccgggtctt tgccttttag tgtggctgga aggaatagc tggggccagg ttgttcatga    14160
agatagaggt tgatttgggt cttgggtctt tgcaggctgc ataggagcat ggtgcaggca    14220
tctgctcggc ttctgctgag gacctcaggc tgcttgtact cctggcagag gggatgggga    14280
gctggcctgg gcagaggtca catggcgagg gatgaagcaa gatggcagaa gaagatgggg    14340
aggtggcctg gacagaggtc acatggtgag ggaggaagca agaaagagca agagggaggg    14400
```

```
cccagacagt tttcaaccac cagctctttc taggaactaa gagaagaact taccccctgac  14460 cagggaggac actaagttat tcatgaagag ttggccttca tgacccagac atggcacatc  14520
aagcctcacc tctatacttg gggatccaat cccaacatga gtcttagatg ggacaaacat  14580
ccaaactata gcatgctgcc tctccagggt tccacctttc ccctactgaa aggtttaggt  14640
gagggtgagg tggatgcagc acatataggc attgagggag ggacggtctg actgggagga  14700
ttccagaacc aagggctcat gctgggaagg gagggttttc tgctgaggac taataaggag  14760
gcatcagacc ggaaacacaa ggctgggagt ggagattcgt gactgtccat atctgacctg  14820
ggttttgggg gtgtgagtgc ttgattgcaa ttccctccag agcactgcag tgtcttgcct  14880
gtgcaccggt caggtgtggg gcaggcagtg cccatgaggc ttactgagca aagccttgtt  14940
atgaatgcct gtgggctggg ctagaagatc acaggctgga tattttttttt ttgcaggagt  15000 ggcctcttca tacttgctga ctcagggact gctaagatgt gcaagggagt gggttggttt  15060
tgtgtcaacc tgattactat gggcagacac aaagtccttc aaacaccccc agatgcagca  15120 gggcccatc tacatgcgga aaggcagagg ccgtgctcag gcaaggagag agatattaga  15180
tatttctggt acctccactt gccaggagac tttatactcc tttgggcagc tccctgatcc  15240
ttctaacatt ttagctgtaa caatcagagg ctcagcaatg tgtcagatg tgtccattag  15300 tccatgtgtc agtggatggg gcaggcaaac cctttgtagc tgagaagagg atatcccaca  15360
cttcagaggt aggagggatt ggactggtct ccagcgaggc ctatgtccct tcctgagctt  15420
actgggctga agagttgggc agacacatgg ggagcaagtg gcaaaaacca gaaatccagt  15480
agttttcatg atgcttgccc tatctggaga cttttccttt tggagctttt caccctcaag  15540
tttaattcta gcctttgtct ttgttgcaat taaagacacg ttgccgacca ccacattacc  15600
tgcatcaaca gtaggtacag aatcttctca cccccactag ggctcactct ctacttctgg  15660
acaaatgttt ttttctgaaa atgagaggat gagggtcagg gtgggtccct gtcttttca  15720 tatccctgtg cattgagtgg gaggaagttg gagtctctgg ggagccagtc ctgcttctgg  15780
tgttggaggg tagaggggc tggtgacctg tctcccttgg gatcctcttc caagtatcag  15840
gaaataataa agaaaaaaaa aaaagatcct catccaggtg ctgaggacaa gccctggagg  15900
gctccctact cctattcgac ctcgttcctg gccctccagc catgcactgc agacctgcaa  15960
gggtgggtga cagtttctgt ccctgcagct gtctggccaa agccttgcca tccttggcaa  16020
tttgccagaa gccaggagg accatggggg tgccacctaa ctcttgaaca tggggacagc  16080
atggtcctgc cctctggagc tgtgagctc catcctgtgt gtgccagag tagggagtcg  16140 gttgtctatt cctgtcacct ccactgggt cacaggtgct tccccaaaac ttgagccttc  16200
ataaacccaa ggagaatagt gtatcacctc tccttctact gtgatgaagc tgaacctctg  16260
gttgcagtca tctttaatcg tgactgcctg cccaggtgac tttggccatt aggaagtgcc  16320
ctgagtgtgg aatgtgcctt agatccttga cctgctgata gggattgatg aagggttctt  16380
gtgttctcct ataggacctg aatccagttt ggccctgagg ctggtgaatg gaggtgacag  16440
gtgtcagggc cgagtggagg tcctataccg aggctcttgg ggcaccgtgt gtgatgacag  16500
ctgggacacc aatgatgcca atgtggtctg caggcagctg ggctgtggct gggccacgtc  16560
agccccagga aatgcccggt ttggtcaggg ctcaggaccc attgtcctgg atgatgtgcg  16620
ctgctcagga catgagtcct acctgtggag ctgcccaaac aatggctggc tctcccacaa  16680
ctgtggccat catgaagatg ctggtgtcat ctgctcaggt gggcctccag caatttttggt  16740
```

-continued

```
ttcctctctt ggggtagatt ttgcccagga agagaggtct tatgttctaa tctcctcact   16800
cagagctttt tcaacctttc ctatgtttct gatatctcct tagctctctt ctaggaaact   16860
gcatgagtct tcaccacagt gccaggtttt gaggaggtca gagaggacaa tgggccaaag   16920
tgaaataagg gtcatgcctt tgttccccta ccaaggcagc gcaagcagag ggagaagagg   16980
aaagggctgg gtcttttgcat tttagtgtgg ctggaaagga atggctgggg tcaggttatt   17040
catgaagaaa gaggcagatt tgggtcttgg ctttgcaggc tgcataggag cgtggtatct   17100
gcttggcttc tgctgacagc ctcaggctgc ttgtgctcct ggcagaagga gatggggagg   17160
tggcctgagc agaggtcacg tggcaaggga ggaagcaaga gagggcaaga aggaaggccc   17220
aggctctttt caaccaccag ttcttgctag aaactaagag aagaactcac ccctgatcag   17280
ggagggcact aagttgttca tgaatggttg gcttccatga cccagacatg gcacatcagg   17340
cctcacctct atacttgggg atccaatccc aacatgagtc ttgtatggga caaacatcca   17400
atctatagca cactggctct ccagggttcc atctttcccc cactgaaagg tttaggtgag   17460
ggtgaggtgg atggagcaca tataggtgtt gggggacgga cgatctcacc gggaggagtc   17520
cagaaccaaa ggcttatgct gggaagggag ggtcttccgc tgaggcccag taaggaggca   17580
tcagactgga aacacaaggc tgggagtgca gatctgtgtc tgtccaagtc tggcctgggt   17640
tttgggggtg tgagtgcttg actgcaattc cctccagagc actgcagcat cttgcctgta   17700
caccagtcag gtgtagggcg ggcagtgccc attagggctg ctgagcaaag ccttgttatg   17760
aatgcctgtg ggctgggcta gaagatcaca ggctggattt ttgctggagt ggcctcttca   17820
tacttgctga ctcagggact gctaagacgt gtaaggagag gggttggttt tgtgtcaacc   17880
tgattactgt gggtagacac aaacttaatc actttggagc tggcagtagt ggacaagatc   17940
tgcccagatg cctttcaagg agcatctttg tggggacgtg catggcaatg cccctccctc   18000
tgtgatgggg acataggggtg gactgaaggc gctaccagtt tagttccttg tacctttgtt   18060
ctggttttgc cagcttctgt atagtgcatc tgatctgacc tcctctttct cacagctgcc   18120
cagtcccggt cgacgcccag gccaggtgag tccccagtgt ccttccttgg gatgtcccct   18180
ttctttctgc acaattatcc ttttttccat tccacagagc cctccttctt acctgtgtgg   18240
atactgtggg tcatactatt ttccctgctc tgtaactgag accctagcat ggagcttct   18300 aaccagacat ggttaagaag gtatgatctt tctaagaatt gagagtgatt gccaaagtct   18360
cctgggaagg caatttcagc taaagcctta aacatgcctg tccatgggca agaatgtcag   18420
tgcaggcctg atacctccat tcctcactcc ttcagacacc cccagatgcg gcagggcccc   18480
atctacctcc agacaggcag aggctgtgct caggcaggga gagcgatatt agatatttcc   18540
gttgcctcca cttgccagga gactttatac tcccttaggc agctccctga tccttctaac   18600
attttagttt caagcgtgag aggctcagca ttggtgtcag atgtgcccat cagtccatgt   18660
gtcagtggat ggggcaggta aacccttttgt agctgagaag agggtattcc acacttcaga   18720
ggcaggaggg atcggactgg tctccagtga ggactatgtc cctggctgtg cttcctgagc   18780
tacagacttg ggcagacaca tggggagcaa gtggcaggaa ctagaaatgg aagaatattc   18840
atgatgcttg ccttgtccag agaccttttcc tttgggagct tttctccctc aactttaatt   18900
ctagcctttg tctttgttgc aatttacaga cacgttgtcg accatcacgt tacctccatc   18960
gacagtaggg aaataatcct ctcacccctc cctagggctc actctctacc tctgacaaa    19020 tgttttctct gaaaatgata ggatgagggt caaggtgggc cctgtctttt ttcacatccc   19080
tgtgcgctga gtgggaggaa gttgagtctc tggggaacca gtcccgggtc gggtgttaga   19140
```

-continued

```
gggtggaggg tgttggtgac ctatctcctg ttggaccgtg ttccaagtat cagtaaagat    19200
cctcattcag gtgctggaca aaccctggag agctccctac tcctgggacc tcattcctgg    19260
ccttctggcc atgcattgca gacctgcaag ggagggtgaa aatttctgtc cctgcagttg    19320
tctggccaat gtgttgccat ccctggcaat ttgccagaag ccagagagga ccacgtgggt    19380
gccaccaaac tcttcgacat ggggatagca taggcctgcc ctctggagca gtggagctcc    19440
atcctgtgtg tgctcagagt agggagtggg gtgtccattc ctgtcacctc cactggggtc    19500
acaggcgctt tcccaaaatc tgagcctcca taaacccagg cagaataggg tatcacctct    19560
ccttccagta tgatgaagct gaacctctgg ttgcagtcgt attcaatcgt gactgcttgt    19620
ccaggcgacc ttggccatta ggaagtaccc tgagtgtgga acgtgcctta gatccttacc    19680
tcatggtagg gatggataaa gggttcttgt gttccctgt aggatctgaa tccagtttga    19740
ccctgaggct ggtgaatgga agtgacaggt gtcagggccg agtagaggtc ctataccgag    19800
gctcctgggg caccgtgtgt gatgacagct gggataccaa tgatgccaat gtggtctgca    19860
ggcagctggg ctgtggctgg gccacgtcgg ccccaggaaa tgcccggttt ggccagggct    19920
caggacccat tgttctggat gatgtgcgct gctcaggaca cgagtcctac ctgtggagct    19980 gccccacaa tggctggctc tcccacaact gtggccatca tgaagatgct ggtgtcatct    20040
gctcaggtgg gcctccaaga ccttgggctc cctctcctag actggagttt gctcaggaag    20100
aaaatcctaa ttcattctg atctcctcac tcaaagattc ttctatgttt cctatattta    20160
tgtagtcttg ttagctctct gctaaggatc tgtatgaatt ttactacagg gcttggtgtt    20220
cctgtggtca cttaggacag gccccaaact gaaacaacaa cccagacttt atcccttcc    20280 tgaggcagtg caagaaagag gccgaagaga aaactgctgg ctccccaggg ttccatttct    20340
cctcagctga gtagcactgg gtgagggtat catggacata ggacagacag caaggtaggg    20400
gaggaatcct ctcactgaga ggaactctga gctaaagatg cttgtctgaa agtgagttct    20460
cagctgagac ccagtgagga ggtctggaaa tagaggctca agggttagga gtgcaaatgg    20520
gtgtctggtt ctatcaggcc tgggttgtgt gaggttggag tccttgacct caggtcctct    20580
cagaacgctg cagagcactg ccttgccctg ggtctggtgt ggggagggca gcccccatga    20640
gacaggccag gcatggcctt gttattgcct gtggtcgggg cttgaagatc acacaaggga    20700
ttttggctgg agtggcttcc tcagccttgc tgactcagga acacctaaga tgtgcaaggg    20760
agtgggttgg tttaggtcaa ccgggttacc ctgggcagac acaatttgat cacctcagag    20820
ctggcaatag tggaaggatc tgcctcgacc ccttacacgg tgcatctctg tggggatgtg    20880
catggcaatg tccctccctg tgtgatagga actaggatga actgagtgtc agactcgctc    20940
atttctttcc ctcctcgttc cagttttgcc gacttctgtg taatgttcct gatctgacct    21000
tctcttctct ttctcacagt ttcccagtcc cggccgacac ccagtccagg taggtcccca    21060
gtgtccttcc tcaaaatgtc ccttctcttt ctgcccaatc accccttcca cactccacag    21120
agctctcctg tttctctgtg tggatactgt ggggcatatt atttccaccc caacaccgg    21180 ctgtgtaact gagaccccag cacagcgctt tttaaacaca cacaggattg aggaggcctc    21240
tgtcttcttt tcaaccctc tcagctttca tgaaacagtt tcatactgtc ccagtggaca    21300
acccttacag gttcaggaag tggccccatg tttaatgagc tttggtcctt ttatattccg    21360
gactcacata tagtttctga aaattgaggg tgtcaccctc tgacccgttc aaggcatcgt    21420
cagggcaggc tcgataccc catccatcac tgctggaaac attccgagat tatgattccg    21480
```

```
agatttctat ccagaagagg cagagtttgt gctcgggcag ggagagggat aataaaggtt      21540
tgtgatgtct ctgcttaacc agaaacctga ttcctgattg tcccctgggc agcccctggt      21600
tcccctaaca ttttacctgg cagtgtccga gcctcagcaa tggcgtctga tgtcctagtc      21660
agtccatgca tcagcagatg tgggatggca tggtgggggc atcctctaac agatagaaag      21720 atacccagg attagagaaa tggagggctc agtctggtct ccagcaggac ctttgtccct       21780
ggatgagttc acagcacagg agacctggga agacacatgg gaaacaaatg gcaggaacaa      21840
gaagtggaat tgttgtcacg ttgattcctc ctcccagaga tccttttgtt ctgtgccttt      21900
tcccttcaag tctaattctg tcttttcctt ttgttgcaat ttacagatac ttggccgacc      21960
tcacatgcat caacagcagg taaataaccc tctcacccct ccctaggact cactatctct      22020
ggacatattt tgtgtttgaa actgatagga tgaggctcaa tgtgggcttc tctgttttca      22080
tgtccctgtg ggttgcgtgg gaggaaggtg gaatctctga ggagccagtc ctgggtctga      22140
tgtttgagga cggagggtgt tggtgacctg tctcccatgg aatcctgttc caagtggtca      22200
ggaaagatcc tcatccaggt gctcaggacg agcactggag ggctccttaa tgctgctggg      22260
acctcattcc tggccctcag gccatgggat ccagacctct gaagagcggg tgaaagtgcc      22320
ggtccctgca cctgtgtggc caaggccttg ccatcactgg caatttgcca gaaggcagag      22380
aggcccatgc aggtgccaat aagctcctga atatggaggg ggtctaggcc tgtcatttgt      22440
agctgtgtag ctccatcctg tgttcaccca gagtggggag tgggtgtcc attcctgtcc       22500 tctcctctgg ggtcatacat gcttaccat agcttgagct tttatagact tgagtagaat       22560
agggcatcac ttttccact atgaccaagc ttaacctctg ggtgcagcca tctgccattg       22620
tgactgcgtg ccctggtgac ttacgtgccc tggtgacttt ggcatttgta ttcaaacttg      22680
actacttttc ccattgccct gagtgttgtc catgcctttt ccttcacctc agaatggaga      22740
tggatgaagg attcttgtgt tccctgtag gatctgaatc cagtttggcc ctgaggctgg       22800
tgaatggagg tgacaggtgt cagggccgag tggaggtcct ataccgaggc tcctggggca      22860
ccgtgtgtga tgatagctgg gacaccagtg acgccaatgt ggtctgccgg cagctgggct      22920
gtggctgggc cacgtcagcc ccaggaaatg cccggtttgg ccagggttca ggacccattg      22980
tcctggatga cgtgcgctgc tcaggctatg agtcctacct gtggagctgc ccccacaatg      23040
gctggctctc ccataactgt cagcacagtg aagacgctgg tgtcatctgc tcaggtgggc      23100
ctccaagacc ttgggctccc tctcttgggg tagattttgc tcaggaagcg aggtctcatt      23160
atgttctgat ctcctcactc agagcttttt cagcctttcc tatatatctg atatctcctt      23220
agctctctcc taggaaactg catgagtctt cattgccagg ttttgaggag gtcaggtagg      23280
acaacgggcc aaagtgaaat aagggtcacg cctttgttca cctaccgagg cagcgcaagc      23340
agagggagaa gaggaaagtg ccaggtcttt gccttttagt gtggctggaa aggaatagct      23400
ggggctggtt tgttcatgag gaaagaggct gatttgggtc ttggctttgc aggctgcata      23460
ggaccatggt gcaggcatct gctcagcttc tgatgagggc ctcgggctgc ttgtactcct      23520
agcagaaagg gatggggagg tggcctgggc agaggtcaca aggtgaggga ggaaggaaga      23580
gagagcaaga ggagggctc agactcttca accaccagct cttgctagga actaagagaa       23640
gaactcaccc ctgaccaggg aggcactaa gttattcatg cagtgttggt ctccatgacc       23700
cagacctggt gcatcaggcc tcacctctaa acttggggat tcagttgcaa tataacactt      23760
ggatgtgaca agcctctaaa gtatagcacc ctggctctcc agggttccat ctttccccta      23820
ctgaaagatt ttgcaaaggg ttacatggat gaagcacata tagaggatgg gggagggact      23880
```

-continued

```
gtctccctgg gaggagccca gaaccacagg ctcctgctag gaagcgcggt cttctgctga    23940
ggcccaataa ggtgatgtct taatagagac acaaggctag gagtgcggat gtgtgtctgt    24000
ccctctctgg cctgagattt gggggctgtg agtccttgac cacaactccc tccagagcac    24060
tgcagtgtct tgcctgtgca ccggtctggt gtggagtgtg cagtccccat gaggtctgct    24120
aggcaaagca ttgttatgaa cgcctgtggg ctggactgga acatcagagg caggactttg    24180
gctggagtgg cctcctcaca tttgctaact cagggactgc taagacatgc aaggagagg     24240 gtaggttttg tgtcaacctg attactatgg gcagacacaa ggttaatcac cttggagttg    24300
gcaatagtgg acaggatctg cccagacacc ctccaaggag catctctgtg gggacatgca    24360
tggcaatgcc ctccctctgt gatggggacc tagggtggac tgaaggcatg atctgtttag    24420
ttccttccac ctttgttccg attttgccag cttctgtata gtgcatctga tctgacctcc    24480
tctttctcac agctgcccac tcctggtcga cgcccagtcc aggtgagtcc ccagtgtcct    24540
tccttgggat gtcccttctc tttctgtata attatccctt tctgcactcc acagagccct    24600
cgttcttctc tgagtgaata ctacatggca tacaattttc ccctgctctg taactgagac    24660
cctggaatgg cgcttctgaa ccagacatag ggttcaagag gcttctgtct tctgttccat    24720
ttatctcagc tttcatgaag cagtttcata ctgtcccaat ggccaaccct tagaggttta    24780
ggaagtgacc tcatatttaa ttagctttgg cacttttcta ttcagagctg atatgacctt    24840
cctgagaatt gagagtgatt gccaaagtct cctgggtagc caatgtcagc taaagcctta    24900
aacatggctg ccgccacagg caagcaatgt cagtgcaggc ctgacacctc ccttcctcac    24960
tccttccaac accccagatt ctgcagggct acatgtgcat ccagaagagg cataggccat    25020
gctcgggcag ggagagggat aataaatatt tctggtgcct ccacttactg ggaaacttga    25080
tacccctttg gtcagctcct tggtttccct aacattttag ctcgagctag tagagtgtca    25140
gcaatggtgt tagatgtacc cgtcagtgca tgtgtcagtg catggaacag gctaacccct    25200
tgtgactgag aagaggacat cccacacttc agaggcagga gggatcgaac tggtctccag    25260
caaggcctat gaccccttgct gagcttgctg agctgcagac ttgggcagac acatggggag    25320
caagtggcag gaaccagaag tggggtagtt ttcatgatgt ttgccttctc cggagacctt    25380 tcctttttgga gattttcacc atcaactttta attctagcct ttgtctctgt tgcaattaca    25440
gacacattgc cgaccatcac cttgcctgca tcgacagtag gtaaatattc ctctcgcccc    25500
tccctagggc tcactctcta cctctggaca aatgttttt ctgaaaatga taggatgagg    25560
gtcaaggtgg gcccctctct ttttcatgtc cctgtgggtt gcatgggagg aagtagcgt    25620 ctctggggac ccagctctgg gtctgatgtt ggaggctgga gggtgctggt gacttgtctc    25680
ccgtggaatc ctgttccaag tggtcaggaa acatcctcat ccaggtgctg aggaaaagcc    25740
ctggagggtt ccctaatcct actaagacct cattcctgtc cctcagccca tgggctgcag    25800
aggtgtgaag agtcggtgga agtgactgtc cccacacctg tctggccaag gccttgtcat    25860
acctgtgaaa ttttcagaag tcagacaaga ccataggatt gccaccaagc tcctgagatg    25920
gggagagtct ggcctgccta ctgtagctgt gtagctctgt cctgtgtgta cccaggttag    25980
ggaatggggt ttccattcct gttaacttca gtagggtcac agatgcttcc ccaaaacttg    26040
agccttcata aacccaggca gaatagggtg tcactgcttc tttgactttg atgaagctga    26100
atctctgatt ttattcatat tcaaaggtga ctgcctgccc aggtgacttt agccattagg    26160
acatgccttg agtgtggaac attccttaga ttcctgacct catgataggg atggatgaag    26220
```

```
gattcttgtg ttccctgta ggatctgaat ccagtttggc cctgaggctg gtgaatggag   26280
gtgacaggtg tcagggccga gtggaggtcc tataccaagg ctcctggggc accgtgtgcg   26340
atgacagctg ggacaccaat gatgccaatg tcgtctgcag gcaactgggc tgtggctggg   26400
ccatgtcagc cccaggaaat gcccggtttg gtcagggctc aggacccatt gtcctggatg   26460
atgtgcgctc tcaggacac gagtcttacc tgtggagctg cccccacaat ggctggctct   26520
cccacaactg tggccatagt gaagacgctg gtgtcatctg ctcaggtggg ccttcaagaa   26580
cttgggatca ctctcttggg gtggagtttg ctccagaaga aactcctaat tacattctga   26640
tctcctcact caaagcttct tctatgtttt ctatatttct gaagacttgt tagctctctg   26700
ctaagaatcc ctatgtactc actgcctagt gttcctgtgg tcacttagga caggggacca   26760
aactcaaaca acccagagtt tttccccttc ctgagggaag gcaaggaaga ggcagaagag   26820
aaaagtgctg gctccccagg gctccatttc tcccctgctg agtagcacgg tgtgagggta   26880
taatggatgc aggacagaca gcaaggcggg gtagggatcc tctcactgtg aggaactctg   26940
aactaaagat gcttgtctga agtgggttc tcagctgaga cccagtgagg aggtctggaa   27000
atagaggctc aagggttagg agtgcaaatg ggtgtctgat tctatcacgc ctgggttgtg   27060
tgaggttgga gtccttgacc tcaggtcctc tcagatcact gctgagcatt gcctgtgccc   27120
caggtctggt gtggggaggg cagcccccat gaggccggcc aggcatggcc ttgtcattgc   27180
ctgtgatcag ggcttgagga cggcacaagg gattttggct ggagtggctt cctcagcctt   27240
gctgactcaa gaatgcctaa gacgtgcaag ggagagggt ggtttaggcc aaccgggtta   27300
ccctgggcag acacaagttg atcacctcag agctggcaat agtggacagg atctgcctcg   27360
accccttaca tggtgcatct ctgtggggat gtgcatggca atgcccctcc ctgtgtgata   27420
ggaactagga tggactgagt gtcagactcg cccatttctt tccctcctcg ttccactttg   27480
ccgacttctg tgtaatgttc ctgatctgac cttctcttct ctttctcaca gcttcccagt   27540
cccggccaac acctagtcca ggtgggtccc cagtgtcctt cctcaaaatg tcccttctct   27600
ttctgcccaa tcacccttc cacactccac agagctctcc tgtttctctg tgtggatact   27660
gtggggcata ttatttctac ccccaacacc agttgtgtaa ctgagacccc agcacagcgc   27720
tttttaaaca cacacaggat tgaggaggcc tctgtcttct tttcaacccc tctcagcttt   27780
catgaaacag tttcatactg tcccagtgga caaccttac aggttcagga agtggcccca   27840
tgtttaatga gctttggtcc ttttatattc cggactcaca tatagtttct gaaaattgtg   27900
agtgtcaccc tctgacctgt tcaaggcatc atcagggcag gctcgatacc cccatccttc   27960
actgctggaa acattccgag attatcatgg gccacatttg tatccagaaa aggcagagtt   28020
tgtgcttggg cagggagagg gataataaag gtttgtgatg tcactgctta accagaaacc   28080
tgattcctga ttgtccctg gcagcccct ggttccccta acattttatc tgccagtgtc   28140
cgagcctcag caatggcgtc tgatgtccta gtcagtccat gcatcagcag atgtgggatg   28200
gcatggtggg ggcatcctct aagagataga aagatacccc aggattagag aaatggaggg   28260
ctcagtctgg tctccagcag gacctttgtc cgtggatgag ttcacagcag aggagacctg   28320
ggaagacaca tgggaagcaa gtggcaggaa caggaagtgg aattgttgcc aggtggattc   28380
cccctcccag agaacctttt gttctgcacc ttttcccttc aagtctaatt ctgtctttc    28440 ctttgttgca atttacagac acttggccaa cctcacatgc atcaacagca ggtaaataat   28500
cctctcaccc ctccctaggg ctcactgtct ctggacatat tttgtgtttg aaactgatag   28560
gatgaggctc aaggtgggcc cctcttttt cactcccctg tgggttgcgt gggaggaagg    28620
```

```
tggaatctct gaggagccag tgctgggtct gatgtttgag gatggagggt gctggtgact      28680
gtctcccatg gaatcctgtt ccaagtggtc aggaaagatc ctcatccagg tgctcaggat      28740
gagcactgga gggctcctta atcctactgg gacctcgttc ctggccctca ggccatggga      28800
tccagatctc tgaagagcag gtgaaagtgc cagtctctgc acttgtgtgg ccaaggtctt      28860
gccatcactg gcaaattgcc agaaggcaga gaggaccatg caggtgccaa tgagctcctg      28920
aattcggagg gggtctgggc ttgtcatttg tagctgtgta tctccatcct ttgtgtaccc      28980
agagtgggga atggggtgtc cattcctgtc ccctcctctg gggtcataca tgcttaccca      29040
tagcttgagc ttttatagac ttgagtagaa tagggcatca cttttccac tatgacaaag       29100 cttaacctct gggtgcagct atcttccatc atgactgcat gccctggtga cttctgcatt      29160
cgtattgaaa cttgactact ttgcccactg ccctgattgt tgtccatgcc ttatccttga      29220
cctcatattt gagatggatg aagcgttctt gtgttcccct gtaggatctg aatccagttt      29280
ggccctgagg ctggtgaatg gaggtgacag gtgtcagggc cgagtggagg tcctataccg      29340
aggctcctgg ggcaccgtgt gtgatgacta ctgggacacc aatgatgcca atgtggtttg      29400
caggcagctg ggctgtggct gggccacgtc agccccagga aatgcccggt ttggccaggg      29460
ttcaggaccc attgtcctgg atgatgtgcg ctgctcagga catgagtcct atctgtggag      29520 ttgccccac gatggctggc tctcccacaa ctgtggccat catgaagacg ctggtgtcat       29580
ctgctcagnn nnnnnnnn                                                    29598

<210> SEQ ID NO 7
<211> LENGTH: 28720
<212> TYPE: DNA
<213> ORGANISM: Homo sapiens gatctgcctc aacccttac acggtgcatc tctgtgggga tgtgcatggc aatgtccctc        60
cctgtgtgat aggaactagg atggactgag tgtcagactc gcccatttct ttccctcctc      120
attccagttt tgtcgacttc tgtgtaacat tcctgatctg accttctctt ctctttctca      180
cagcttccca gtcccagccg acacccagcc caggtaagtt cccagtgtcc ttcctcaaaa      240
tgtcccttct ctttctgccc aatcacccct tccccactcc acagagctct cctgtttctc      300
tgtgtggata ctgtggggca tattatttct accgccacca ccggctgtat ttcacatggg      360
tccttttcta ttttccctaa gtgtcagccg gtctgagaaa taagggaag gcatacaaaa       420 gagcaaaatt ttaaagctgg gtgttggggg gagacatcac atgtcagcag gttccgtgat      480
ccctcctgag tagcaaaacc agcaagtttt tattggtgat tttcaaaagg ggagggagtg      540
cacaaatagg gtgtgggtca cagagatcac atccttcaca aggtaataaa atatcacaag      600
gtaaatggag gcagggcaag atcacaggac tggggtgaaa ttaaaattgc taatgaagtt      660
tcgggcacgc attgtcattg aaaacatttt atcaggagac agggtttgag agcagacaac      720
tggtctgacc aaaatttatt aggaggcaat ttcctcatcc taataagcct ggaagcgcta      780
cgggggaccg gggcttattt catcccttat ctgtaagcgt aaaagacaga cgttcccaaa      840
gcggccattt cagaggcctc cccttaggaa cacattctct ttctcaggga tgttccttgc      900
tgagaaaagg aattcagcga tatttctcct atttgctttt gaaggaagag aaatgtggct      960
ctgttctgcc tggcccacag gcagccagcc tttaaggtta tctcccttgt tccctgaaca     1020
acgctgttat cctgttcttt tttcacagtg cccagatttc atattgttta aacaatttct     1080
gcagttaacg caatcatcac agggtcctga ggtgacattc atcctcagtt tatgaagaag     1140
```

```
atgggattaa gagattaaag taaagacagg cataggaaat cacaagagta ttgattgggg    1200
aagtgataag tgtccatgaa atcttcacaa tttatgttca gagattgcag taaagacagg    1260
cgtaagaaat tataaaaata ttaatttggg gaactaataa atgtccatga aatcttcaaa    1320
tttatgttct tgtgccatgg cctcagccgg tccctctgtt tggggtccct gacttccgc     1380 aacacagcac agtgctttga aaacacacat aggattcagg aggcctctgt cttcttttca    1440
acccctctca gctttcatga aacagtttca tactgtccca gtggacagcc cttacaggtt    1500
caggaagtgg cccccatgttt aatgagtttt ggtcctttta tattcaggac tcacatatag    1560
tttcgaaaat tgagggtgtc accctctgac ctgttcaagg cattgtcagg gcaggctcga    1620
tacccccatc catcactgct ggaaaaattc tgagattatg atggaccaca tttgtatcca    1680
gaagaggcag ggtttgtgct tgggcaggga aagggataat aaaggtttgt agtgtctctg    1740
cttagccaga aacctgattc ctgattgtcc cctgggcagc ccctggttcc cctaacattt    1800
tatctgccag tgtctgagcc tcagcaatgg catctgatgt cctagtcagt ccatgcatca    1860
gcagatgtgg gattgcatgg tgggggggcat cctctaacag atagaaagat accccaggat    1920
tagagaaatg gagggctcag tctggtctcc agcaggacct tgttcatgg atgagttcac      1980 agcagaggag acctgggaag acacatggga agcaagtggc aggaacagga agtggaattg    2040
ttgccaggtt gattccccct cccagagaac cttttgttct gtgccttttc ccttcaagtc    2100
taattctgtc ttttttcttt gttgctattt acagacactt ggccaacctc tcgtgcatca    2160
acagcaggta aacaatcctc tcaccctcc ctagggctca ctatctctgg acatattttg     2220
tgtttgaaac tgataggatg aggctcaagg tgggcccctc tcttttcatg tccctgtggg    2280
ttgggtggga ggaaggtgga gtttctaggg agtcagccct gggtttgatg tttgaggatg    2340
gagggtgctg gtgactgtct ctcatgggac cctgttccaa gtgttcagga acgatcctca    2400
tccaggtgct caggacgagc actggaaggc tccctaatcc tgctgggacc tctttcctgg    2460
ccctctgacc acgcactgca gacctgcaag ggtgggtgaa aatttctgtc cctgcagctg    2520
tctggccaag tccttgccat ccctggaaat ttgccagaaa ccagagagga ccatgtggat    2580
gccaccaaac tcttaaacat ggggccagca tgggcctgct ctctggagct gtggagctcc    2640
atcctgtgtg tgcccagagt agggagtggg gcattcattc ctgtcacttc cagtgggggtc   2700 acaggtgctt ccccaaaatc tgagcctcca taaacccagg cagcatagtg tatcacctct    2760
cctttcccta tgataaagct gaacctccgg tagcagttgt atgcaattgt gactgcttgc    2820
ccaggtgact ctggccatta ggaagtaccc tgagtgtgga acttgcctta gattgttgac    2880
ctcctggtgg ggatggatga agggttcttg tgttcccctg taggatctga atccactttg    2940
gccctgagac tggtgaatgg aggtgacagg tgtcgaggcc gagtggaggt cctataccaa    3000
ggctcctggg gcaccgtgtg tgatgactac tgggacacca atgatgccaa cgtggtctgc    3060
aggcagctgg gctgtggctg gccatgtca gccccaggaa atgcccagtt tggccagggc     3120
tcaggaccca ttgtcctgga tgatgtgcgc tgctcaggac acgagtctta cctgtggagc    3180
tgcccccaca atgctggct ctcccacaac tgtggccatc atgaagatgc tggtgtcatc      3240
tgctcaggtg ggctttcaag accttgggct ccctctctta agttgaagtt tgctcaggaa    3300
gaaaatccta attacattct gatctcctca ctcaaagctt tttctatgtt ttctatattt    3360
ctgaagtctt gttagctctc tgctaagaat ctttatgaat tttgctacag tacctggtgc    3420
agctgtggcc acttaggcca gggctccgaa ctgaacaac aacccagact ttatccccat     3480
cctgaggcag tgcaaggaag aggcagaaga gaaaagtgct ggctccccac ggctccattt    3540
```

-continued

```
cttccctgct gagtagcact ggttgagggt atcgtggaca cagcacagat agcagggca    3600 gggagggatc ctctcactac aaggaactgt gaactaaaga tgcttgtctg gaagtgggtt    3660
ctcagctgag acccagtgag gaggtctgga aatagaggct caagggttag gagtgcaaat    3720
gcatgtctgt ttgtgtcagg cctgcttgga gtccttgacc tcaggtcctc taagaatgct    3780
gcagagcact gcctgtgccc caggtctggt gtggggaggg cagcccccat gagtctggcc    3840
aggcatggcc ttgttattgc ctgtggtcgg ggctgtaaga tcacacaagg catttgggct    3900
ggagtggcct cctcagcctt gctgactcag gaactgccaa acatccaag ggagagtgtt    3960 ggttttgggt caacctggtc accctgggca gacacaaagt tactcacctc ggagctgaca    4020
atagtggcca ggatctgcct gcaccccta tatggtgcat ctctgtggga atttacatgg    4080
caatgcccct ccctctgtga tagggactag gatggactga gtgtcaggct tgcccagttc    4140
cttctatctt tgttccagtt ttgccattt ctgtatagtg catctgatct gaccttctct    4200
tctctttctc acagctgctc agtcccagtc aacgccagg ccaggtgagt ccccagcatc    4260
cttcatcggg atgtccttc tctttctgcc cagttacctc ttccccactc cacagagctc    4320
tcctgctttt ctgtgcggat actgtgggc atattatttt tcctcccacc actctgtaac    4380 tgagaccca gcatagtgct tcaacagaca taggtcag gaggcttctg tcttctgttc    4440 aatttattc aggtttcatg aagcagtttc atactgtaca atggacaagc cttacaggtt    4500
caggaagtgg cctcatgttt aatgagcttt agctcattta tattcagagc tgatacaacc    4560
tttctgagaa ttgagagtga ctgccaaagt cacctgggaa ggcaatgtca gttcaagcct    4620
taaacatgac ttctgccatg ggcaagcaat gtcagtgcag gcctgatacc tccgtccctc    4680
actccttcaa atacccaga ttttgcaagg ccatatctgc atccagaaaa ggcagaggcc    4740
atgctcgggc agggagagg ataataaata tttctggtgc ctccacttat caggaaactt    4800
gatacccctt tgggcggctc cttggttccc ctaacatttt agctcgaact gtcagagtct    4860
cagcaatggt gtcacatgtg cccatcagtc catgtgtcac tggatgggc aggctaaccc    4920 ttcgtagctg agaagaggac atctcacact tcagaggtag gagggatcga actggtctcc    4980
agcaaggcct ttgttcctgg ctgtgctcac tgagctgaag acttgggtag cacttggagc    5040
aagtggcagg aaccagaaat tgaatagttt tcatgatgct tgcctggttc agagattttt    5100
ttttgtagct ttcctccctc aagtctaatt ttgtccttc tctttgttgc aatttacaga    5160
tacttggctg accaccaact taccggcatt gacagtaggt aaataatcct ctcgcccctc    5220
cctagggctc actctctacc tctgacaaa cgtttctttt gaaatgaaa gaatgaggct    5280 caagctggcg cctctgtttt tcatgtttcc gcgagttgcc tggggaggta gactccctgg    5340
gaacctagtc ctgggtcaga tgttggaggc tggagggtgc tggtgacctg tctcccctgg    5400
gattctgttt tatgtagtca ggaaagatcc tcagccaggt gctcaggaca agccctggag    5460
ggctccctaa tcctactggg accttgttcc tggccctcag ccacaggct gcagacctgc    5520 gaatagtggg gaaagtgcct gtccccatag ctgtctggcc aatgtcctac cattcctggc    5580
actttgctag aagccagaga ggatcatgtg ggtgccacca aactcctgaa cgtgaggcag    5640
gtcttggcct cctatctgga gctgtgcagc ttcatcctgt gtgagaatgg agctcacaat    5700
gaggagtgag gcgtccattc ctgtcacctc cagtggggtc acaggtgctt ccccaatact    5760
tgagcttcca tagacttggg tggagtagga catcactgct tcttccacta tcatgaagct    5820
gaacctctgt ctgtattcat attcaaaggt gattacctgc acacgtgact ttggccaatt    5880
```

```
aggaagtgcc ctgagtgtgg aacattcctt aaatccttga cctcataatc agtatggatg    5940
aagggttctt gtgttcccct gtaggatctg aatccagttt ggctctgagg ctggtgaatg    6000
gaggtgacag gtgtcgaggc cgagtggagg tcctgtatcg aggctcctgg ggaaccgtgt    6060
gtgatgacag ctgggacacc aatgatgcca atgtggtctg caggcagctg ggctgtggct    6120
gggccatgtc ggccccagga aatgcccggt ttggccaggg ctcaggaccc attgtcctgg    6180
atgatgtgcg ctgctcaggg aatgagtcct acctgtggag ctgccccccac aaaggctggc    6240 tcacccacaa ctgtggccat cacgaagacg ctggtgtcat ctgctcaggt gggccttcaa    6300 gacctgggc tccctctctt ggggtggagt ttgctccaga agaaactcct aattacattc    6360
tgatctcctc actcaaagct tctcctgtgt ttcctgtgtt tttgaagact tgttagctct    6420
ctgctaagaa tccatatgaa ttcactgcct agtgttcctg tggtcactta ggacagggga    6480
ccaaactgaa acaacaaccc agactttatc cccttcctga ggcagtgcaa ggaagaggca    6540
gaagaaaaaa tttctggctc cccagggctc catttctccc ctactgagta gcactgggtg    6600
agggtatggt ggacacagca cagacagcgg ggcagaggag ggatcctctc cttaggagga    6660
ggctcatggt aaggaaagga catatgttgg ggtagggaat tctcacttga ggccccagta    6720
aggagcattt ggattggagg catatgggct aagagtgcaa acgggtatct gtgcatgtgt    6780
gacctgggtc ttggtcagtt tcagctcctt ccaaagaact gcagtgcatt gtgtgtctag    6840
caagcatggt gttgggaggg cagctcccat gagatctgcc aggcaaagcc ttgttattac    6900
gtgtggtttg ggatggaaga tcacacaggg gattttttgct ggagtggtat cctgagactt    6960
gctgacttgg tgaattgcta aaacctgcaa gggaaagggt tggttttggt tcaattggac    7020
atcacatcca gacacagagt taattgcctt ggagctggaa atggtggaca gaatctgctt    7080
ggatccctta taaggagcgt ctttgaatcc agccaaagca ctagcattca gcaggtctgg    7140
gtgaaactcc tgggtcttgc ttgaagcctc tggccgctcc ctacctcaat caatgtggta    7200
tctaccagtt gtcaattgat ctttaaagag gatctattat tagggatgct tttgtttgca    7260
catggcagga actcaactca aacactctta agctagaaag gaattcattg tctcagttat    7320
ccagaatgtt tagtggtgga tctggagctt caggtacagc tggttccaga agttccaagt    7380
cttttttccc catgctttgc ttacatctac tcttttatct gtgtgggctt cactatcaac    7440 ttgcttttg catgtggctg agagacagca gtgggcagcc ccaagtctat atcccaccag    7500
gagaaggagt cagtctgtcc cagtacctct ggctgacaag gcctgggagg actttgattg    7560
acctgcttgt aaacaggtgc tttcttccaa accatctcta ttagctctga cggctcagcc    7620
agagttctat acccatcttt gtgttccttt ggggcgacgg gaaggatggg ggcactaggc    7680
tctacttgaa tcttgtagga tgctacttttt aaaatagga atgactgttt ctattagaat    7740
aaaaaacagg caggatgttt gtgacagaga tagccatccc tcagttggac ccttcctttc    7800
ttttgatact atctgctctt tgctggttga cgttaccccct ctatcctgag atggaacctt    7860
ccctctccct ggctgttgcc catgttcatt accatcatct ctatctagtt ccaggacttt    7920
ttcattatcc ccaactgaaa gctcttaccc cttaaccatt cataatccat ttctctttcc    7980 ctcagccccct ggcaaccact aatctgcttt ctgcctctgt atacagattt tactaagaat    8040
tgtggtcact ttctatgaat ggaatcatag ccttttctgt ctggcttcat tcacttaaca    8100
taatgttttc aaggttcatt catattttag catgtgtcag aactccacta cttttaactg    8160
ccaactaata ttccattgta tggctacgcc atctttgtct atccatttat cagcttatgg    8220
acatatgggt tgcttccatc ttttggctgt tgtgaataag tctgctatga gaattagtgt    8280
```

-continued

```
acggttttttt gtttgcactt gtgtttccaa ttttgggaga tatataccta ggagtgggat    8340
tgctcggtaa tagggtaatt atgtttaatt tattgtggaa acactgaaca gttgccacag    8400
ctgctgcacc aaatttgcat tcccccaagc aatgcctgag aattctgatt cctccgtatc    8460
ctcaccaaca cttgttatga tgtctttttc atcatggcca tcctagtggg tgtaaggtgg    8520
tatttcatgg tgttttgatt tgcatttcct tgatgactaa tgatgttgag catcttttca    8580
tgtgttggtg ggccctttgt atatattctt gggagaacag gggcttcatt ttatagatac    8640
taagctgaag gccagaggaa ctagactaat gtcagtatct tagcccaggc tcacaggaca    8700
gggttcaggt acacagaggg atcaggatgc ctggcccagt gttgtgtcta gcatgtgaca    8760
ttccttcatg gaggcctaac tctgccattt tttctccatt tcaggcata ggcactgcta     8820 ggtatgcaca actaagtgtc ctcatagttg cttctgccca ctgtccctgt agctcatggt    8880
attcagtagg tccaggtttt gtttcagatt gaaggcaagc tgtgggtttg aaagtgactc    8940
aggaataagc ctcgggcctg atggggtggt ccctgtgagc agagtgagtc agccagaggt    9000
ggagaggtgg actctcccaa gaaccaggtc ctagggctgc accttgccag gcagctggga    9060
gctggtctcg gttgcatcct gctgcagggg cacttgagcc cagtggtccc tgcagatcca    9120
tgctgatggc tcctgcactt taacctctga atctgaaggc ctggctcagc acttgaattg    9180
ctggtcactg gggtaactcc atcagagaac atgcacagct cagtccacac ccaagggttc    9240
tagaaaacaa cccttaagtt gatgaagaac atcaacttaa aatgatgaag aacaggcttc    9300
cgtcaatgtc tatgctgctg gagaacatta actggagacc cagaaacctt ggccttctgg    9360
aagaattctg aacttcactt gacctcagat cctcttcctt taggagatac aggagagagt    9420
taattttcct gtcttttcta gaatccaatt ctggtttggc cctgaggctg gtgaatggag    9480
gtgaccagtg tcagggccag gtggaggtcc tgtaccaagt ctcctgggc accgtgtatg     9540 atgacaccaa tgacgccaat gtggtctgca ggcagctggg ccgtggctgg gccgtggcat    9600
tcccaggaaa tgcctggttt gatcagggct caggacccat tgtcctggat gatgtgtgct    9660
gctcagggaa tgagtcctaa ctgtggagct gcccgcacaa tggctggctc tcccacagct    9720
gtcagcacag tgaagatgct gtgtcatctg ttcagatggg cctccaagac cttgggcctc    9780
tattttagtg tgtggttttc tccatgacaa ggcttctctt tgcactggcc tcttcccagc    9840
ctgagcttct cttcaagatg gccagttttct ctgatacctc agcaaggcaa taacctcagc    9900
aaatgttgtt ggcgtctttg aattttatgg gtaggcacta gcttctttct tatgtaggtt    9960
cctatagcaa acaagggttc aatctacttt caggctgtaa gaatgaattc ttccaacatc   10020 ttttttttgag actaaccgtt aaggtttata tctactattc cactctcctg gatgactctt   10080
ggggagcatt tctaagtgat gagatgggga caggcactca gcatttctct cgctcatcat   10140
cctgggcact gggactgact catgttttct tcttttcctt gcagccaccc aaataaattc   10200
tactacgaca ggtgagtctg ctacaccca gtccagcaat atttctcttg ggaattccac     10260
cctctcttgt ttcagaagt aggaggagta gggtagactc ccctgggggg gtaatttct     10320 ctctgaggac tctgatcttt gttagggtga cgagctgagt tcccactgcc atcactctca   10380
tgtctggttc accgtggagg gcccctgtgg cctcctgcta ttgcctgctg atagtgctaa   10440
gtgctggcag agatgctgct gtggaaggag gctttggtcc tcccattatt tcagatgaaa   10500
ataactgtct aaattaaccc atggaaaatt aggaccttca ttttagaaac atagccaagt   10560
aatacttctg cacgtatttg tcaaataaag aacactttca ctttgaggga gccatccgca   10620
```

```
aagcgttttt gtgccacagt gaaaatatcc tgggccaaat atgttgggag gtgctacata   10680
ctctagacct tactggccat aacagtgta aactggaatg gtcaaggctc tgagaagtcc    10740
tgtactaagg aaaaggattt aactttgtca gtcaaacaaa ttactatgga atggaaaaat   10800
tatctactaa aatcctaaac agcttcattt tttttttctag attggtggca tccaacaact  10860
acaaccactg caagtaggta tcacattttc tacctgaacc ataggtcata catttcttat   10920
ccccaagctt ggctatccat gagcgaatgc tctgccccac cccagccttc ctcaatctgc   10980
acatagccct ggcctgtccc actatacccct tcacctcttc atttgaatca atgagataag  11040
tattcttaaa ataatagact taaaggcttt tatttgggg ggtatctcca aagctttagg    11100
aggaagaagg gagacaaata gtaaatggat aattttacta caaattatgc ttttccatgt   11160 cattttatt tcaccatatg gctatgtttc aatagatttt cattgctttt aaaaaataat    11220
agggatactt ttctgtgtta ttaaatcttt tctcacaatc atttttaagtc cctgtattgt   11280 attctattat acagatatgc catgaattat ttgacaaatc atcagatgct agatatttgt   11340
ttgtatttct tcattactgt aaatgatttt gtgatgaaga atatttttat agataatttt    11400
tttgcatacc tcactaattt ttcctttagg atataaatgg gtttactgga ccaaagtcaa   11460
tgtcattgta gtgcctggta catagaatgt acttcatgca tattaacttt tactgtgtta   11520 ggtatttaa gatcttgctg tgtgtatggt caaactacca tcaagaatgg ttgtaaaatt    11580
atggaatgat gtaagagaca aactgatctt cttcctcaga gctcacaata ttattttgta   11640
cacaacaaac tagaaaatta cagttgtgac aactgtttcc aaggaaaagt tcagtgtgca   11700
aagaggaagt attagtagag atcttccttg attggggagt tagggaagt tccttatgga    11760 agtgacattt aagctgggag ttaatagagg agcaggttca tttgctgaag tgtcttctaa   11820
ccagaaggga tgctttgaag gccctagggt gggaaggagc ttggctcttt gaaggagggt   11880
ggggtgcggg caaggaggga ctgcaggaaa tctgtcgggt gaggccagat cattcagggc   11940
cttgtgggtg ggttaagact cccatcttta tcctaaaggt agggaggctg cagaaagatt   12000
ttaatcttga gaattagcta attggaaata tatttgcaaa agatcatgtt tatctttct    12060 gccaaactgc atttcctgaa ggcaggggcc atgtctgcct ttttcataat gtatccttat   12120
tatctagcat tgtgtctgcc tttcaagaac tgttttattga aggaataaat gagtgaatga   12180
atgaatggat aaattaatga ataaatacat aattactgtt ggcattttgg catacattcc   12240
atacactgta tacacacaca caaacacaca cacacacaca gtatggcatg ctttatatcc   12300
cattgtataa tccatcattt tcatttaagt gtatataata cttttttcat gaccttaaaa   12360
ttagcatttt tataacattg aaattatttg tatagaagaa ggtttaatga ctatatgatt   12420
ttccactgta tagatatatc atcatttagt taaacggtta ctaattgtgg ggcaaaaaca   12480
ttgtttccaa ttatatttta taatgttaag tgactatata caatagcata ttttataacc   12540
atttatattt aatgattaga aatatgtaac tcgtatcctt gtctctgaaa gtttgactt    12600 atccttaatt atttcccagt gtagaaatag aaagggaggg caggccacat gatcttcaag   12660
aaacactgtc ttcccatcaa atgggagaac gtatttctat ctcataaggg acttgtatct   12720
aggatatata agtgactctt gtagtcaatg ataaaaagtc aaataaccca actgaacaat   12780
gagcaaaaga cctgaaagat atttctctac agaagattca cagatagcag agaaggcatt   12840
ggaaagatgc tcaatgtcat tagccgtcag ggacatgcaa atgaaacacc cagtaggtgg   12900
gctgtagtca aaaagccaga taatagcaag tgttgatgag gatgtggaga aattggaaac   12960
cttatgcacg gctgcaggga atgtaaaatg gtacagccac tttgagaagc agtttggtgg   13020
```

```
ctcctcgaaa ggttagacct ggagtcacca tatgacccag cagttgtatt cctaggcata    13080
tacccaggag aaatgaaaac atatgtccat acagaaactt gtatgtgaat gttcaggaca    13140
gctttattca tagtagccaa atgtgaatgc aatgcaaatg tccatcatgg tgaatcgaga    13200
aacaaatatg atatgtccat gcagtggagt attatttggc aataaaaatg aatttaatag    13260
tggccgggcg cggtggctca tacctgtaat cccagcattt gggaggcca agatgggcgg     13320 attggctgag gtcaggactt cgagaccagc ctgacaacg tggtgaaacc ctgtctctac      13380
taaaaataca aaaattagct gggcatagtg gtgggcggct gtaatcccag ctacttggga    13440
agctggggca ggagaatcgc ttgaacccgg gaagcggagg ttgcagtaag ctgagatcgt    13500
gccactgcac tccagcctgg gtgacaagag cgaaactcca tctcaaaaca aaacaaaaga    13560
aaaaaaagaa tttaatattg atttatgcta caacatgatg aactttgaaa acacattgag    13620
aagtcagtca aaaaaactac catattgtac aatttgtttt atatgaaatg tccacaatag    13680
gcaaatctat agagacagaa aagtagatca gtgggtgcca ggaatggagg gtgttgagaa    13740
gaaatgggga gtgattgcta atgagtacag ggtttctttt tggggtgatg aaaataatct    13800
aaaattgact gtggtgattt cagagctctc agtatgctaa aaaccatgga cttatcccct    13860
tagaaaaagt aaagaaagag ttatgaaaaa gaaaaaaaa gacgttttaa tttctatcac     13920
tgagtgtgca catgttttta aaagttttt attactataa accaaccaac aaaatgtttg     13980
accacttaat atttatcctt ttctgataaa taacaatagc taatattgct gggtgcttat    14040
gtgcctggca ctctctaaga gtttatatag acatagaaac ctatcttatg tttatgtata    14100
aatgttcata tatacatatc ttatttaata ccctcatcag acagatgagg cagatgccat    14160
taccactctc attttctga tgaggaaact gaggcagaga ggttaagtaa ctggctccag     14220
atcatggagc tgatagaggc agagccaaga tgcaaaccca ggcttcttgt tgcagaaacc    14280
ctgctcctaa cccaacgttg tgctacttgt gaattggcag agtcctgtgc tcatggaaga    14340
cgctagggaa cacactgtgt tatggagtgc tctccacggg tcagcactgt gttcagccag    14400
gactatccca cgtccctgtc tgtagctgat tgaacaatga tagctgtcac tttgttgctt    14460
tcttggcatt tttgctagag gtgacacatg ctccctctga gcttgggtc acctcctcgc      14520 agagggttgc tgtccaggcc taacagggaa agcagggact tgaatcaaag cttctaatgt    14580
tgggccacct agaaccaggc ccaagagagg ggacttgttt acaggaaag ttaagtcttg      14640 ttataaagtg cagaagatga aactggatga tacttacaca gatgattcct tgtcacaaaa    14700
tacctgaaga cctggtacaa tggagatgtc ccctctctcc tctctaggac cctcttcaaa    14760
ttgtggtggc ttcttattct atgccagtgg gacattctcc agcccatcct accctgcata    14820 ctacccccaac aatgctaagt gtgtttggga aatagaagtg aattctggtt atcgcataaa   14880
cctgggcttc agtaatctga agtaagtaat gcctggtcat ctggtgaggg gtgagttcct    14940
ctgcagcaca cccactggtt tagactgtgt cctgggctgg gatgcttttc actctcatgt    15000
gccatggaca agcttttggt ggctttgatt cctaccataa agcatcaggg aacactgatg    15060
tcctttgact taattgagga agagctagaa gaaaaacctg tattcaatgg catccctcgt    15120
aaagtgcaaa ctatttataa aatggagggg caataggaat tcaatgttg acttgaatac      15180 attttctcca tacagattgg aggcacacca taactgcagt tttgattatg ttgaaatctt    15240
tgatggatca ttgaatagca gtctcctgct ggggaaaatc tgtaatgata ccaggcaaat    15300
atttacatct tcttacaacc gaatgaccat tcactttcga agtgacatca gtttccaaaa    15360
```

```
cactggctttttggcttggtataactccttcccaagcggtaagtgcacactagaccatgc      15420
ctatgaggcttggtggatttacccagctgcctctttggggcaccatggttccccaagga      15480
aatcaaagaagggcctcagcgatgcacggcccattctctttctcttggcactgactgtgt    15540
gggcaggcccttgggaaggcagcaaagggtgcagactggggttccacctggccttggt       15600
ctgccaccaactctccagggacctggtgactctccttcagagccaccccctctccgtctg    15660
gaggtgagggatctgagcttggcgatgtctagagcccttcagctctgcatggagcgg       15720
tccagtacctccaccccagcttttccacatttctatttggcgactttagaggtgggaaaa    15780
ggcctgtgggatgcttggcctttgaggtttgttgtgggacatttgttgtgggacatggcc   15840
atgatctctcagttaatgtgtctttcagatgccaccttgaggttggtcaatttaaattca    15900
tcctatggtctatgtgccgggcgtgtagaaatttaccatggtggcacctggggacagtt     15960
tgtgatgactcctggaccatcaggaagctgaggtggtctgcagacagctagggtgtgga     16020
cgtgcagtttcagcccttggaaatgcatattttggctctggctctggccccatcaccctg   16080
gacgatgtagagtgctcaggacggaatccactctctggcagtgccggaaccgaggctgg     16140
ttctcccacaactgtaatcatcgtgaagatgctggtgtcatctgctcaggtatggcccaa   16200
tgccatggaaggcccatttcacctgtaacttgctataaagcaagagcttaaggccagtgg    16260
ctgatggtgtctgtggcccaggcaggagctggtcattgtgtcctcgtggcctgcgcactc   16320
cagaagagcatgcaggggctgctttatcttggccagttctggacccagggccattat      16380
gctgaacactcatctgactaaaggacctccagcaatgattttacttctttatgcttcagt   16440
ttccttgactgttgagtcggggtggctatgacagtacttgctactggtgacaattgggat   16500
ggttttagaacaatcatggtcaaggagagagtgatggggttatgacctcagctgtaatc    16560
ctgatgaccaacaagtatgacgggacttagggagcatctggggaagctgggaaggcttctc  16620
aatagcaattgctgggtggacctggggaccctcgccaggggggtcaggttatgggccat    16680
gtaagtgtatctctgtctcattccggccccctcctccaagccacatgtctgtgacctatgc  16740
ttttttttctattccttttttcaggaaaccatctatcgacactggtaagtccctccgattt  16800
ccattccactcccctggtctccaggtctctccattactgctgcctagactgtgcagggca    16860
tgttgctcactctccaaggagttcatctgtggtaccatcctctacagcccctgtcccctc   16920
ccctgccggccaccaggatagtgtgcccctctctgtgcttcagtggcctgacccacctaa    16980
gattaggatcccagtcagtcccgaggtgaggcccgccactgtcagattgactgtcct     17040
cacagacaccagaccctgacagtgttggccaaatggggcccactgcatcgcagagctcc     17100
tccctgcctgcccctgagctgctctgagtgttcccagcatggccctggcacctctccaac    17160
acccccactgccccgccccctgcttgcttttgtcatccccctcctggcctccatagcagc   17220
agcttcaggcctgtgccctcccatccattctacactgtgcagcccttcaagagattcct    17280
cagggtcttctggtgatgacccccgctcctcagcacagcatgactgccagggctccccatg  17340
atctgctcccctatgcttggtgccctctcccatcctctgcctgctccatctacacgaggg   17400
ttcccaaatctattccaccccaggtgcagttgcacctgctgttcctctgcctgggacaccc  17460
cgtttctacctctttgcctgcccccctaattactgcccttttttcccccactccatctgggg  17520
caggggccagacttccaggctcctctccttccccaggcttggtcaatctcatccttttc     17580
ccagtgtgctgggattcgctctcctccagacctcccaaaggcaagtgagctcccccaagg   17640
gcaaggcctgtgtccagctcctccctgtggactcaggcttggcacagcatctgcacagct   17700
catgagcagtagacagctgtgtcagggatgccagaaaactgatcctgatcttttcttttt    17760
```

-continued

```
gtcaacagct cctttctca acatcacccg tccaaacagt aagttctgag ctccctgaca    17820
agtctgtggc agagtggcct ggaaattccc cttcccattt cctcagtgac aatgggctg    17880 gggaggagat ggcttccccc aaagtggtct ccctgcaaga gtgccctgcc agccctcagt    17940
ggacggtcca gatctaggcc acctcttgct cttacttggt ttctgtcttg ggaattattt    18000
tataaaattt taaagtaatt taaatttaaa gtagtccgca ggtagactgt gcagtgtgct    18060 ctggggtca ccgacattcc cacttttgt cctgacagca gattattcct gcggaggctt      18120
cctatcccaa ccatcagggg acttttccag cccattctat cccgggaact atccaaacaa    18180
tgccaagtgt gtgtgggaca ttgaggtgca aaacaactac cgtgtgactg tgatcttcag    18240
agatgtccag taagtgtgcg cccagaagaa tgccttgggg ccccacagac ctttcaagag    18300
ggaataaatg gtgcttaagt gtgcgcccag aagaatgcct tggggcccca cagacctttc    18360
aagagggaat aaatggtgct tagaaagcca ggagagaagt ttgctgagag acattttga    18420 cctagcccag aggcatcccg tggagagttg gggaggggc acgagagcct tggagtggac    18480
aaaagctctg gtttcaagtc ctaggtcttt caccaatttg ctgtgtgacc acaggaagtc    18540
actcaacttt cctgagcctc agtcaaaaga ggggaataaa atacctgctt tcctcacctc    18600 actgttact gggaaggtca cgagaaacag agaggagaga gagggagaga gatgtgaaaa      18660
tatttacaaa atgttgtcca gtggaaaaga tggttgttaa gtagtaatga tagacttagg    18720
ggcaataata gcactaataa tcctattaac aaccacactg gccaggtatg ctgcctcagg    18780
gttgtaatcc caacactttg ggaggccgag gcaggaggat cacctgaatg caggagttca    18840
agaccagcct gagcaatata gggagacccc ctatctctac aaaaaagtac aaaaattagc    18900
tgggtgtggt ggcctgcacc tgtagtccca gctactaagg aggctgaggt gggagaatcg    18960
ctagagcccg gggagttgaa ggttgtggtg aactatgata gcgccagtgc actccagctt    19020
gtggaacaaa acgagaccct gtctcaggaa aacaaaacaa aacaaaaaga acaattgtat    19080
ctgttttgtg gaacccttt tctccaccca ttccttcctt catgtgagtt ccccagggt      19140 cgggcagaga tggaggaatt gctgctccag agggtagggt atctgctctg catccaatca    19200
taagtagaaa tcatcgtttt aagcagagag gacattacta aaagcacttt tcttcttc      19260 tttcttctt tctttctttc ttttctttc tttctttctt tctttctttc tttctttctt      19320
ttctttcttt ctctctctct ctctctcttc tctctctctc tctctctctc tctctctctc    19380 tctcttctc tctcttttctt tctttctttt ttttccgga catggagtct cgctctgtca      19440
cccaggctgg aatgtagtgg cacggtctcg gctcactgca acctctgcct cccgggttca    19500
agcgattctc ctgcctcagc cttcaagta gctgggctta caggcacacg ccacaatgcc     19560
tggctaattt ttgtattttt attagagacg gggtttcacc atattggtca ggctggtctt    19620
caactcctgg cctcaggtta tcctcccacc tcggcctccc aaagtgctgg gattacaggt    19680
gtgagccacc atgcctgatg tcaaagtac attaatatat gatttatcca aggaggcggg      19740
tggcccagct aactgtgaag aggcaccagt gttgctagt gtcctgaaca aggggctaca      19800 ctaattctt ctctaacagc cactgttgaa caaaatagtt ttccctgttg atttctgttt     19860
gcagtgggct ttggagtctc tgctttagtg attcatttgg gattttgcaa aagatacatc    19920
attttattct ctttgtcatt acaatacaaa gattgcactt aaagctgatg cagtcctatg    19980
ggaaaaggtt gaccatgact ggttctttaa ccagcatctt gatagcaatg accatcacca    20040
tttgtgacat tttacaaagc cctttctgt atgttgtttt atttgagctt caccatagcc     20100
```

```
ctcttcagtg tgcatggatc agattacttt gcctttgtaa ataggaaaag ctttagagag   20160
attatttgac ttgcccagta tttatttatt caattattta tttctctcac tatgaattca   20220
tgcatattga ttttattctg tgggggcact agggactttt cgatggaaga aaatggtct    20280 aaatcaggat gcgagcccct cctttcctga tgtaaagggc tgacaggtga ggggctgtag   20340
atttcatatg tgtgattgca aagggcagga ctaagaccca ggcatggagg ttgagggaag   20400
atgagactct cttgatttaa ggatacctat gactttcttt tgtttaaatt tttattttc    20460 ttttattttt ttgagacagg gcctcactct gtcgcccaaa ctggagtgca gtggcacgat   20520
ctcggctcac tgcaacctct gcctccttgg ttcaagtgat tttcctgcct cagcctcctg   20580
agtagcctcc ctcaccctac aggcttgtgc caccacgccc ggctaatttt tggatttta    20640 gtagagacag ggtttcacca cgttggccag gctggtctcg aacttatgac ctcagatgat   20700
ccacctgcct tggtctccca aagtgctggg attataagtg tgagctactg cgcccagcca   20760
aggagaccta tgactttcat cgatgaactt tgtcagagtt tctggcacag aggtgtgacc   20820
ccaccctgag atctgacccc ctgcgtcaaa ttctgggagg aaatgaagcc aaatggtgtg   20880
tcctctctct gcaggcttga aggtggctgc aactatgatt atattgaagt tttcgatggc   20940
ccctaccgca gttcccctct cattgctcga gtttgtgatg gggccagagg ctccttcact   21000
tcttcctcca acttcatgtc cattcgcttc atcagtgacc acagcatcac aaggagaggg   21060
ttccgggctg agtactactc cagtccctcc aatgacagca ccagtaagtc cccttgtgga   21120
aatgctctgt tgggactggg gacatcctga gagcatctgt ggctcaactg tcctgttgtt   21180
gtgaaataag aaatgaagga accctttcag gtcaccaggg cttgattttc agctgaaagg   21240
gaccaggagc agtgggactt gggactctgg ctgcccagaa ataaagtcag ggctagaact   21300
ggctgatggg tgatgattgg tcttactgtg gtcagcagag actaagtaga gggtccagat   21360
gatgctcttc gtgagagtg atgagtcagt gccaaaggca gaggtgacct cttggcttga   21420
aaccttgtga ccttctcaga gtgtgggaca ctgtggccat ggcctgagac ctaacacatt   21480
tggtttctat ctgaagatgg actgagctgg gtggctggaa gtggctgaga taggtcact   21540 cagacacttc cagcagagcc tgtatggcca tgatttgagt tgctgtatgg actgatatgt   21600
agaatggcca agggccaggc aaggtgacat ccagggtctc ttatgcagtc aggattaaag   21660
actgacttgc ttcatggcta aaagaccttg tttcatgaca ttcccacaat ttgatcatac   21720
agttacttta ctttatagat aaatggtaac ttggccaaac ataccactta tttaaaaatc   21780
ctgcctccaa ttctccatca gagaaatcct gagtccacgt gctctccttg ggctttcata   21840
aggatggggc tgacttgacc ctcgggtcct tgggggattg cagtgaggtc tatgcccaca   21900
tcctaagtgc tgaccctccc tgtcagccac cctggtctgt gcacttttta agtggaaaca   21960
gcctctggcc ccgtaggact tgtggagtct ggggcagtga ctgagtgcct tatctgtcct   22020
tgtctatcag acctgctctg tctgccaaat cacatgcaag ccagtgtgag caggagctat   22080
ctccaatcct tgggcttttc tgccagtgac cttgtcattt ccactggaa tggatactac    22140 gagtgtcggc cccagataac gccgaacctg gtgatattca caattcccta ctcaggctgc   22200
ggcaccttca gcaggtaag cctggggctt cccattccat ttcccagtgc acaagctttc    22260
ttagagcggt atgtcctgtg cttcttgaat tctggggatg aagaaattat gattttggga   22320
taatcaggac ataattggaa taaggaagaa taaaaaacct tggtgctat gatatggctg     22380 cagctacttc caaataggaa gaaggaagct gagcagaaag agtatctccc gctgtgtcca   22440
gcagagaggg cttctggcag accgccactc ccatcagcaa taacaacagc agctcctgga   22500
```

```
gcaggtccag attttgcagg gcctgaagat tatacagtta gggttggggg tgagaggcag    22560
gtgttgagat gggcaggggc ctcattaagt caaagaatgc aatatctatg aacttttata    22620
aactttgcaa aaacgtatgg ctgtgcaaac acattgctag gccttggagg aggcctgcac    22680
attgcagtag gcagggaaga gggggcccaa aagcttcagc ttcattagct ccatagtcag    22740
ctggcctctg cagctaccat ttgttgagct atcaccatct aagatgggcc cctgcatcca    22800
attttgggtg aaagtgaagc caatatggtg tgtcccttct ctacaggctt gaaggtggct    22860
gcaactatga ttatactgaa gttttcaaca gcccctacca ccgatttctg tggtttgcct    22920
gggactttgc agattttagc atagaaagtc ccacgttcca ggaaacccct cactcccagg    22980
caaatgagga cggttagtca ccctacaagt ggcagatgct gtgattggtc cttgtcatac    23040
tcccccagtg aaggcctggc cttaattgtg ttgggttctg gcttgctgtg agtttggtca    23100
gtggaagtca gtccactgaa ggtgaccatt gttcctatgc caagtgagca gcctggagac    23160
tccctgagcg gccccgctga gggcccttca cacccattca cacccattca cactcgttca    23220
cacccattca cacccgtttg gagcggccag acaactctgt cagccctgtt tcttctaact    23280
tggctgatca tgaatagcac acgccacatt cttattcctc cactcattta tttatttta    23340 ttttatttta attttttaat gacaggttct cattctgttg cccaggctgg atgcccaggc    23400 agggggtgcat catagctcac agcagacttg aactcctggg cttaagcgat cttccagcct    23460
cagcctccag agtagctggg actataggca tgcaccacca cacccagcta attaacaaat    23520
ttttttttgt agaggtggga tcttgctatg tgtcccaggc tgatctcgaa ctcctgagct    23580
caagtgatcc tcctgccttg gcctcccaaa tgctgggatt atgggcatga accactgctc    23640
ctggcctcct ctatttcttt aaataaccat attgcctatc acactgagtg cctcaggggc    23700
agggccaatg ttttgttcat ctttgcaacc cccagtgccc ctggtcctga gcctaagagt    23760
tgatatagta ttattaacag ctcatacaga tatcagacac tgaactaagt gtgctatata    23820
acttttaaaa ttctcaggac aactttattc ccacttaatt atgaggcaac ggaggcttgc    23880
agaaggtaag ccacttgccc agaaccatat ggccatgagc tgcgggtcta agacacagaa    23940
gtagggctgt gccatccatg gctggagctt cccacagctc caccaggctg gcctgtgata    24000
gtgaattttt atctaaaatt agaactgctt cttctgacca agaaataaat ctgcactcca    24060
tgttcattat ttggagtgga ttcagaattt acctccatcg taggcaccac aggcaaatgt    24120
gacatccatg caaatgatca tgttaatgta cagggttcaa tggaaagcac ttgagagcat    24180
ctttgaaaga gtaagaaggg tcatactgtc atgtgcgtcc gtgtgaaaag accaccaaac    24240
aagctttgtg tgagcaataa agcttttaa ttacctgggt gcaggtgggc tgagtccaaa    24300
aagagagtca gcgaagagag ataggggtgg ggccgtttta taggatttgg gtaggtagtg    24360
gaaaattaca gtcaaagggg gttgttctct ggcgggcagg ggcgggggtc acaaggtgct    24420
cagtggggga gcttctgagc caggagaagg aatttcacaa ggtaacgtca tcagttaagg    24480
caggaaccag ccattttac ttgttttgtg attcttcagt tacttcaggc catctggatg    24540
tatatgtgca ggcttgggct cagaggcctg acaaagggt ttattgcggt cgtatggttt    24600
aagtcatacg gttattgtg acaactgttg gcactgaaat ataaagcaaa acaaatttt    24660 taagacagtt taaagtcaga aaatgtacgc taagagcagg tggacaaggt agaaccctt    24720 cctgtgggtc ttccccagac ctggaccag agtgtaagct ctggcaccct gtgctggctc    24780
atagccaaag gataggcacg tgccatggcc atctctgagt ggttctggga ggggtggaag    24840
```

```
tcttgttgag tcatgtccct ctcattcaca cccaaatcag ctatgggatt cccttagcag   24900
gtgacatgtg cctgactctg ctctcttgcc tgcctctcct aggcagacaa tgacaccatc   24960
gactattcca acttcctcac agcagctgtc tcaggtggca tcatcaagag gaggacagac   25020
ctccgtattc acgtcagctg cagaatgctt cagaacacct gggtcgacac catgtacatt   25080
gctaatgaca ccatccacgt tgctaataac accatccagg tcgaggaagt ccagtatggc   25140
aattttgacg tgaacatttc cttttatact tcctcatctt tcttgtatcc tgtgaccagc   25200
cgcccttact acgtggacct gaaccaggac ttgtacgttc aggctgaaat cctccattct   25260
gatgctgtac tgaccttgtt tgtggacacc tgcgtggcat caccatactc caatgacttc   25320
acgtctttga cttatgatct aatccggagt gggtaaggag tgtctttatg ctatggcctt   25380
aaacctttac ttgataactc aaacatgagt agccccaaag gcttgaagaa tgcaaatttt   25440
gatgaactgc agttcccagt acttccagct taactggatc cctttctaca tgtagtgatg   25500
tcctgtagct ttcacctttg aggtgctttt actctgtgtt ctgtatcaca tccctgattt   25560
ctcatcaggt aggatgacca tgtatcatct ccagttaaca tctggggaga tgggtgtctg   25620
gagaatagaa cagctcagca gtgttcactc agcaggttag ctgtaaactg tgatcagact   25680
ctaggtgact gaactccagc catacggtta aaaagacctg cgtatagtgg gaaaagcatt   25740
gatttggagc agaccaaggt tgaaatgcca gctctgccac gtgccagttg catgattctg   25800
ggccagtgaa agcacctcta tggaccagtt gctcgcctgt caagtgggga taatgacacg   25860
cacatcataa ggctgttggg aggatggaat gagagagagt ggatgtggca ctgagcacag   25920
agagtgtgcg gcaggtggtc caccaggaat gtgcactgaa gatggcagga gccctgctgc   25980
cctccttcag cctgggaata gaagctctgg gagtccatgg gttccagtca agctcaggag   26040
gtgcagaggt caggccagag atgtcaggct ggggccagag ggtgtgcagg ctgggctgct   26100
ctaccatagc ccagcttccc tggatgactg catgtgggtg aagtgggtt tgactcttct   26160
gcactcatga tgacaccatg atgtgcaact ccagccccct ctgaagtctc tgttgatgga   26220
tgtgtaccac acttcttggc ttacaatata gacctggaca cttcagtagc cattgccttc   26280
caagagaatt tataccaata ggataaagag ttctactagg aattagaggt gggcagattc   26340
aattcgacac cctcttgata tgctaaacgt agcacctctt tccaggcaca gtgtgaacat   26400
atgtcagttc agtaggtagg tgttgaggct caccttgttt acagtctatg cagcttgctc   26460
aattcacagc agccccttg gtggctgaga ggagggaga aagcttaacc agattcccgt   26520
tgtacaaata gtcataaggt gacttttgaa tttgtgtgaa ttgattgaca ttaatgaaaa   26580
tgagtgggtg accttagttc ttccttgcca aaggattctt tctggtcaaa tcctgccatt   26640
tctatatgac aatgcaattt gctgggaaga cggggatgtg tgtgcagggg tagatgtacc   26700
ctggctatac ctggagcaca gggacttatt ggctacacct ggccatcaac aagatcatcc   26760
acctggaagt ccattagaat gacctgggc tccaaacaca ccctgcccag gccctacccg   26820
tacattctct gtttggcctg gtggggcttg ggcatgttac gtttaaaaaa tcttgagtga   26880
ttctgaggtg gagtcatggc tgtggcttcg ctgtggcatt ctggtctgcg tggagccctg   26940
aatggcaggg tttacggca aatgcaatga ctgcccaggg gcttctaagt gaccctgacc   27000
tttttcccaa gtgtcccacc tctgaacaag cctctggcta ttttgcttc ctcctttgcc   27060
actaagggag ctactgtgaa aaaaaaaac aaaaacaaaa aacaaaactt ggtatttgag   27120
agaatctggg ttgcctatgg aggaaggaag gaggctctag aagacagaag gaggggagca   27180
gatcctggcc aggttcccag gctgagccag actgccctgg agaccacatc caccacccac   27240
```

-continued

```
gagaaatgcc catcctaggc cagtgggcca gttttcctgg cttttctctt tgccatgccc     27300
ttcaaaatcc caccaatcta taataactgg gttagtgtga gctgcttctt ccatcttagg     27360
aaaattcctg taagcatatc cttaggttat tttccctctg acccctgctg agaggaggtg     27420
ccccagggaa tgaggagggg gtttatatcg gtatagggc tcctggaggg ttcgcaggcc      27480
agtgtggaac gtacagctgc atggggctca ggcaggctg aggagggtca ggaaagagag      27540
gccctgggag aggagggtc aggcactgt actcagagtg cagccgaatg agaccttgcc       27600
tggccctgac accaggtgag agaagggaag gtcatttact tttctgccct gtctctgggt     27660
cccgctcctg ggctccaaac tccagctact tccctgactc atctggttta cctgggtgca    27720
tggagcatgt ggtcattgtg ggattaggcc tcaacccact gtgcagtatg ggacctgctt    27780
gtctattggg aaagccctcg caggctttgc tgcctaagga tggcggtgag gtaccggagc    27840
tgccaggatt tctctgcagg cccctcagtg agtgtctgat ccacacgttc tgacagaagg    27900
aaggtgaggt gtgcaggagg caggggcagt gaggacaggc tgtggagttc ctcacctggt    27960
acaactgagt catgaaggaa gaatcgggcc ttggtgagag ctaaggggct actgttctct    28020
tccagatgcg tgagggatga cacctacgga ccctactcct cgccgtctct tcgcattgcc    28080
cgcttccggt tcagggccctt ccacttcctg aaccgcttcc cctccgtgta cctgcgttgt    28140
aaaatggtgg tgtgcagagc gtatgacccc tcttcccgct gctaccgagg ctgtgtgttg    28200
aggtcgaaga gggatgtggg ctcctaccag gaaaaggtgg acgtcgtcct gggtcccatc    28260
cagctgcaga cccccccacg ccgagaagag gagcctcggt aggtggtcgc tctcagaccc    28320
cactgtccac cagggcgcag acccctgact cggggacttg ggatgttcct cttggtgtca    28380
tattccaact cagattgagc cctacattgt gctgcacctg gtcatacgga gttgaatcag    28440
acctggttcc cgcctccccc aaggctcatg gtccttggag gacccgttgc agggcgaggt    28500
caagagagtt ctgacctgga tgcccatag acctgacgtc ccagaatcca tgcttctcat    28560
ctgcaaaatg aaaatgtcaa tacttacttc ttagcactgt tgagagggtt acttacataa    28620
aggaattttg gtgaaactgc ctcagcctgt tcctggtgca agtcatttga gtgcttggta    28680
aatggtactt tttgttactc ctgttgttgt caccccctgtt                         28720
```

```
<210> SEQ ID NO 8
<211> LENGTH: 3166
<212> TYPE: DNA
<213> ORGANISM: Homo sapiens

<400> SEQUENCE: 8
```

```
tcttcctctc ctcctctgcc aggctctgtc ctggtgccct gtctgttatt gtggtctcct       60
ctccttccca gacgtgttgg tggctgatgt ggaggagaca gccagcaccc agggaggta      120 tcacagcact gccatctctt ctggggtctt cctggctgtg gttctggttg tggcagcctt      180
caccctgggg aggaaggcac acagcaccag tggccggcct ctgagctcct agatatgaag     240
cccagagaag gtgtttagat attggctctg ccagcccagg cacccgagag aggatggaag     300 aaacaaggt gcagagcttg gcgcccagca gcacctgaac tccatttagc ttggcacagg      360
tgtatggtgg ggtgggtgga ggtggggtga agaaagatgg ggtgggtaga ggtggggtga     420
agaaaggtgg agcgaggttt tccccagatc cgaaggctca gtgctgggtc aaaatgtcaa     480
aggtaaacag gtgctaacgt ctaaagcctc acctgcaact ctaagccaaa cattagtaac     540
agcagagctt tctctaggtg gaatttctga gccttttttt tttttttttt ttgagacagt     600
gtcttgcttt gttgcccagg cttgagtgca gtggcacaat ctcaactcac tgcaacctcc    660
```

```
gtctcccggg ttcaagcgat tcttctgcct cagcctccct agtagctaag attacagaca      720
ggctagacca tgcccagcta agttttgtat ttttagtaga gacggggttt catcatgttg      780
gccaggctgg tctcaaactc ctgacttcaa gtgatctgcc tgcctaggcc tcccaaagtg      840
ccgggattac aggtgtgagc cactgcaccc ggcctctttt ctgaccttt ataagctcgc       900 ttcttaggcc tgtagcataa atctcagcct ttccttaggg tagagccagc tgaataaaga      960
acctttttca gagtaagtgt caatttggcc actgttgcct tcgtttcccc taagaactag     1020
atcctttcaa attaagcaga caggtgggt ggttgtcata cagaatgaga agggcaact       1080 cgtgtgtctt cccagtgtcc ttggagtgtt ggttcttccc aaagcaggat atgcaggatg     1140
cagcctggag aaagacaaga atgctaaatg cattgtaagt ttcagtggct gtgattgaaa     1200
attaaagatg attgcctcca tttctctagg gatctgcctc ttttggtttt tgacacttca     1260
tctccagaac tatgggctgg ggcggttcag ggaaagaagc aaactcctta gggcccttag     1320
gaagggagtc ctgtttgcat gaggtctcca gagagaagga gattgacagg tgacccaagg     1380
agctcagaag aaacaaaggg atgagctggg ttccaaggaa gcagtacatt tgcctagaaa     1440
atcagagaga aatcaggctc agggctccta ggtcaggctt ggcaggaatg ggagcttttg     1500
tgtactgccc tggcaatgcc agtgtttgcc ccatgaagcc aatctcagga ccctgtccc     1560 aagaggggac agctaagaca gcctaactct ggatgtgtga gttgagctgc atgagacccc     1620
agcagggcaa tggctacagg ggaaacccca ggacaagggg acagaagaatt ccagcagaga    1680 cttggccata gctgccagct ctgactaggg ctgcccaaga gctgcccacc accggcagct     1740
gtggtgagac gccatgagcc tccgtgggat tcagagtgcg tcctgagccc taccaggagt     1800
cagaggagct agggggcccc agggactgtc tcttgttggt ttccattctc cttgccatca     1860
cccccaacac tcaccttaa cctcccaggc tggggcagtt aaggaaagcc ttaagggttc       1920
ccctgtgacc atgagtctgc cctgaaaagc aatgtcaatg cagtggaatg caggcaccag     1980
cccaggactg gatctgagca gatgcagaag cagcaggaag ctggagtggt gtgcgggttt     2040
gaggtacaca tcaatcagag taacaaagtg gcaagtcaga catccgagaa ttcaaaaaag     2100
ttcagaggct gggaacccaa catggaatcc caactccatc cattcattcg ttcgttcatt     2160
cattcattca ttcattcatt cattcgttca ttcactcatt catgaatgtc taagttgtac     2220
cctgtgcttg agaaggagca gtggaggctg tgggtccctg ctgtgaggat gaggggacc      2280 ctggggctgg gggctcagca ggcttgccct gagtggtccc catgagcgcc agccccaagc     2340
caggctctgt acttgaacct gtggatacaa agagggtca tgcagggtc accattataa       2400 ggggaaattt atttccacag gaaacatttc cacctcctga agtgtcccct ctccttaaaa     2460
atagccccag tagccagtgc ttcttcgcag ataaccacca cagtgttagc cacttggcag     2520
cctctcaagc aaggaggtaa tggcccctt atcagcaggg cccagccagg agtggcta       2580 gtagggacag atgagtttgg tagcaagagg cagtgaggtc caggtgaaag gtagagcaga     2640
agacagggcc accggtgaca gggctctgg actaaagctg tcagagtgtg actgagggtc      2700
cagtcacagg ggacacagag aagtgggctt gcttgggagc agggacccat cctccccatc     2760
cacaccacat ctccacactc agggaggatt gggctgacac caagtggctg tgattcccag     2820
caactgagac tgtggtttga ggcaagggtg ctcaactcta ctgcacgtga aatggcccg      2880 ggggcttttg aacctgctgc tgccaggctg cacccaagcc agttagatca gaatctaatc     2940
agagggcagg cctggacatt ggtgacccac cagactcagg ttgttccaag attgagagct     3000
```

-continued

```
gctggtttag gactccttaa atccctctga gagagtccag gttgtgccct gtgcttaaga    3060
aggagcagtg gagactatgg gtccctgctg tgaggatgag ggggaccctg gtgcggggtt    3120
ctcagcaggc ttgccctgag tgttcctgaa agatctactt tccaag                  3166
```

<210> SEQ ID NO 9
<211> LENGTH: 18
<212> TYPE: DNA
<213> ORGANISM: Homo sapiens

<400> SEQUENCE: 9
gtggtctgca ggcagctg                                                 18

<210> SEQ ID NO 10
<211> LENGTH: 20
<212> TYPE: DNA
<213> ORGANISM: Homo sapiens

<400> SEQUENCE: 10
aggccagata cttggctgac                                               20

<210> SEQ ID NO 11
<211> LENGTH: 22
<212> TYPE: DNA
<213> ORGANISM: Homo sapiens

<400> SEQUENCE: 11
cttcagatta ctgaagccca gg                                            22

<210> SEQ ID NO 12
<211> LENGTH: 22
<212> TYPE: DNA
<213> ORGANISM: Homo sapiens

<400> SEQUENCE: 12
tgcacatctc tgaagaccac ag                                            22